United States Patent
Narayanan et al.

(10) Patent No.: US 12,251,221 B2
(45) Date of Patent: Mar. 18, 2025

(54) ASSESSING DEVELOPMENTAL DISORDERS VIA EYE TRACKING

(71) Applicant: EarliTec Diagnostics, Inc., Decatur, GA (US)

(72) Inventors: Sreeni Narayanan, Lincolnshire, IL (US); Ella Swanson-Hysell, Saint Paul, MN (US); Eli Johnson, Richfield, MN (US); Steven Shifke, Atlanta, GA (US); Jason Davis, Duluth, GA (US); Connor Eck, Cape May, NJ (US); Robin Sifre, Evanston, IL (US)

(73) Assignee: EarliTec Diagnostics, Inc., Decatur, GA (US)

(*) Notice: Subject to any disclaimer, the term of this patent is extended or adjusted under 35 U.S.C. 154(b) by 0 days.

(21) Appl. No.: 17/901,369

(22) Filed: Sep. 1, 2022

(65) Prior Publication Data

US 2023/0397864 A1   Dec. 14, 2023

Related U.S. Application Data

(63) Continuation of application No. 17/881,911, filed on Aug. 5, 2022.

(60) Provisional application No. 63/350,741, filed on Jun. 9, 2022.

(51) Int. Cl.
| | |
|---|---|
| *A61B 5/16* | (2006.01) |
| *G16H 15/00* | (2018.01) |
| *G16H 40/67* | (2018.01) |
| *G16H 50/20* | (2018.01) |

(52) U.S. Cl.
CPC .............. *A61B 5/163* (2017.08); *A61B 5/168* (2013.01); *G16H 15/00* (2018.01); *G16H 40/67* (2018.01); *G16H 50/20* (2018.01)

(58) Field of Classification Search
None
See application file for complete search history.

(56) References Cited

U.S. PATENT DOCUMENTS

| | | | |
|---|---|---|---|
| 6,670,963 B2 | 12/2003 | Osberger | |
| 7,556,377 B2 | 7/2009 | Beymer et al. | |
| 7,819,818 B2 | 10/2010 | Ghajar | |
| 7,922,670 B2 | 4/2011 | Jones et al. | |

(Continued)

OTHER PUBLICATIONS

Rusch, "Combining fMRI and Eye-tracking for the Study of Social Cognition," Neuroscience Insights, Dec. 16, 2021, vol. 16, 4 pages.

(Continued)

*Primary Examiner* — Aurelie H Tu
(74) *Attorney, Agent, or Firm* — Fish & Richardson P.C.

(57) ABSTRACT

Systems, devices, apparatus, methods, and computer-readable storage media for developmental assessment using eye tracking are provided. In one aspect, a system for development assessment via eye tracking includes: a patient-side computing device having a screen for presenting visual stimuli to a patient, an eye-tracking device integrated with the patient-side computing device and configured to collect eye-tracking data of the patient while the visual stimuli are presented to the patient on the screen of the patient-side computing device, and an operator-side computing device configured to present a user interface for an operator to communicate with the patient-side computing device.

21 Claims, 30 Drawing Sheets

(56) References Cited

U.S. PATENT DOCUMENTS

| | | |
|---|---|---|
| 8,229,229 B2 | 7/2012 | Ferguson |
| 8,343,067 B2 | 1/2013 | Jones et al. |
| 8,371,693 B2 | 2/2013 | Ebisawa |
| 8,434,867 B2 | 5/2013 | Helfman et al. |
| 8,551,015 B2 | 10/2013 | Jones et al. |
| 8,668,337 B2 | 3/2014 | Waldorf et al. |
| 8,714,982 B2 | 5/2014 | Wimsatt |
| 8,808,195 B2 | 8/2014 | Tseng et al. |
| 9,050,035 B2 | 6/2015 | Yao et al. |
| 9,239,956 B2 | 1/2016 | Hein |
| 9,265,416 B2 | 2/2016 | Klin et al. |
| 9,314,157 B2 | 4/2016 | Yao et al. |
| 9,463,132 B1 | 10/2016 | Simmons |
| 9,510,752 B2 | 12/2016 | Klin et al. |
| 9,538,947 B2 | 1/2017 | Mori et al. |
| 9,629,543 B2 | 4/2017 | Agichtein et al. |
| 9,854,966 B2 | 1/2018 | Otero-Millan et al. |
| 9,861,307 B2 | 1/2018 | Klin et al. |
| 9,936,916 B2 | 4/2018 | Sahin et al. |
| 9,962,119 B2 | 5/2018 | Macknik et al. |
| 10,010,284 B2 | 7/2018 | Khaligh-Razavi et al. |
| 10,016,130 B2 | 7/2018 | Ganesan et al. |
| 10,016,156 B2 | 7/2018 | Klin et al. |
| 10,022,049 B2 | 7/2018 | Klin et al. |
| 10,052,057 B2 | 8/2018 | Klin et al. |
| 10,117,569 B2 | 11/2018 | Shudo et al. |
| 10,149,643 B2 | 12/2018 | Shudo et al. |
| 10,159,408 B2 | 12/2018 | Shudo |
| 10,165,176 B2 | 12/2018 | Frahm et al. |
| 10,165,940 B2 | 1/2019 | Simmons |
| 10,176,299 B2 | 1/2019 | Torres et al. |
| 10,201,274 B2 | 2/2019 | Samadami et al. |
| 10,226,172 B2 | 3/2019 | Simmons |
| 10,413,176 B2 | 9/2019 | Mori et al. |
| 10,537,276 B2 | 1/2020 | Macknik et al. |
| 10,602,972 B2 | 3/2020 | Super |
| 10,610,165 B2 | 4/2020 | Samadani |
| 10,617,295 B2 | 4/2020 | Klin et al. |
| 10,643,741 B2 | 5/2020 | Gross et al. |
| 10,694,942 B2 | 6/2020 | Agichtein et al. |
| 10,729,321 B2 | 8/2020 | Samadani et al. |
| 10,863,902 B2 | 12/2020 | Samadani et al. |
| 10,885,719 B1 | 1/2021 | Ravindran et al. |
| 10,936,059 B2 | 3/2021 | Stoner |
| 10,966,605 B2 | 4/2021 | Komogortsev |
| 10,966,669 B2 | 4/2021 | Samadani |
| 11,141,095 B2 | 10/2021 | Samadani et al. |
| 11,158,403 B1 | 10/2021 | Sapiro et al. |
| 11,207,011 B2 | 12/2021 | Gross et al. |
| 11,393,564 B2 | 7/2022 | Gross et al. |
| 11,666,259 B1 | 6/2023 | Narayan et al. |
| 2007/0136102 A1 | 6/2007 | Rodgers |
| 2008/0147488 A1 | 6/2008 | Tunick |
| 2010/0056875 A1* | 3/2010 | Schoenberg ......... A61B 5/0002 600/300 |
| 2012/0178064 A1 | 7/2012 | Katz |
| 2014/0253876 A1 | 9/2014 | Klin et al. |
| 2014/0287398 A1 | 9/2014 | Singh |
| 2014/0323901 A1 | 10/2014 | Kim |
| 2015/0157235 A1 | 6/2015 | Jelen et al. |
| 2015/0223731 A1* | 8/2015 | Sahin ..................... A61B 5/16 600/595 |
| 2015/0282705 A1* | 10/2015 | Avital .................... A61B 3/113 600/301 |
| 2016/0195924 A1* | 7/2016 | Weber ................... G06F 3/013 345/156 |
| 2016/0262613 A1* | 9/2016 | Klin ........................ G16H 50/70 |
| 2017/0049362 A1 | 2/2017 | Macknik et al. |
| 2018/0063220 A1 | 3/2018 | Dhanabalan et al. |
| 2018/0357552 A1 | 12/2018 | Campos et al. |
| 2019/0029585 A1 | 1/2019 | Geva |
| 2019/0239790 A1 | 8/2019 | Gross |
| 2020/0107767 A1 | 4/2020 | Anson |
| 2020/0146611 A1 | 5/2020 | Macknik et al. |
| 2020/0352499 A1 | 11/2020 | Frazier |
| 2021/0000340 A1 | 1/2021 | Klin et al. |
| 2021/0015416 A1 | 1/2021 | Wang |
| 2021/0259602 A1 | 8/2021 | Kissine |
| 2021/0259603 A1 | 8/2021 | Kissine |
| 2021/0321955 A1 | 10/2021 | Samadani |
| 2022/0061724 A1 | 3/2022 | Gross et al. |

OTHER PUBLICATIONS

Frazier et al., "Development and validation of objective and quantitative eye tracking-based measures of autism risk and symptom levels," Journal of the American Academy of Child & Adolescent Psychiatry, Nov. 2018, 57(11):858, 18 pages.

PCT International Search Report and Written Opinion in International Appln. No. PCT/US2023/024967, mailed on Sep. 28, 2023, 15 pages.

* cited by examiner

Movie Playlist Data

| timestamp_system_us | media_name |
|---|---|
| 361409268522 | CenterStim |
| 361411985722 | 0075PEER |
| 361431439717 | CenterStim |
| 361434216413 | 0076PEER |
| 361461524245 | CenterStim |
| 361464288903 | CCTL |
| 361466199665 | CCTR |
| 361468009587 | CCBL |
| 361469817708 | CCCC |
| 361471632348 | CCBR |
| 361473434754 | CenterStim |
| 361476307507 | 0079PEER |

(a)

Eye-Tracking Data

| timestamp_tobii_us | timestamp_system_us | EyeTrack DataX1 | ... | EyeTrack Data Xn |
|---|---|---|---|---|
| 89894455873 | 361266098581 | -38.446266 | ... | 10.881472 |
| 89894485796 | 361266128504 | -38.430622 | ... | 10.7505 |
| 89894515576 | 361266158284 | -38.456818 | ... | 10.9184475 |
| ... | | | | |

ASSESSING DEVELOPMENTAL DISORDERS VIA EYE TRACKING

CROSS-REFERENCE TO RELATED PATENT APPLICATIONS

This is a continuation of and claims the benefit of priority to U.S. patent application Ser. No. 17/881,911 filed on Aug. 5, 2022, which claims the benefit of U.S. Provisional Application No. 63/350,741 filed on Jun. 9, 2022, the contents of which are incorporated by reference herein.

TECHNICAL FIELD

This disclosure relates generally to development assessment, such as using eye tracking devices for assessing developmental disorders in patients.

BACKGROUND

Developmental disorders such as autism spectrum disorders (ASD) affect nearly 14% of children in the United States. Diagnostic methods for conditions such as ASD vary considerably in terms of objective assessment tools and experience of the treatment providers. In some circumstances, the use of "best practice" tools provides rather poor sensitivity and specificity to the conditions, especially for toddlers or other young patients. Late diagnosis of developmental disabilities reduces effectiveness of treatments and often results in poor outcomes. Furthermore, treatment providers (e.g., pediatricians or other medical professionals) can often lack adequate tools for objectively measuring progress in these conditions, especially very early in a patient's life.

SUMMARY

The present disclosure describes methods, apparatus, and systems for assessing developmental disorders via eye tracking. For example, some systems described herein can be used in a diagnostic method for developmental, cognitive, social, or mental abilities or disabilities, including Autism Spectrum Disorder (ASD). The system may optionally be implemented with improved portable devices that achieve improved objective measurements and added convenience to treatment providers and the patient, such as a toddler or other young patient. In some embodiments, the system includes at least two separate portable computing devices, e.g., an operator-side portable device and at least one patient-side portable device that is integrated with an eye-tracking device. In particular examples described below, these portable devices can be differently equipped yet both wirelessly interact with a network-connected server platform to advantageously gather session data in a manner that is comfortable and less intrusive for the patient while also adding improved flexibility of control for the treatment provider. Optionally, the session data gathered via the patient-side portable device (e.g., using analysis of eye-tracking data generated in response to display of predetermined, age-appropriate visual stimuli) can be promptly analyzed for purposes of outputting at the operator-side portable device a result interface displaying at least one index based on objective factors.

One aspect of the present disclosure features a system for development assessment via eye tracking, including: a patient-side mobile computing device including a screen for presenting visual stimuli to a patient; an eye-tracking device mounted with the patient-side mobile computing device and oriented at a fixed positioned relative to the screen of the patient-side mobile computing device to collect eye-tracking data of the patient while the visual stimuli are presented to the patient on the screen of the patient-side mobile computing device; and an operator-side mobile computing device configured to present a user interface that controls activation of the visual stimuli presented to the patient on the screen of the patient-side mobile computing device.

In some embodiments, the operator-side computing mobile device and the patient-side mobile computing device are configured to communicate with each other via a wireless connection. In some embodiments, the operator-side mobile computing device and the patient-side mobile computing device are configured to wirelessly communicate with each other via a network-connected server. In some embodiments, the network-connected server includes a cloud computing system or a cloud server implemented in a cloud environment.

In some embodiments, the patient-side mobile computing device is configured to transmit data to the network-connected server, the data including eye-tracking data of the patient collected in a session while presenting the visual stimuli from a list of predetermined visual stimuli are presented to the patient.

In some embodiments, the patient-side mobile computing device is configured to automatically transmit the data in response to completion of all visual stimuli in the list of predetermined visual stimuli being presented in the session. In some embodiments, the patient-side mobile computing device is configured to transmit the data in response to receiving a completion indication from the operator-side mobile computing device or the network-connected server. In some embodiments, the operator-side mobile computing device or the network-connected server is configured to generate the completion indication in response to a determination that the session ends or receipt of an input indicating a completion of the session.

In some embodiments, the data includes information of the list of predetermined visual stimuli and the eye-tracking data of the patient collected in the session. In some embodiments, the patient-side computing mobile device is configured to transmit the data in two files that include a first file including the eye-tracking data of the patient and associated timestamp information and a second file including the information of the list of the visual stimuli. In some embodiments, the associated timestamp information for the eye-tracking data includes timestamps when the eye-tracking data are generated or collected, and the information of the list of predetermined visual stimuli includes timestamps when individual visual stimuli in the list are presented.

In some embodiments, the operator-side mobile computing device is configured to access a web portal in the network-connected server. In some embodiments, the operator-side mobile computing device is configured to communicate with one or more patient-side computing devices through the web portal in the network-connected server. In some embodiments, the user interface of the operator-side mobile computing device includes at least one of information of one or more patients associated with the operator, information of one or more patient-side computing devices associated with the operator, or information of the operator.

In some embodiments, the patient-side mobile computing device is configured to display connection information including an access code on the screen of the patient-side mobile computing device in response to connecting to the network-connected server. In some embodiments, the operator-side mobile computing device is configured to connect with the patient-side computing device by receiving an input of the connection information including the access code at the user interface. In some embodiments, the user interface of the operator-side mobile computing device presents a request for the connection information in response to receiving a selection of the patient-side mobile computing device among the one or more patient-side computing devices presented in the user interface.

In some embodiments, the operator-side mobile computing device is configured to present the user interface of an operator application running on one of the operator-side computing device or the network-connected server. In some embodiments, the operator application is configured to: present a user interface element for a start of desensitization in the user interface; and in response to a selection of the user interface element, transmit a command to the patient-side computing device to play visual desensitization information.

In some embodiments, the patient-side mobile computing device is configured to: in response to receiving the command, play the visual desensitization information on the screen of the patient-side mobile computing device to the patient, and control the eye-tracking device not to collect eye-tracking data of the patient while displaying the visual desensitization information on the screen.

In some embodiments, the operator application is configured to present the user interface for the operator to set up a session for the patient by selecting the patient among a list of patents or creating a profile for the patient, while the visual desensitization information is displayed on the screen of the patient-side mobile computing device.

In some embodiments, the operator application is configured to display in the user interface an instruction to adjust a position of the eye-tracking device relative to the patient or a position of the patient relative to the patient-side mobile computing device based on a sensed position of the eye-tracking device relative to at least one eye of the patient. In some embodiments, the sensed position is determined based on image data of the at least one eye of the patient captured by using an image acquisition device that is included with or adjacent to the eye-tracking device. In some embodiments, the sensed position is determined by the patient-side mobile computing device or the operator application.

In some embodiments, the operator application is configured to transmit a command to the patient-side mobile computing device for a calibration between the patient and the eye-tracking device, in response to one of: a selection of a user interface element for calibration in the user interface, or determining that a session for the patient is setup.

In some embodiments, the patient-side mobile computing device is configured to: in response to receiving the command, sequentially present one or more calibration targets at one or more predetermined locations of the screen of the patient-side mobile computing device, while capturing eye-tracking calibration data of the patient using the eye-tracking device.

In some embodiments, the patient-side mobile computing device is configured to: for each of the one or more calibration targets, process the captured eye-tracking calibration data of the patient to determine a position of a corresponding visual fixation of the patient for the calibration target; and compare the position of the corresponding visual fixation of the patient to a corresponding predetermined location where the calibration target is presented on the screen; determine whether the calibration target is calibrated for the patient based on a result of the comparison.

In some embodiments, the patient-side mobile computing device is configured to determine the calibration is completed in response to determining that the one or more calibration targets are calibrated. In some embodiments, the patient-side mobile computing device is configured to: in response to determining that a calibration target fails to be calibrated, re-calibrate the calibration target.

In some embodiments, the patient-side mobile computing device is configured to play desensitization information between presenting two adjacent calibration targets. In some embodiments, the operator application is configured to: in response to receiving an indication that the calibration is completed, start to validate the calibration. In some embodiments, the patient-side mobile computing device is configured to: in response to receiving a request for validating the calibration, present at least one additional calibration target on the screen, while capturing additional eye-tracking calibration data of the patient using the eye-tracking device; and process the captured additional eye-tracking calibration data of the patient to determine a position of a corresponding visual fixation of the patient for the at least one additional calibration target.

In some embodiments, the patient-side mobile computing device is configured to: compare the position of the corresponding visual fixation of the patient for the at least one additional calibration target to a corresponding predetermined location where the at least one additional calibration target is presented on the screen; and determine whether the calibration is validated based on a result of the comparison.

In some embodiments, the operator application is configured to: simultaneously present, in the user interface, the at least one additional calibration target at the corresponding predetermined location and at least one representation of the corresponding visual fixation of the patient at the determined position of the corresponding visual fixation of the patient for the at least one additional calibration target; and presenting a first user interface element for validation of the calibration and a second user interface element for re-calibration in the user interface.

In some embodiments, the operator application is configured to transmit a command to the patient-side computing device for data collection, in response to one of: a selection of a user interface element for staring the data collection, or determining that the calibration is completed or validated.

In some embodiments, the patient-side mobile computing device is configured to: in response to receiving the command, sequentially present a list of predetermined visual stimuli on the screen of the patient-side mobile computing device to the patient, while capturing eye-tracking data of the patient using the eye-tracking device.

In some embodiments, the patient-side mobile computing device is configured to: before presenting each of the list of predetermined visual stimuli, present a centering target on the screen of the patient-side mobile computing device to the patient. In some embodiments, the patient-side mobile computing device is configured to: perform a calibration of the patient to the eye-tracking device between presenting two adjacent visual stimuli among the list of predetermined visual stimuli. In some embodiments, the eye-tracking data collected in performing the calibration is used for at least one of recalibrating the eye-tracking data of the patient or for determining a calibration accuracy.

In some embodiments, the operator application is configured to present, in the user interface, at least one of a progress indicator that keeps updating throughout presenting the list of predetermined visual stimuli, a user interface element for skipping a visual stimulus among the list of predetermined visual stimuli, information of a visual stimulus already presented or being presented, or information of a visual stimulus to be presented.

In some embodiments, the network-connected server is configured to provide a diagnostic result of the patient based on the eye-tracking data of the patient, the diagnostic result includes at least one index value associated with developmental disorder. In some embodiments, the operator-side mobile computing device is configured to present the diagnostic result in the user interface.

In some embodiments, the visual stimuli are predetermined based on at least an age of the patient or a condition of the patient. In some embodiments, each of the visual stimuli includes at least one of a static visual stimulus, a dynamic visual stimulus, a pre-recorded visual stimulus, a pre-recorded audiovisual stimulus, a live visual stimulus, a live audiovisual stimulus, a two-dimensional stimulus, or a three-dimensional stimulus. In some embodiments, each of the visual stimuli is normed for eliciting specific eye movement responses with greater than 95% statistical confidence. In some embodiments, each of the visual stimuli is configured to elicit eye movement responses to discrete spatial-temporal locations with greater than 95% statistical confidence.

In some embodiments, the eye-tracking device is connected with the patient-side mobile computing device through a wired connection. In some embodiments, the eye-tracking device and the screen are housed together in a holder. In some embodiments, the patient-side mobile computing device includes a screen holder that retains the screen and the eye-tracking device in the fixed position relative to the screen.

In some embodiments, the eye-tracking device includes one or more eye-tracking units arranged in one or more locations adjacent to a peripheral of the screen. In some embodiments, at least one of the patient-side mobile computing device or the operator-side mobile computing device is a tablet computing device. In some embodiments, the operator-side computing device is configured to communicate with the patient-side mobile computing device via a bi-directional communication.

Another aspect of the present disclosure features an apparatus including: a patient-side computing device including a screen for presenting visual stimuli to a patient, and an eye-tracking device integrated with the patient-side computing device and configured to collect eye-tracking data of the patient while the visual stimuli are presented to the patient on the screen of the patient-side computing device. The patient-side computing device includes the patient-side computing device as described above.

Another aspect of the present disclosure features an apparatus including the operator-side computing device as described above.

Another aspect of the present disclosure features an apparatus including: at least one processor; and at least one non-transitory memory coupled to the at least one processor and storing programming instructions for execution by the at least one processor to perform operations including: establishing a wireless connection with a patient-side computing device that is integrated with an eye-tracking device; and presenting a user interface to communicate with the patient-side computing device for acquisition of eye-tracking data of a patient.

In some embodiments, the operations further include: accessing a web portal of a network-connected server, where the wireless connection is established through the web portal. In some embodiments, the operations further include: presenting in the user interface a diagnostic result based on the eye-tracking data of the patient.

Another aspect of the present disclosure features a computer-implemented method of development assessment via eye tracking. The computer-implemented method includes: initiating a session for a patient by establishing a communication with an operator-side computing device and a patient-side computing device, the patient-side computing device being integrated with an eye-tracking device; sequentially presenting a list of predetermined visual stimuli on a screen of the patient-side computing device to the patient, while collecting eye-tracking data of the patient using the eye-tracking device; and transmitting session data of the session to a network-connected server, the session data including the eye-tracking data of the patient collected in the session.

In some embodiments, at least one of the operator-side computing device or the patient-side computing device is a portable device. In some embodiments, establishing the communication includes: establishing a wireless connection between the operator-side computing device and the patient-side computing device.

In some embodiments, establishing the wireless connection between the operator-side computing device and the patient-side computing device includes: accessing, by the operator-side computing device, a web portal at the network-connected server; and in response to receiving a selection of the patient-side computing device in the web portal, wirelessly connecting the operator-side computing device to the patient-side computing device. In some embodiments, establishing the wireless connection between the operator-side computing device and the patient-side computing device includes: displaying, by the patient-side computing device, connection information on the screen of the patient-side computing device; and in response to receiving an input of the connection information by the operator-side computing device, establishing the wireless connection between the operator-side computing device and the patient-side computing device.

In some embodiments, the computer-implemented method further includes: after establishing the communication, displaying visual desensitization information on the screen of the patient-side computing device to the patient. In some embodiments, the computer-implemented method further includes: controlling the eye-tracking device not to collect eye-tracking data of the patient while displaying the visual desensitization information.

In some embodiments, the computer-implemented method further includes: while displaying the visual desensitization information, accessing, by the operator-side computing device, a web portal at the network-connected server to set up the session for the patient. In some embodiments, setting up the session includes one of selecting the patient among a list of patients or creating a profile for the patient at the network-connected server. In some embodiments, the computer-implemented method further includes determining a relative position between the eye-tracking device and at least one eye of the patient; and displaying an instruction to adjust a position of the eye-tracking device or a position of the patient on a user interface of the operator-side computing device.

In some embodiments, the computer-implemented method further includes: in response to determining that the relative location at least one eye of the patient is at a predetermined location in a detection area of the eye-tracking device, determining that the patient is aligned with the eye-tracking device.

In some embodiments, the computer-implemented method further includes: calibrating the patient to the eye-tracking device by displaying one or more calibration targets on the screen of the patient-side computing device to the patient.

In some embodiments, calibrating the patient to the eye-tracking device includes: sequentially presenting each of the one or more calibration targets at a corresponding predetermined location of the screen of the patient-side computing device, while capturing eye-tracking calibration data of the patient using the eye-tracking device; for each of the one or more calibration targets, processing the captured eye-tracking calibration data of the patient to determine a position of a corresponding visual fixation of the patient for the calibration target; comparing the position of the corresponding visual fixation of the patient with the corresponding predetermined location where the calibration target is presented; and determining whether the calibration target is calibrated to the eye-tracking device based on a result of the comparing.

In some embodiments, calibrating the patient to the eye-tracking device further includes: in response to determining that a deviation between the position of the corresponding visual fixation of the patient with the corresponding predetermined location is smaller than or equal to a predetermined threshold, determining that the calibration target is calibrated and displaying a next calibration target, or in response to determining that the deviation is greater than the predetermined threshold, determining that the calibration target fails to be calibrated and re-displaying the calibration target for calibration.

In some embodiments, the computer-implemented method further includes: after calibrating the patient to the eye-tracking device, validating the calibration with one or more new calibration targets. In some embodiments, validating the calibration includes: sequentially presenting each of the one or more new calibration targets at a corresponding predetermined location of the screen of the patient-side computing device, while capturing eye-tracking calibration data of the patient using the eye-tracking device; and processing the captured eye-tracking calibration data of the patient to determine a position of a corresponding visual fixation of the patient for each of the one or more new calibration targets.

In some embodiments, validating the calibration includes: simultaneously presenting, on a user interface of the operator-side computing device, the one or more new calibration targets at one or more corresponding predetermined locations and representations of the one or more corresponding visual fixations of the patient at the determined one or more positions; and in response to receiving an indication to validate a result of the calibrating, determining that the calibration is validated, or in response to receiving an indication to invalidate the result of the calibrating, starting to re-calibrate the patient to the eye-tracking device.

In some embodiments, validating the calibration includes: determining a number of new calibration targets that each passes a calibration based on the position of the corresponding visual fixation of the patent and the corresponding predetermined position; and if the number or an associated percentage is greater than or equal to a predetermined threshold, determining that the calibration is validated, or if the number or the associated percentage is smaller than the predetermined threshold, determining that the calibration is invalidated and starting to re-calibrate the patient to the eye-tracking device.

In some embodiments, sequentially presenting the list of predetermined visual stimuli on the screen of the patient-side computing device to the patient includes: before presenting each of the list of predetermined visual stimuli, presenting a centering target on the screen of the patient-side computing device to the patient.

In some embodiments, sequentially presenting the list of predetermined visual stimuli on the screen of the patient-side computing device to the patient includes: performing a calibration of the patient to the eye-tracking device between presenting two adjacent visual stimuli among the list of predetermined visual stimuli, where the eye-tracking data collected in performing the calibration is used for at least one of calibrating the eye-tracking data of the patient or for determining a calibration accuracy.

In some embodiments, the computer-implemented method further includes: presenting, on a user interface of the operator-side computing device, at least one of: a progress indicator that keeps updating throughout presenting the list of predetermined visual stimuli, information of visual stimuli already presented or being presented, information of visual stimuli to be presented, or a user interface element for skipping a visual stimulus among the list of predetermined visual stimuli.

In some embodiments, transmitting the session data of the session to the network-connected server includes: automatically transmitting, by the patient-side computing device, the session data of the session to the network-connected server, in response to one of: determining a completion of presenting the list of predetermined visual stimuli on the screen, or receiving a completion indication of the session from the operator-side computing device.

In some embodiments, the session data includes information related to the presented list of predetermined visual stimuli. In some embodiments, the information related to the presented list of predetermined visual stimuli includes names of presented predetermined visual stimuli and associated timestamps when the predetermined visual stimuli are presented.

In some embodiments, the session data includes the eye-tracking data and associated timestamps when the eye-tracking data are generated or collected. In some embodiments, the session data is stored in a first file storing the eye-tracking data of the patient and a second file storing the information related to the presented list of predetermined visual stimuli.

Another aspect of the present disclosure features a computer-implemented method for development assessment using eye-tracking data by a network-connected server. the computer-implemented method includes: receiving session data of multiple sessions, the session data of each session including eye-tracking data of a corresponding patient in the session; processing the session data of the multiple sessions in parallel to generate processed session data for the multiple sessions; and for each session of the multiple sessions, analyzing the processed session data of the session based on corresponding reference data to generate an assessment result for the corresponding patient in the session.

In some embodiments, the computer-implemented method further includes: loading the corresponding reference data for the multiple sessions in parallel with processing the session data of the multiple sessions.

In some embodiments, the network-connected server includes a plurality of processing cores. Processing the session data of the multiple sessions in parallel includes using a first plurality of processing cores to process the session data of the multiple sessions in parallel and using a second, different plurality of processing cores to load the corresponding reference data for the multiple sessions, a number of the first plurality of processing cores being larger than a number of the second plurality of processing cores.

In some embodiments, analyzing the processed session data of the multiple sessions based on the loaded corresponding reference data for the multiple sessions includes: using the plurality of processing cores including the first plurality of processing cores and the second plurality of processing cores.

In some embodiments, analyzing the processed session data of the multiple sessions based on the loaded corresponding reference data for the multiple sessions includes at least one of: comparing the processed session data of the session to the corresponding reference data, inferring the assessment result for the corresponding patient from the processed session data using the corresponding reference data, or using at least one of a statistical model, a machine learning model, or an artificial intelligence (AI) model. In some embodiments, the corresponding reference data includes historical eye-tracking data or results for patients having substantially same age or condition as the corresponding patient.

In some embodiments, the computer-implemented method further includes: generating the assessment result based on previous session data of the corresponding patient. In some embodiments, the computer-implemented method includes: for each session of the multiple session, assigning a respective container for the session, and, in the respective container, processing the session data of the session and analyzing the processed session data of the session based on the corresponding model data to generate the assessment result for the corresponding patient in the session.

In some embodiments, the eye-tracking data is associated with a list of predetermined visual stimuli presented to the patient while the eye-tracking data is collected in the session, and where the session data includes information associated with the list of predetermined visual stimuli in the session.

In some embodiments, the computer-implemented method further includes: linking the eye-tracking data of the session with the list of predetermined visual stimuli in the session. In some embodiments, linking the eye-tracking data of the session with the list of predetermined visual stimuli in the session includes: in the respective container, breaking up the eye-tracking data into multiple portions based on the information associated with the list of predetermined visual stimuli, each portion of the eye-tracking data being associated with one of a respective predetermined visual stimulus or a corresponding calibration.

In some embodiments, processing the session data of the session includes processing portions of the eye-tracking data associated with respective predetermined visual stimulus based on information of the respective predetermined visual stimulus.

In some embodiments, the computer-implemented method further includes: in the respective container, recalibrating portions of eye-tracking data associated with respective predetermined visual stimulus based on at least one portion of eye-tracking data associated with the corresponding calibration.

In some embodiments, the computer-implemented method further includes: in the respective container, determining a calibration accuracy using at least one portion of eye-tracking data associated with the corresponding calibration and a plurality of predetermined locations where a plurality of calibration targets are presented in the corresponding calibration.

In some embodiments, receiving the session data of the multiple sessions includes: receiving, through a web portal, the session data of the multiple sessions from a plurality of computing devices associated with corresponding entities. In some embodiments, the computer-implemented method further includes: in response to receiving session data of a session, adding a file pointer for the session data of the session in a processing queue to be processed. In some embodiments, the computer-implemented method further includes: storing the session data of the session using the file pointer for the session in a database; and retrieving the session data of the session from the database using the file pointer for the session.

In some embodiments, the computer-implemented method further includes: for each entity, storing session data from one or more computing devices associated with the entity in a respective repository. In some embodiments, the respective repository for the entity includes at least one of: information of the entity, information of one or more operators or operator-side computing devices associated with the entity, information of one or more patient-side computing devices associated with the entity, information of one or more sessions conducted in the entity, information of one or more patients associated with the entity, or history information of the respective repository.

In some embodiments, the respective repository is included in a NoSQL database. In some embodiments, the respective repository is isolated from one or more other repositories and inaccessible by one or more other entities.

In some embodiments, the computer-implemented method further includes: dynamically adjusting resources of the network-connected server based on a number of computing devices that access the network-connected server.

In some embodiments, the computer-implemented method further includes: replicating data of a first data center to a second data center; and in response to determining that the first data center is inaccessible, automatically directing traffic to the second data center. In some embodiments, each of the first data center and the second data center includes at least one of a web portal accessible for the operator-side computing device, an operator application, or an application layer for data processing and data analysis.

In some embodiments, the computer-implemented method further includes: storing same data in multiple data centers, where the data includes application data for entities and information associated with the eye-tracking data.

In some embodiments, the computer-implemented method further includes: associating the generated assessment result with the corresponding patient in the session; and generating an assessment report for the corresponding patient.

In some embodiments, the computer-implemented method further includes: outputting assessment results or assessment reports to be presented at a user interface of the operator-side computing device. In some embodiments, the assessment report includes at least one of: information of the corresponding patient, information of an entity performing the session for the corresponding patient, information of a calibration accuracy in the session, information of session data collection, or the assessment result for the corresponding patient.

In some embodiments, the assessment result indicates a likelihood that the corresponding patient has a developmental, cognitive, social, or mental disability or ability. In some embodiments, the assessment result indicates a likelihood that the corresponding patient has an Austin Spectrum Disorder (ASD) or a non-ASD. In some embodiments, the assessment result includes a respective score for each of one or more of: social disability index, verbal ability index, nonverbal ability, social adaptiveness index, and social communication index.

In some embodiments, the assessment result includes at least one of: a visualization of the eye-tracking data overlaid on corresponding visual stimulus stills from socially relevant moments, an animation visualizing the eye-tracking data overlaid on corresponding visual stimulus stills from socially relevant moments, a visualization of aggregated reference data from a plurality of reference patients matched with a corresponding patient on one or more patient attributes, or annotations describing at least one of a visual stimulus content or eye-gaze patterns.

In some embodiments, the corresponding patient has an age in a range from 5 months to 7 years, including an age in a range from 5 months to 43 months or 48 months, an age in a range from 16 to 30 months, an age in a range from 18 months to 36 months, an age in a range from 16 months to 48 months, or an age in a range from 16 months to 7 years.

Another aspect of the present disclosure features a system, including: at least one processor; and one or more memories storing instructions that, when executed by the at least one processor, cause the at least one processor to perform a computer-implemented method as described herein.

Another aspect of the present disclosure features one or more non-transitory computer-readable media storing instructions that, when executed by at least one processor, cause the at least one processor to perform a computer-implemented method as described herein.

One or more of the embodiments described herein can achieve a number of technical effects and advantages. In a first example, some embodiments can provide a convenient, miniaturized, and effective computing system for advantageously gathering eye-tracking data and subsequently communicating such data for analysis and diagnostic results. The computing system may include at least two separate portable computing devices, e.g., an operator-side portable device and at least one patient-side portable device that is integrated with an eye-tracking device. These portable devices can be equipped differently (different peripherals or equipment, different user interfaces, and the like) and can be wirelessly connected, without physical connection, to one another or to a network-connected server platform (which, in turn, provides communication between the operator-side portable device and the patient-side portable device). For example, an operator may use the operator-side portable device to calibrate the eye-tracking device with a patient and to control playing the predetermined visual stimuli on the patient-side portable device for obtaining eye-tracking data of the patient with the eye-tracking device. Once a session is completed, the patient-side portable device can transmit session data, e.g., detected eye-tracking data and information of the played visual stimuli, to a cloud server for data storage, processing, and analysis. The cloud server can be remotely connected with these portable devices, e.g., via a network.

In a second example, some implementations of the computing system described below can have a smaller form factor (e.g., compared to larger seat-mounted computer apparatus), and can be more readily moved and relocated—thereby improving convenience for the patient, the treatment provider, or both. The computing system also may allow more flexibility to both the operator and the patient who can more easily position themselves in suitable locations during setup and data collection. Moreover, in some embodiments detailed below that use two separate portable computing devices, e.g., tablets, the system can advantageously impose lower requirements on the computing devices themselves and provides more flexibility in implementing different functions in the two separate computing devices. Further, in some methods described below, the patient (e.g., toddler or other young patient) can be held by/seated with a caregiver (e.g., a parent) during the display of the visual stimuli for improved comfort and accurate eye-tracking data acquisition at patient-side portable device, yet the treatment provider (carrying the operator-side portable device to control playback of the predetermined visual stimuli) can contemporaneously select a position spaced apart from the patient and caregiver to thereby reduce distractions for the patient. Further, the technologies enable the treatment provider to use the operator-side portable device to log in a web portal of the cloud server for device management, patient management, and data management. For example, through the web portal of the cloud server, the treatment provider can use the operator-side portable device to communicate with multiple patient-side portable devices for eye-tracking data acquisitions of multiple patients in multiple sessions, which can greatly improve work efficiency and reduce the treatment provider's workload. Moreover, a web-based operator application can run on the cloud server and provide a user interface for the treatment provider to select a patient-side portable device for connection, perform calibration, validation, and session data acquisition. The web-based operator operation can be maintained or updated at the cloud server, which can be more convenient, more efficient with lower cost than installing operator applications in individual operator-side portable devices. Further, an operator-side portable device can be paired with multiple patient-side portable devices, which can simplify an overall system, reduce the system cost, and improve the system performance.

In a third example, some embodiments detailed below can advantageously support services to a large number of treatment providers across a variety of geographic locations. In some embodiments, the cloud server is implemented in a centralized cloud environment and can communicate with multiple computing devices or systems as described above. The cloud server can utilize a Software as a Service (SaaS) model by providing subscription-based diagnostic services to treatment providers. The centralized cloud environment can provide more flexibility to expand a capability of the cloud server. For example, the cloud server can implement a multi-tenant architecture. A tenant can be a single healthcare organization that includes, but is not limited to, an autism center, healthcare facility, specialist, physician, or a clinical study. Resources of the cloud server can be dynamically managed based on a total number of tenants and expected average workload, e.g., how many tenants are accessing the cloud server at a given time point. The cloud server can adopt horizontal scaling techniques such as auto-scaling to handle spikes in the resource workload.

Additionally, in a fourth example, some versions of the technologies detailed below can provide high efficient and speedy diagnostic results to treatment providers. As noted above, a computing system, e.g., the patient-side portable device, can automatically upload session data to the cloud server once a session is completed. The cloud server can be also configured to automatically receive, process, and analyze session data from multiple computing systems, without human intervention. Moreover, the cloud server can process and analyze session data of a number of sessions from a large number of computing systems in parallel, which can greatly improve session processing speed and provide diagnostic results in a short period of time, e.g., within a 24-hour window. In some embodiments, the cloud server can deploy a respective container for each session, and the respective container can include a corresponding data processing module and a data analysis module. In this way, once session data of a session is uploaded, the session data of the session can be processed and analyzed using its own container (e.g., its own instance of data processing and data analysis). In some embodiments, while session data of multiple sessions are being processed in corresponding containers, e.g., using a majority of processing units (or cores) in the cloud server, model data for analyzing the processed session data can be pre-loaded into the corresponding containers in parallel, e.g., using the remaining or a minority of the processing units in the cloud server. Then, all of the processed session data and the loaded model data can be analyzed in the corresponding containers in parallel, e.g., using the total number of processing units in the cloud server. The technologies enable automatization and parallelization in multiple ways, which can greatly improve the speed of session data processing and analysis and provide speedy diagnostic results in the short period of time, e.g., within a 24-hour window. The parallelization can also make the cloud server be more efficient in resource utilization, which can further improve the system performance.

In a fifth example, some embodiments described herein can also provide improved accuracy of diagnostic results for patients based on high efficient data analysis. A large amount of model data, including data related to patients at similar ages, similar backgrounds, and/or similar situations, can be used with processed session data for a patient to generate a diagnostic result for the patient, e.g., using comparison or inference via statistical models, algorithms, artificial intelligence (AI) models such as machine learning or artificial neural network models, which can greatly increase accuracy of the diagnostic results.

In a sixth example, some versions of the technologies described herein can enable privacy, confidentiality, and security of treatment provider data. In some embodiments, the cloud server stores different types of data, e.g., related to organization, user, session, patient, and device, as application data or documents in a database (e.g., a NoSQL database). Different tenants can have their own databases, which can isolate data among the tenants and prevent others from accessing their own data, thereby improving data integrity and confidentiality. The tenants can share a single instance of an application in the cloud server, or each tenant can get their own instances of the application.

In a seventh example, some embodiments described herein can ensure high availability of services to treatment providers, such that the treatment providers can access their services regardless of any outages in the cloud server. The cloud server can be hosted in a cloud environment that can have built-in high availability or configurable high availability, e.g., using high-availability service level agreements or through use of geo-redundancy. As an example, the technologies can replicate a data center in different physical locations. When a data center goes down, traffic can be automatically redirected to a replicated data center. The process can be seamless, and the treatment providers may be unaware of the switch to the replicated data center. In some embodiments, the data center includes web portals accessible to the treatment providers/users, and data processing and data analysis modules. Additionally, the technologies can replicate databases in multiple locations. The databases can include application data and raw eye-tracking data, processed data, data analysis, diagnostic results, and/or assessment reports.

In an eighth example, some versions of the technologies described herein can provide centralized data entry (such as patient identifiers and metadata to augment eye-tracking data), e.g., in the cloud server, which can reduce workloads of treatment providers, reduce human errors, and ensure data accuracy. In some embodiments, the technologies provide bi-directional communications among different devices or systems. Compared to one-way communication that requires data to be entered multiple times in the separate devices or systems, the bi-directional communication can reduce data entry for the treatment providers and can enable autonomous data transmission.

In a ninth example, some embodiments described herein can also provide secure communications between different devices and systems. For example, communication between an on-premise computing system (including an operator-side portable device and patient-side portable device) and the cloud server can use hypertext transfer protocol secure (HTTPS) communication, through which information is encrypted to protect both privacy and integrity of the information. Communication between the patient-side portable device and the operator-side portable device can be done using WebSocket communication, e.g., using secure implementation of WebSocket known as WebSocket Secure (WSS). The Websocket communication can also provide bi-directional communication between the devices, which allows the operator-side portable device to control the patient-side portable device while receiving information from the patient-side portable device at the same time.

In some implementations, the technologies can be utilized to provide a diagnosis (based upon objective data) for young patients at early ages where such diagnosis and intervention can achieve the most impact. Additionally, the technologies described herein can be used to monitor the risk severity, which can provide insight into the severity at an earlier age and provide confirmation of severity and disorder status over time. The technologies can provide an immediate and sound baseline of a child's status and progress to jumpstart individualized therapy for the child. The technologies can provide objective baseline and confirmatory diagnoses to inform individualized treatment plans and minimize inefficiencies and costs associated with patient measures and lengthy evaluations. The technologies can reduce variability in care by providing clear standards and measures of progress, and can provide clear and quantified standards that can be administered and understood regardless of provider/staff skills. The technologies can create access among underserved and under resourced populations, and be used in a variety of care settings at a price point that is both affordable and less time consuming than current assessment alternatives.

The technologies implemented herein can be used to provide earlier identification and assessment of the risk of developmental, cognitive, social, verbal or non-verbal abilities, or mental abilities or disabilities in patients, for example, by measuring visual attention to social information in the environment relative to normative, age-specific benchmarks. The patients can have an age in a range from 5 months to 7 years, e.g., from 16 months to 7 years, from 12 months to 48 months, from 16 to 30 months, or from 18 months to 36 months.

According to certain aspects, changes in visual fixation of a patient over time with respect to certain dynamic stimuli provides a marker of possible developmental, cognitive, social, or mental abilities or disorders (such as ASD) of the patient. A visual fixation is a type of eye movement used to stabilize visual information on the retina, and generally coincides with a person looking at or "fixating" upon a point or region on a display plane. In some embodiments, the visual fixation of the patient is identified, monitored, and tracked over time through repeated eye-tracking sessions and/or through comparison with model data based on a large number of patients in similar ages and/or backgrounds. Data relating to the visual fixation is then compared to relative norms to determine a possible increased risk of such a condition in the patient. A change in visual fixation (in particular, a decline or increase in visual fixation to the image of eyes, body, or other region-of-interest of a person or object displayed on a visual stimulus) as compared to similar visual fixation data of typically-developing patients or to a patient's own, prior visual fixation data provides an indication of a developmental, cognitive, or mental disorder. The technologies can be applied to quantitatively measure and monitor symptomatology of the respective ability or disability and, in certain cases, provide more accurate and relevant prescriptive information to patients, families, and service providers. According to additional aspects, the technologies can be used to predict outcome in patients with autism (thus providing prescriptive power) while also providing similar diagnostic and prescriptive measures for global developmental, cognitive, social, or mental ability or disabilities.

As detailed below, the technologies described herein for the detection of developmental, cognitive, social, or mental disabilities can be applicable to the detection of conditions including, but not limited to, expressive and receptive language developmental delays, non-verbal developmental delays, intellectual disabilities, intellectual disabilities of known or unknown genetic origin, traumatic brain injuries, disorders of infancy not otherwise specified (DOI-NOS), social communication disorder, and autism spectrum disorders (ASD), as well as such conditions as attention deficit hyperactivity disorder (ADHD), attention deficit disorder (ADD), post-traumatic stress disorder (PTSD), concussion, sports injuries, and dementia.

It is appreciated that methods in accordance with the present disclosure may include any combination of the embodiments described herein. That is, methods in accordance with the present disclosure are not limited to the combinations of embodiments specifically described herein, but also include any combination of the embodiments provided.

The details of one or more embodiments of the present disclosure are set forth in the accompanying drawings and the description below. Other embodiments and advantages of the present disclosure will be apparent from the description and drawings, and from the claims.

BRIEF DESCRIPTION OF THE DRAWINGS

FIG. 5 illustrates example session data including (a) movie playlist data; (b) eye-tracking sensor data, according to one or more embodiments of the present disclosure.

Like reference numbers and designations in the various drawings indicate like elements. It is also to be understood that the various exemplary implementations shown in the figures are merely illustrative representations and are not necessarily drawn to scale.

DETAILED DESCRIPTION

The present disclosure describes systems, devices, and methods for detection and assessment of developmental, cognitive, social, or mental abilities or disabilities, including Autism Spectrum Disorder (ASD), in patients using eye-tracking data generated in response to display of specific predetermined visual stimuli (e.g., one or more videos) to the patients.

To provide an overall understanding of the systems, devices, and methods described herein, certain illustrative embodiments will be described. It will be understood that such data, if not indicating measures for a disorder, may provide a measure of the degree of typicality of normative development, providing an indication of variability in typical development. Further, all of the components and other features outlined below may be combined with one another in any suitable manner and may be adapted and applied to systems outside of medical diagnosis. For example, the interactive visual stimuli of the present disclosure may be used as a therapeutic tool. Further, the collected data may yield measures of certain types of visual stimuli that patients attend to preferentially. Such measures of preference have applications both in and without the fields of medical diagnosis and therapy, including, for example advertising or other industries where data related to visual stimuli preference is of interest.

Example Environments and Systems

Figure 1:
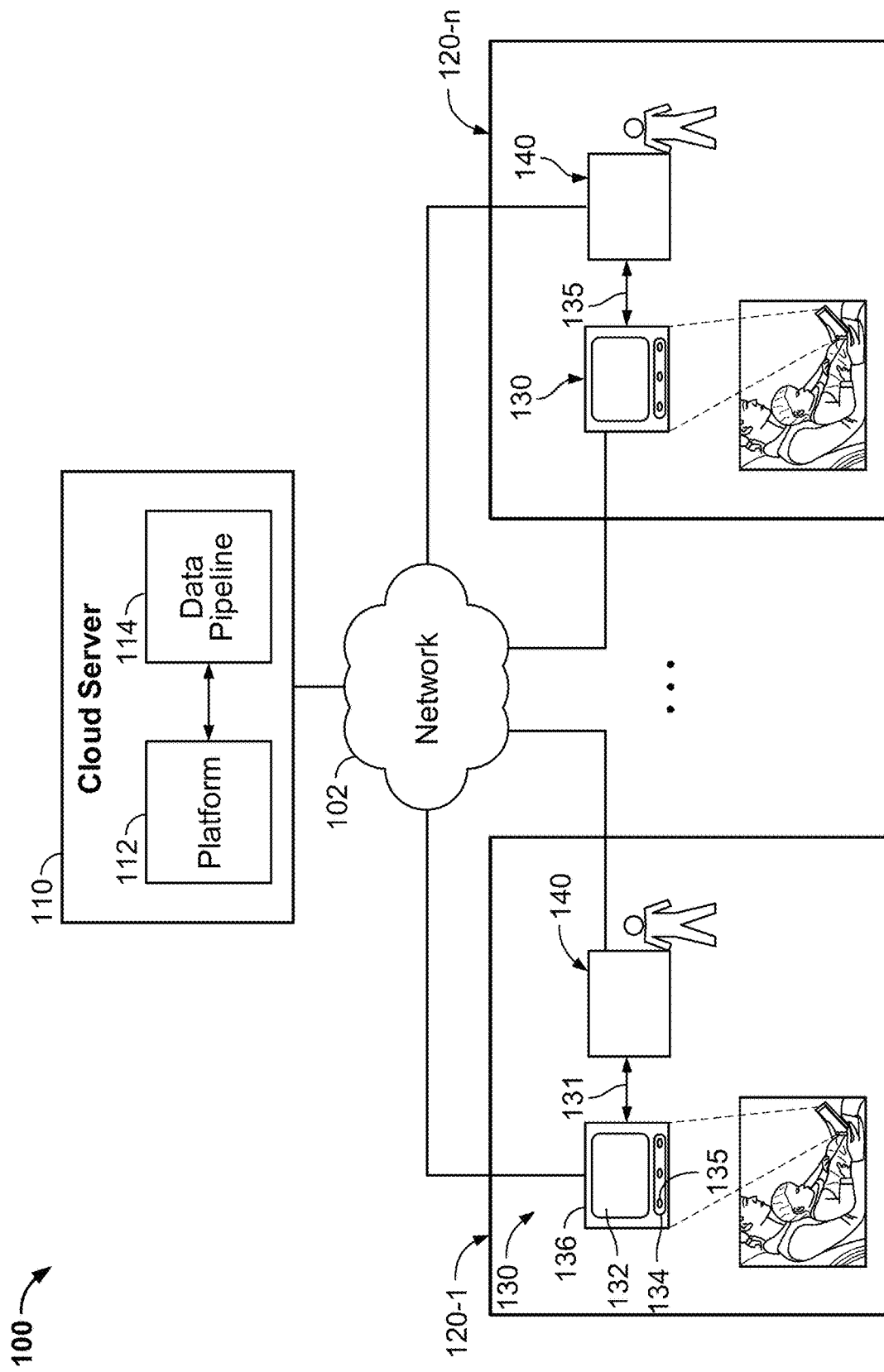
FIG. 1 is a block diagram of an example environment for assessing developmental disorders via eye tracking, according to one or more embodiments of the present disclosure.

FIG. 1 is a block diagram of an example environment 100 for assessing developmental disorders via eye tracking, according to one or more embodiments of the present disclosure. The environment 100 involves a cloud server 110 and a plurality of computing systems 120-1, . . . , 120-n (referred to generally as computing systems 120 or individually as computing system 120) that communicate via a network 102. The cloud server 110 can provide developmental disorder assessment or diagnostic services to a number of users (e.g., treatment providers). A treatment provider can use a corresponding computing system 120 to conveniently and reliably collect data for patients in sessions (e.g., procedures associated with collecting data) of any age, from newborns to the elderly, with example embodiments described below that are particularly suited for toddlers or other young patients. The data collected in a session (or session data) can include eye-tracking data generated in response to display of specific predetermined visual stimuli (e.g., one or more videos) to the patients. The computing system 120 can securely transmit the session data to the cloud server 110, and the cloud server 110 can store, process, and analyze the session data for the diagnosis of ASD or other cognitive, developmental, social or mental abilities or disabilities for the patients, and provide diagnostic results or reports to the treatment providers in a highly secure, robust, speedy, and accurate manner, as discussed with further details below, A treatment provider can be a single healthcare organization that includes, but is not limited to, an autism center, a healthcare facility, a specialist, a physician, or a clinical study. The healthcare organization can provide developmental assessment and diagnosis, clinical care, and/or therapy services to patients. As illustrated in FIG. 1, a patient (e.g., an infant or a child) can be brought by a caregiver (e.g., a parent) to the healthcare facility. An operator (e.g., a specialist, a physician, a medical assistant, a technician, or other medical professional in the healthcare facility) can use the computing system 120 to collect, e.g., non-invasive, eye-tracking data from the patient while he or she watches visual stimuli (e.g., dynamic visual stimuli, such as movies) depicting common social interactions (e.g., dyadic or triadic interactions). The stimuli displayed to the patient for purposes of data collection can be specific for the patient, e.g., based on age and condition of the patient. The stimuli can be any suitable visual image (whether static or dynamic), including movies or videos, as well as still images or any other visual stimuli. It will be understood that movies or videos are referenced solely by way of example and that any such discussion also applies to other forms of visual stimuli.

In some embodiments, as illustrated in FIG. 1, the computing system 120 includes at least two separate computing devices 130 and 140, e.g., an operator-side computing device 140 and at least one patient-side computing device 130. Optionally, the two computing devices 130 and 140 can be wirelessly connected, e.g., via a wireless connection 131, without physical connection. The wireless connection 131 can be through a cellular network, a wireless network, Bluetooth, a near-field communication (NFC) or other standard wireless network protocol. In some embodiments, the patient-side computing device 130 is configured to connect to the operator-side computing device 140 through a wired connection such as universal serial bus (USB), e.g., when the wireless connection 131 fails.

In some cases, the two computing devices 130 and 140 communicate with each other by separately communicating with the cloud server 110 via the network 102, and the cloud server 110, in turn, provides communication between the operator-side computing device 140 and the patient-side computing device 130. For example, as discussed with further details in FIGS. 4A-4B, an operator can log in a web portal running on the cloud server 110 for device management, patient management, and data management, e.g., through a web-based operator application. The operator can use the operator-side computing device 140 (e.g., a tablet) to communicate with multiple patient-side portable devices 130, e.g., in a same medical facility, for eye-tracking data acquisitions of multiple patients in multiple sessions, which can greatly simplify the computing system 120, reduce the system cost, improve work efficiency, and reduce the operator's workload.

Figure 12:
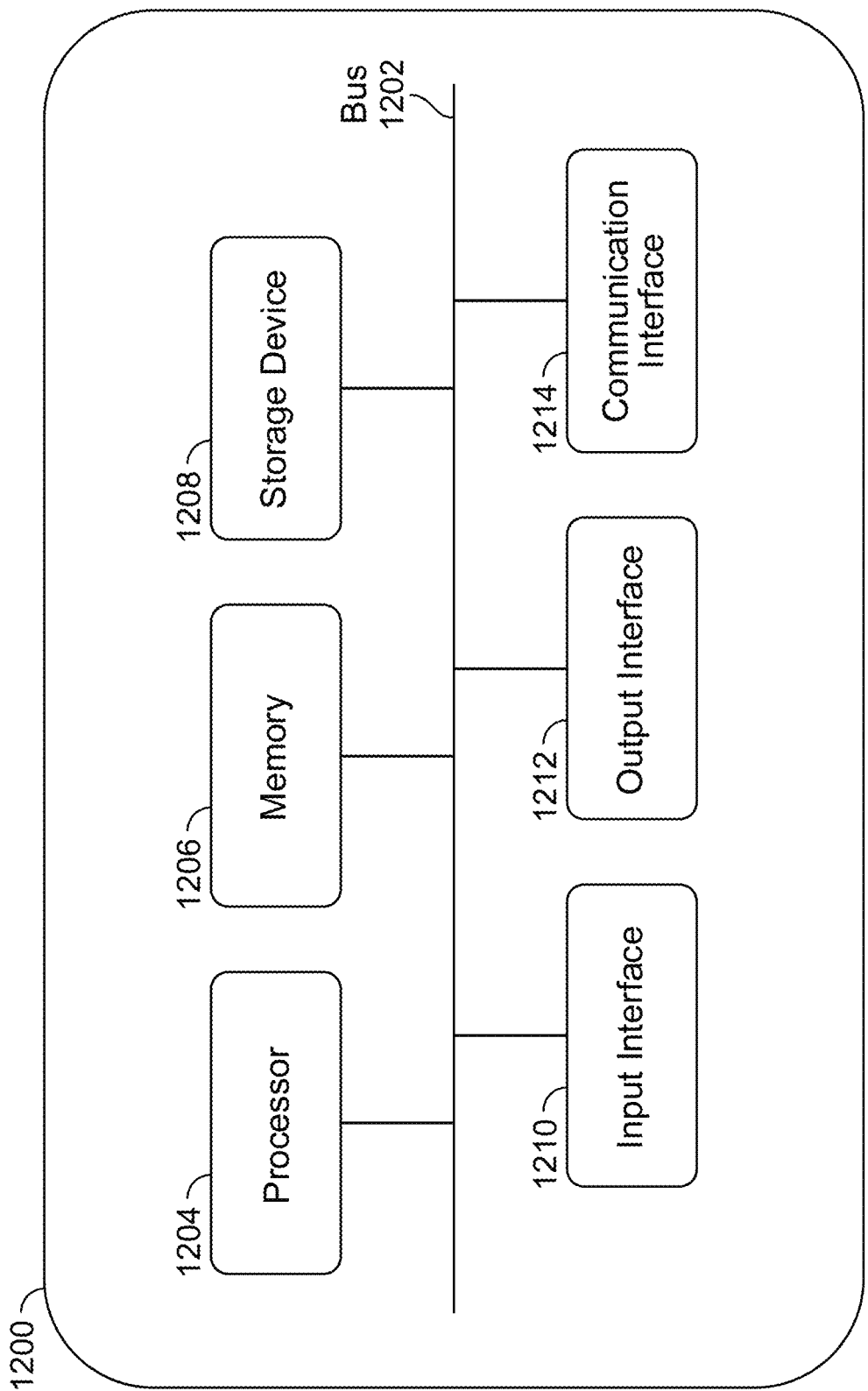
FIG. 12 illustrates an architecture for a computing device, according to one or more embodiments of the present disclosure.

The computing device 130, 140 can include any appropriate type of device such as a tablet computing device, a camera, a handheld computer, a portable device, a mobile device, a personal digital assistant (PDA), a cellular telephone, a network appliance, a smart mobile phone, an enhanced general packet radio service (EGPRS) mobile phone, or any appropriate combination of any two or more of these data processing devices or other data processing devices. As an example, FIG. 12 illustrates an architecture for a computing device, which can be implemented as the computing device 130 or 140.

At least one of the computing device 130 or the computing device 140 can be a portable device, e.g., a tablet device. In some cases, both computing devices 130, 140 are portable and wirelessly connected with each other. In such a way, the computing system 120 can be more easily moved and relocated, and allows more flexibility for the operator to select his or her position relative to the patient. For example, the operator (carrying the operator-side computing device 140) is not physically tethered to the patient-side computing device 130 and can easily position himself or herself in an optimal location (e.g., away from the patient's immediate field of view) during setup and data collection. Further, the patient (e.g., a toddler or other child) can be carried by a caregiver (e.g., a parent) in a more suitable location and in a more comfortable way, which may enable the patient to be more engaged in the played visual stimuli for effective and accurate eye-tracking data acquisition. The patient-side computing device 130 can be carried by the caregiver or arranged (e.g., adjustably) in front of the patient and the caregiver.

As illustrated in FIG. 1, the patient-side computing device 130 includes a screen 132 (e.g., a display screen) for displaying or presenting visual stimuli to the patient. The patient-side computing device 130 can also include an eye-tracking device 134 or be integrated with an eye-tracking device 134 in a same housing 136. In some embodiments, the patient-side computing device 130 integrated with the eye-tracking device 134 together can be referred to as an eye-tracking console or an eye-tracking system.

The eye-tracking device 134 can be connected to the patient-side computing device 130 via a wired connection, e.g., using an USB cable or an electrical wire or using electrical pins. In some cases, the eye-tracking device 134 is configured to be connected to the patient-side computing device 130 via a wireless connection, e.g., Bluetooth or NFC. The eye-tracking device 134 can be arranged in a suitable position with respect to the screen 132 and/or the patient, where the eye-tracking device 134 can capture eye movement of the patient while watching the visual stimuli, while also minimizing visual distractions from the patient's field-of-view.

As illustrated in FIG. 1, the eye-tracking device 134 can include one or more eye-tracking units (or sensors) 135 arranged under the bottom of the screen 132. The one or more eye-tracking units 135 can be arranged on one or more sides of the screen 132, on top of the screen 132, and/or around the screen 132. The one or more eye-tracking units 135 can be mechanically mounted to the patient-side computing device 130 at a location adjacent to a periphery of the screen 132. For example, the patient-side computing device 130 can include the screen 132 and a screen holder structure that retains the eye-tracking device 134 in a fixed, predetermined location relative to the screen 132. In some embodiments, the eye-tracking device 134 includes a first eye-tracking unit configured to capture or collect eye movement of a left eye of a patient and a second eye-tracking unit configured to capture or collect eye movement of a right eye of the patient. The eye-tracking device 134 can further include a third eye-tracking unit configured to capture positions of the eyes of the patient or an image acquisition unit (e.g., a camera) configured to capture an image of the eyes of the patient.

An eye-tracking unit includes a sensor that can detect a person's presence and follow what he/she is looking at in real-time or measure where the person is looking or how the eyes react to stimuli. The sensor can convert eye movements of the person into a data stream that contains information such as pupil position, the gaze vector for each eye, and/or gaze point. In some embodiments, an eye-tracking unit includes a camera (e.g., an infrared-sensitive camera), an illumination source (e.g., infrared light (IR) illumination), and an algorithm for data collection and/or processing. The eye-tracking unit can be configured to track pupil or corneal reflection or reflex (CR). The algorithm can be configured for pupil center and/or cornea detection and/or artifact rejection.

As there may be variations in eye size, fovea position and general physiology that can be accommodated for each individual, before using an eye-tracking unit to collect eye-tracking data for a participant (e.g., a patient), an eye-tracking unit can be first calibrated. In the calibration, a physical position of an eye is algorithmically associated with a point in space that the participant is looking at (e.g., gaze). Gaze position can be a function of the perception of the participant. In some embodiments, a calibration involves a participant looking at fixed, known calibration targets (e.g., points) in a visual field. Calibrations can include a single, centered target, or 2, 5, 9, or even 13 targets. The algorithm can create a mathematical translation between eye position (minus CR) and gaze position for each target, then create a matrix to cover the entire calibration area, e.g., with interpolation in between each target. The more targets used, the higher and more uniform the accuracy can be across the entire visual field. The calibration area defines the highest accuracy part of the eye-tracking unit's range, with accuracy falling if the eye moves at an angle larger than the targets used.

In some embodiments, an eye-tracking unit is capable of performing self-calibration, e.g., by creating models of the eye and passively measuring the characteristics of each individual. Calibration can also be done without the participant's active cooperation by making assumptions about gaze position based on content, effectively "hiding" calibration targets in other visual information. In some embodiments, no calibration is performed for an eye-tracking unit if useful data can be taken from raw pupil position, e.g., using a medical vestibulo-ocular reflex (VOR) system or a fatigue monitoring system.

In some cases, a validation can be performed to measure the success of the calibration, e.g., by showing new targets and measuring the accuracy of the calculated gaze. Tolerance for a calibration accuracy can depend on an application of the eye-tracking unit. For example, an error of between 0.25 and 0.5 degrees of visual angle may be considered acceptable. For some applications, more than 1 degree is considered a failed calibration and requires another attempt. Participants can improve on the second or third try. Participants who consistently have a high validation error may have a vision or physiological problem that precludes their participation in an experiment. The validation results can be expressed in degrees of visual angle and displayed graphically.

Figure 2A:
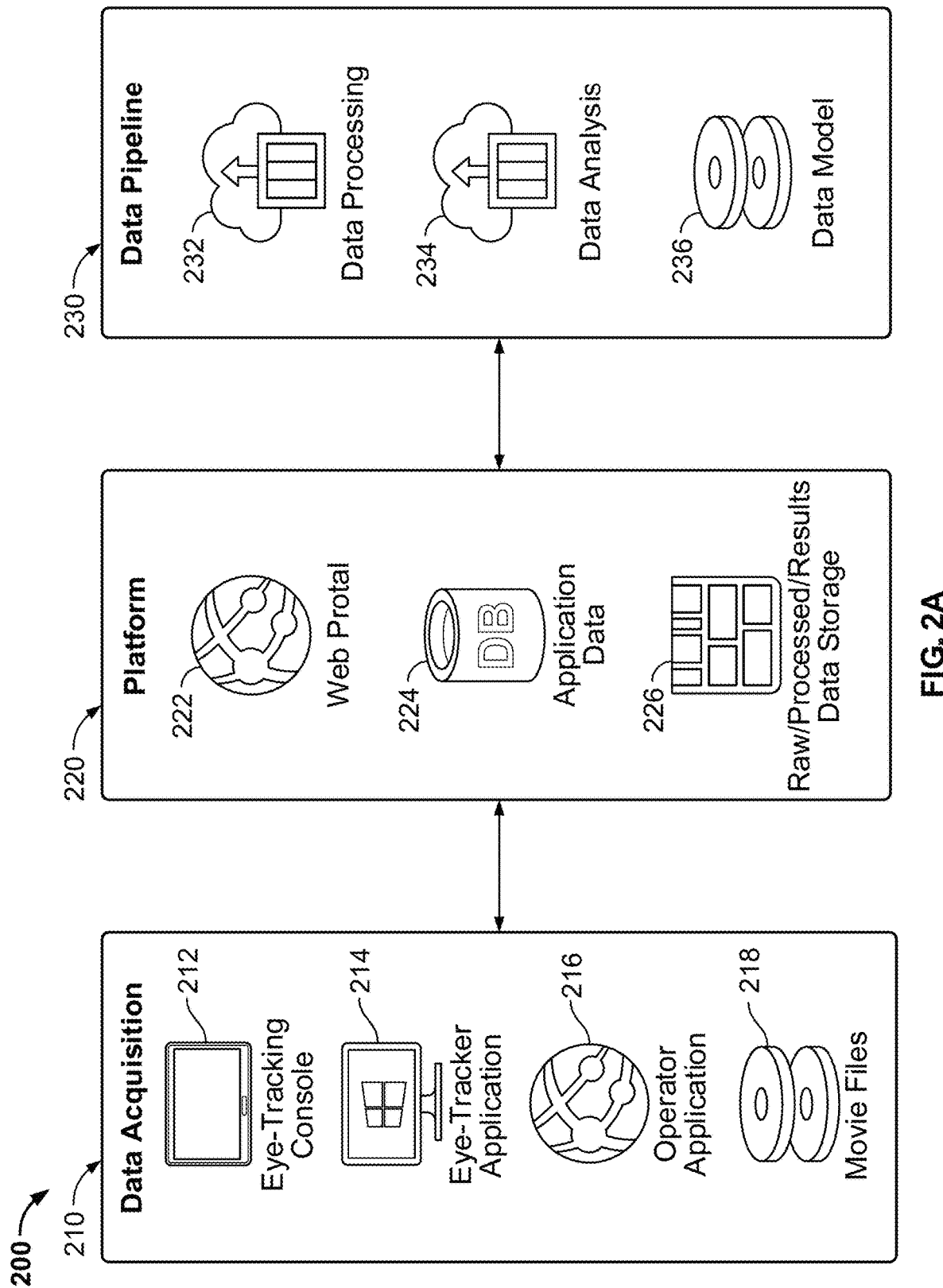
FIG. 2A is a block diagram of an example system for assessing developmental disorders via eye tracking, according to one or more embodiments of the present disclosure.

The patient-side computing device 130 can include, as illustrated in FIG. 2A, an eye-tracking application (or software) configured to retrieve or receive raw eye-tracking data collected by the eye-tracking device 134. The patient-side computing device 130 can generate session data based on the raw eye-tracking data, e.g., storing the raw eye-tracking data with associated information (timestamp information) in a data file (e.g., in .tsv format, .idf format, or any suitable format), as illustrated in FIG. 5(b). The session data can also include information of played or presented visual stimuli in another data file (e.g., in .tsv format or any suitable format), as illustrated in FIG. 5(a). The information can include timestamp information for each visual stimulus played.

In some embodiments, the patient-side computing device 130 stores a number of predetermined visual stimuli (e.g., movie or video files) that are grouped to correspond to patients of particular age groups and/or condition groups. For example, a first list of predetermined visual stimuli can be configured for ASD assessment for patients in a first age range (e.g., 5 to 16 months old), and a second list of predetermined visual stimuli can be configured for ASD assessment for patients in a second age range (e.g., 16 to 30 months old) different from the first age range. In some embodiments, an operator can use the operator-side computing device 140 to control which list of predetermined visual stimuli to play to a specific patient based on information of the specific patient. In some embodiments, the operator application sends age information upon patient selection to the eye-tracking application which then dynamically selects the appropriate preset playlist based on the age information, without operator intervention or selection. In some embodiments, the number of predetermined visual stimuli can be also stored in the operator-side computing device 140.

The testing methodology depends on the patient being awake and looking at the screen 132 of the patient-side computing device 130. During both the calibration as well as the data collection procedures, predetermined movies and/or other visual stimuli are presented to the patient via the patient-side computing device 130. These movies and/or other visual stimuli may include human or animated actors who make hand/face/body movements. As discussed with further details in FIG. 5, during the data collection period, the computing system 120 can periodically show calibration or fixation targets (that may be animated) to the patient. These data can be used later to verify accuracy.

The visual stimuli (e.g., movies or video scenes) that are displayed to a patient may be dependent on the patient's age. That is, the visual stimuli can be age-specific. In some embodiments, processing session data includes measuring the amount of fixation time a patient spends looking at an actor's eyes, mouth, or body, or other predetermined region-of-interest, and the amount of time that patient spends looking at background areas in the video. Video scenes, shown to the patient via the screen 132 of the patient-side computing device 130, may depict scenes of social interaction (e.g., an actor looking directly into the camera, trying to engage the viewing patient, for instance, or scenes of children at play). In some embodiments, the video scenes can include other suitable stimuli including, for example, animations and preferential viewing tasks. Measures of fixation time with respect to particular spatial locations in the video may relate to a patient's level of social and/or cognitive development. For example, children between ages 12-15 months show increasing mouth fixation, and alternate between eye and mouth fixation, as a result of their developmental stage of language development. As another example, a decline in visual fixation over time by a patient with respect to the eyes of actors in videos may be an indicator of ASD or another developmental condition in the patient. Analysis of the patient's viewing patterns (during the displayed movies and across a plurality of viewing sessions or compared to historical data of patients having substantially same age and/or conditions) can be performed for the diagnosis and monitoring of a developmental, cognitive, social or mental ability or disability including ASD.

The operator-side computing device 140 is configured to run an operator application (or software). In some embodiments, the operator application is installed and run in the operator-side computing device 140. In some embodiments, the operator application runs on the cloud server 110, and an operator can log in a web portal to interact with the operator application through a user interface presented on the operator-side computing device 140, as discussed with further details in FIGS. 4A-4J. The operator application can be configured to supervise or control the steps of the eye-tracking application or software in the patient-side computing device 130, e.g., to select and play specific visual stimuli for a patient and to collect raw eye tracking data. In some embodiments, the operator application interfaces with the eye-tracking software via a software development kit (SDK). In some embodiments, communication between the patient-side computing device 130 and the operator-side computing device 140 or communication between the operator application and the eye-tracking application can be done using Web Socket communication. Web Socket communication allows bi-directional communication between two devices. This bi-directional communication allows an operator to control the patient-side computing device 130 while receiving information from the patient-side computing device 130 at the same time. Web Socket communication can be done using the secure implementation of Web Socket known as Web Socket Secure (WSS). As noted above, communication between the patient-side computing device 130 and the operator-side computing device 140 (e.g., communication between the operator application and the eye-tracking application) can be through the cloud server 110. For example, an operator can use the operator-side computing device 140 to log in a web portal running on the cloud server 110 and establish a wireless connection with the patient-side computing device 130 for eye-tracking data acquisitions of the patient.

The operator application can be additionally used to perform other functions, e.g., presenting an interface to the operator showing the patient's name, date of birth, etc., information relating to the stimuli (e.g., movies) that are shown to the patient, and the like. The operator can also use the operator-side computing device 140 to log in the web portal of the cloud server 110 for device management, patient management, and data management. In some embodiments, the operator application runs on the cloud server 110 and is controlled by the operator using the operator-side computing device through the web portal. The operator can operate the computing system 120 with only minimal training.

As discussed with further details in FIGS. 3, 4A-4J, and 5, the computing system 120 can be configured for session data acquisition. In some embodiments, a session is initialized by establishing a connection between the operator-side computing device 140 and the patient-side computing device 130. After entering the patient's information into the operator application (e.g., a custom software) running on the operator-side computing device 140, the operator application can control the eye-tracking application running on the patient-side computing device 130 to select age-specific stimuli and instruct the operator or the caregiver of the patient to position the patient-side computing device 130 in front of the patient at a proper orientation and/or location. The operator can use the operator-side computing device 140 to control the operator application and/or the eye-tracking application or software to (a) calibrate the eye-tracking device 134 to the patient, (b) validate that the calibration is accurate, and (c) collect eye-tracking data from the patient as he or she watches the dynamic videos or other visual stimuli in the session, e.g., from the patient moving his or her eyes in response to predetermined movies or other visual stimuli. After the session ends, both the eye tracking data and information relating to the stimuli (e.g., a list of the stimuli viewed by the patient) can be stored in two separate data files as session data. Then the session data can be transferred, e.g., automatically by the patient-side computing device 130, to a secure database in the cloud server 110, e.g., via the network 102. The database can be remote from the computing system 120 and configured to accommodate and aggregate collected data from a number of computing systems 120.

The network 102 can include a large computer network, such as a local area network (LAN), a wide area network (WAN), the Internet, a cellular network, or a combination thereof connecting any number of mobile computing devices, fixed computing devices and server systems. Each of the computing devices 130, 140 in the computing system 120 can communicate with the cloud server 110 through the network 102.

In some embodiments, communication between on-premises computing devices 130, 140 and the cloud server 110 can be done using Hypertext Transfer Protocol (HTTP). HTTP follows a request and response model where a client (e.g., through a browser or desktop application) sends a request to the server and the server sends a response. The response sent from the server can contain various types of information such as documents, structured data, or authentication information. HTTP communication can be done using the secure implementation of HTTP known as Hypertext Transfer Protocol Secure (HTTPS). Information passed over HTTPS is encrypted to protect both the privacy and integrity of the information.

Figure 11:
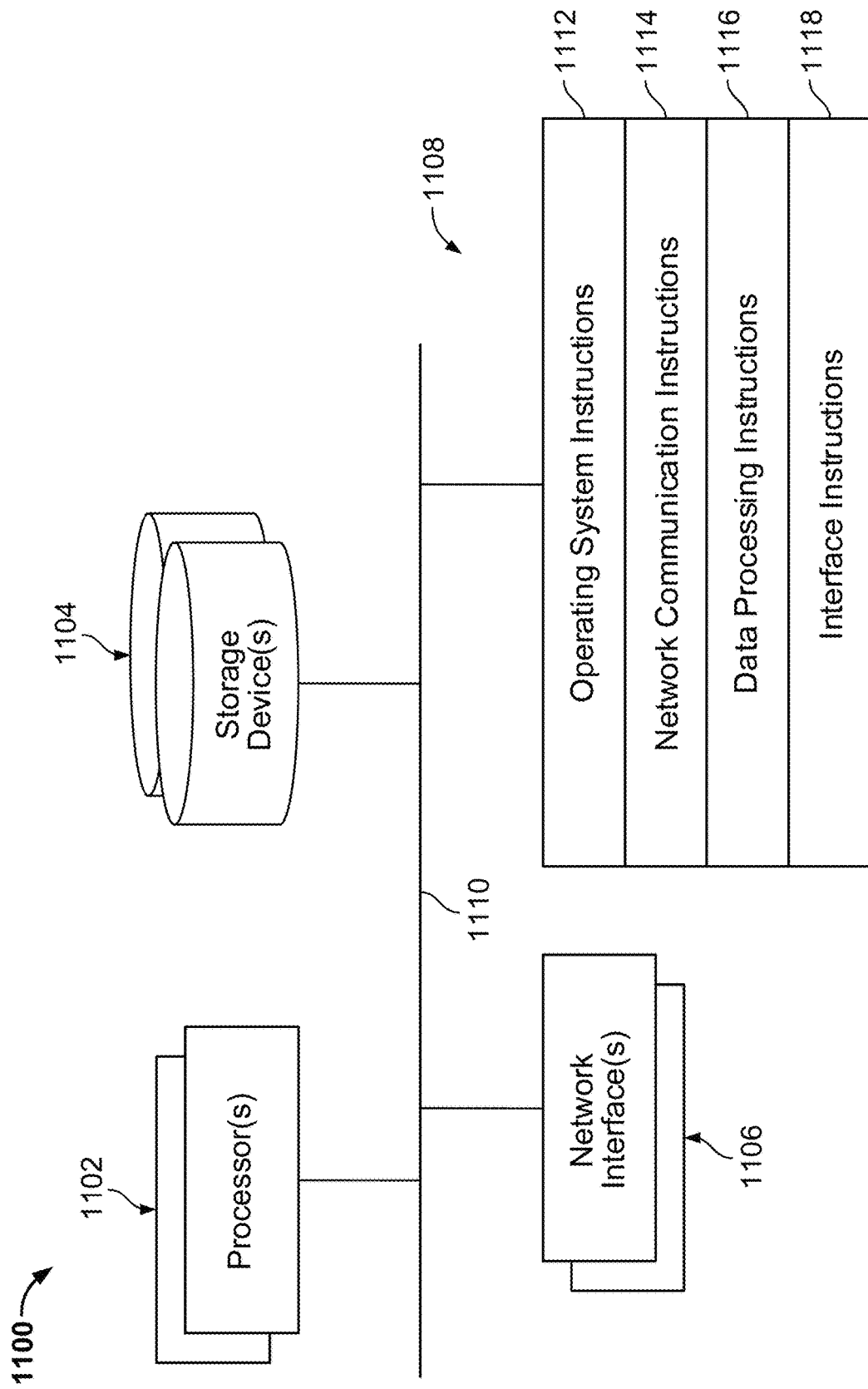
FIG. 11 illustrates an architecture for a cloud computing system, according to one or more embodiments of the present disclosure.

The cloud server 110 can be a computing system hosted in a cloud environment. The cloud server 110 can include one or more computing devices and one or more machine-readable repositories, or databases. In some embodiments, the cloud server 110 can be a cloud computing system that includes one or more server computers in a local or distributed network each having one or more processing cores. The cloud server 110 can be implemented in a parallel processing or peer-to-peer infrastructure or on a single device with one or more processors. As an example, FIG. 11 is an architecture for a cloud computing system which can be implemented as the cloud server 110.

As illustrated in FIG. 1, the cloud server 110 includes a cloud platform 112 and a data pipeline system 114. As discussed with further details in FIGS. 2A-2G, the cloud platform 112 can be configured to provide a web portal, store application data associated with treatment providers or tenants, and store data, e.g., raw eye-tracking data, processed data, analytical and/or diagnostic results. The data pipeline system 114 is configured to perform data processing and data analysis.

Figure 6:
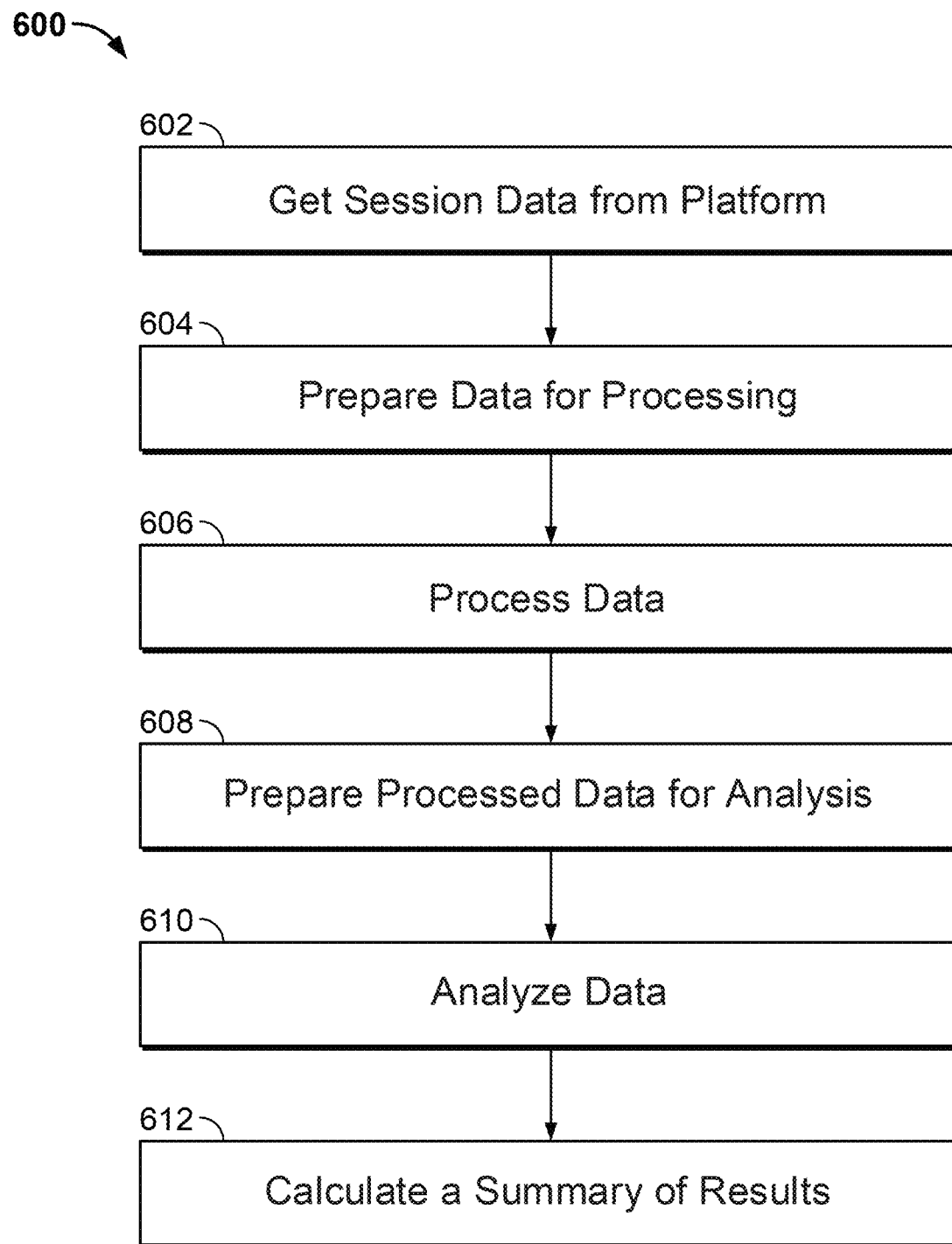
FIG. 6 is a flowchart of an example process for managing session data, according to one or more embodiments of the present disclosure.
Figure 7A:
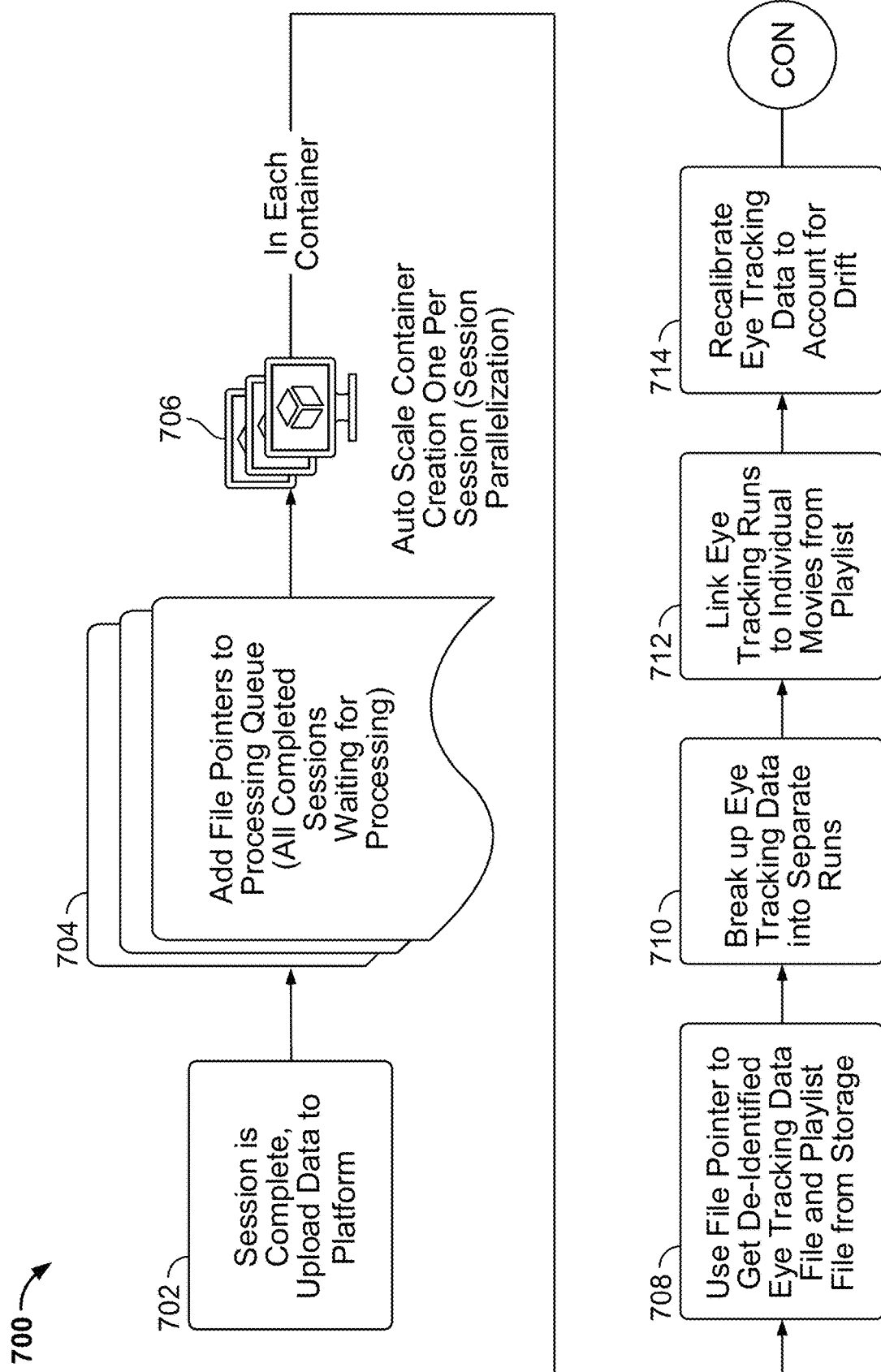
FIGS. 7A-7B show a flowchart of another example process for managing session data, according to one or more embodiments of the present disclosure.
Figure 7B:
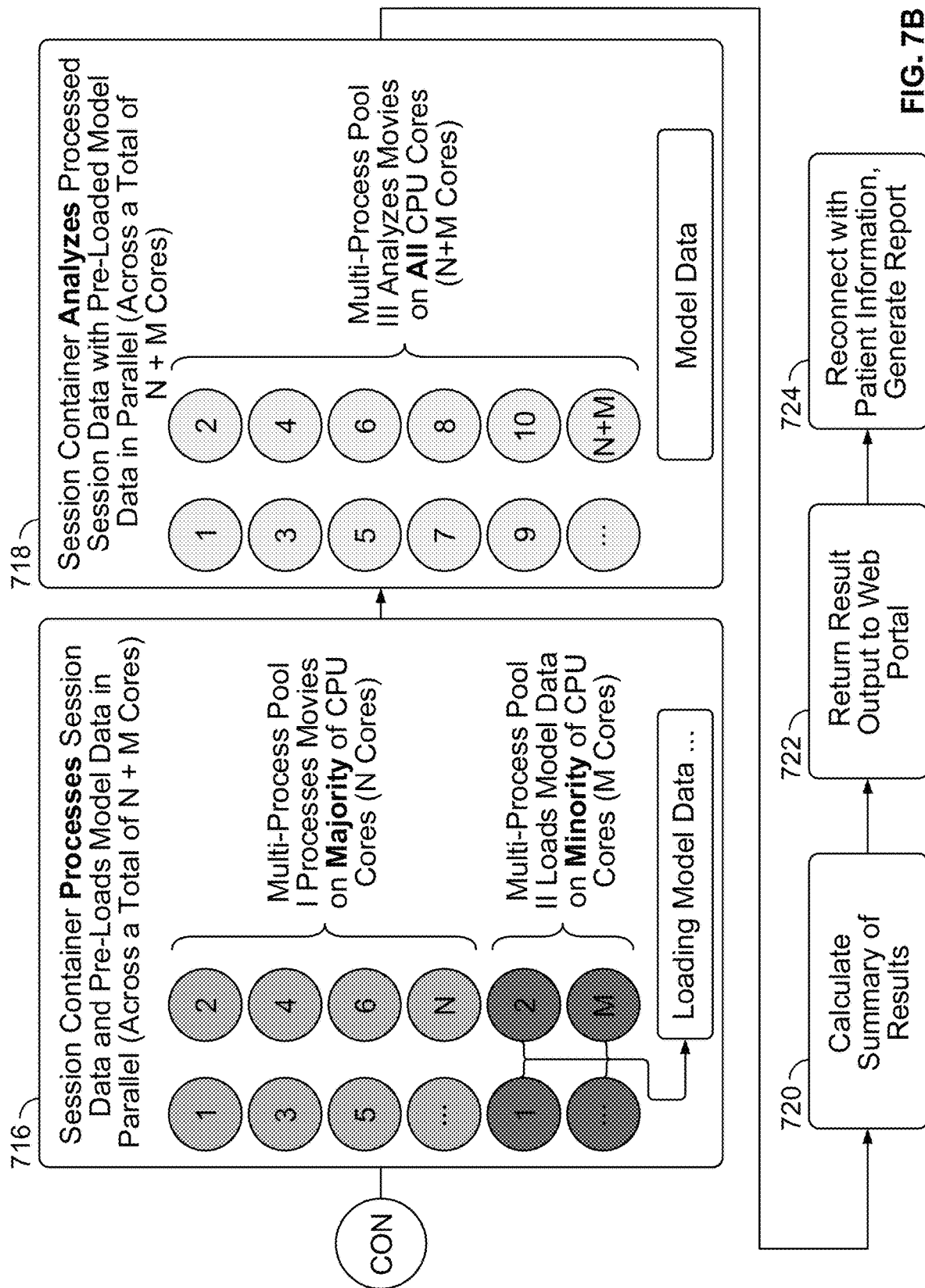

In some embodiments, as discussed with further details in FIGS. 6 and 7A-7B, the cloud server 110 is configured to automatically receive, process, and analyze session data from multiple computing systems. Moreover, the cloud server can process and analyze session data of a number of sessions from a large number of computing systems in parallel, which can greatly improve session processing speed and provide diagnosis results in a short period of time, e.g., within a 24-hour window. For example, receipt of session data by the cloud server 110 (e.g., by the cloud platform 112) can initiate an automatic software-implemented processing and analysis process (e.g., by the data pipeline system 114). In the process, the patient's individual data can be compared to models of eye-tracking data which were previously generated from historical eye-tracking data of patients having substantially same ages, backgrounds, and/or conditions. The result of the comparison can be a diagnosis of a neurodevelopmental disorder including but not limited to ASD, a measure of the patient's developmental/cognitive functioning and/or prescriptive recommendation for a treatment plan. Alternatively or additionally, the collected data is compared and/or reviewed for a given patient over multiple sessions (and over a predetermined time period) to identify a potential change in visual fixation (e.g., a decline in visual fixation). Those results may be condensed into a diagnostic report, for use by the patient's physician. In some embodiments, once a diagnostic result is ready, the cloud server 110 can transfer the diagnostic result to the operator-side computing device 140, and the diagnostic result can be presented on a user interface of the operator-side computing device 140, e.g., as discussed with further details in FIGS. 8A-8C.

In some embodiments, a large amount of model data, including data related to patients at similar ages, similar backgrounds, and/or similar situations, can be used with processed session data for a patient to generate a diagnosis result for the patient, e.g., using comparison or inference via statistical models, algorithms, artificial intelligence (AI) models such as machine learning or artificial neural network models, which can greatly increase accuracy of the diagnosis results.

The environment 100 involves three major steps corresponding to the three parts of the environment 100 shown in FIG. 1 (e.g., the computing system 120 for data acquisition, the cloud platform 112, and the data pipeline system 114). As discussed with further details in FIGS. 2A-2G, the three parts can be configured together to reliably collect data for patients, and efficiently process and analyze the collected data for the diagnosis of ASD or other cognitive, developmental, social or mental abilities or disabilities.

FIG. 2A is a block diagram of an example system 200 for assessing developmental disorders via eye tracking, according to one or more embodiments of the present disclosure. The system 200 can be implemented in the environment 100 of FIG. 1. According to three steps of a data process, the system 200 includes three subsystems: data acquisition subsystem 210, a platform subsystem 220, and a data pipeline subsystem 230. Each subsystem can be composed of corresponding hardware and software items.

The data acquisition subsystem 210 is configured to collect eye-tracking data of patients. The data acquisition subsystem 210 can be the computing system 120 of FIG. 1. As shown in FIG. 2A, the data acquisition subsystem 210 includes an eye-tracking console 212 running an eye-tracker application 214 and an operator-side computing device (e.g., 140 of FIG. 1) running an operator application 216. In some embodiments, the operator application 216 is deployed in the operator-side computing device. In some embodiments, the operator application 216 is deployed in the platform subsystem 220, and the operator can use the operator-side computing device to log in the platform subsystem 220 through a web portal 222 to run the operator application 216 on the platform subsystem 220. Deploying the operator application 216 in the platform subsystem 220 can avoid deploying the operator application 216 in one or more operator-side computing devices, which can reduce software and hardware requirements for the operator-side computing devices, and enable to conveniently maintain or update the operator application 216, e.g., without maintaining or updating the operator information 216 on each of the one or more operator-side computing devices.

The eye-tracking console 212 can be an integrated device including the patient-side computing device 130 (e.g., a tablet) and the eye-tracking device 134 of FIG. 1. As noted above, the data acquisition subsystem 210 can include a number of movie files 218 that are stored in the eye-tracking console 212 and optionally in the operator-side computing device. The movie files 218 can be predetermined age-specific visual stimuli for patients at different ages and/or different conditions.

As described in FIG. 1, the platform subsystem 220 and the data pipeline subsystem 230 can be included in a network-connected server such as a cloud server (e.g., the cloud server 110 of FIG. 1) and implemented in a centralized cloud-hosted environment that is provided by a cloud provider, e.g., Microsoft Azure. In some embodiments, the platform subsystem 220 is configured for management and orchestration of resources of the cloud-hosted environment. The platform subsystem 220 can be the cloud platform 112 of FIG. 1. As illustrated in FIG. 2A, the platform subsystem 220 includes a web portal 222, database 224 storing application data, and database 226.

The web portal 222 can be a web-based interface. Through the web portal 222, an operator (e.g., a medical professional) can login into, e.g., using the operator-side computing device, the platform subsystem 220 to manage (view and/or query) application data 224 stored in the database 224 and/or data in the database 226. For example, the web portal 222 allows for an operator to view diagnostic results. A prewritten course of action may be provided based on the diagnostic results (e.g., seek further evaluation).

Figure 2B:
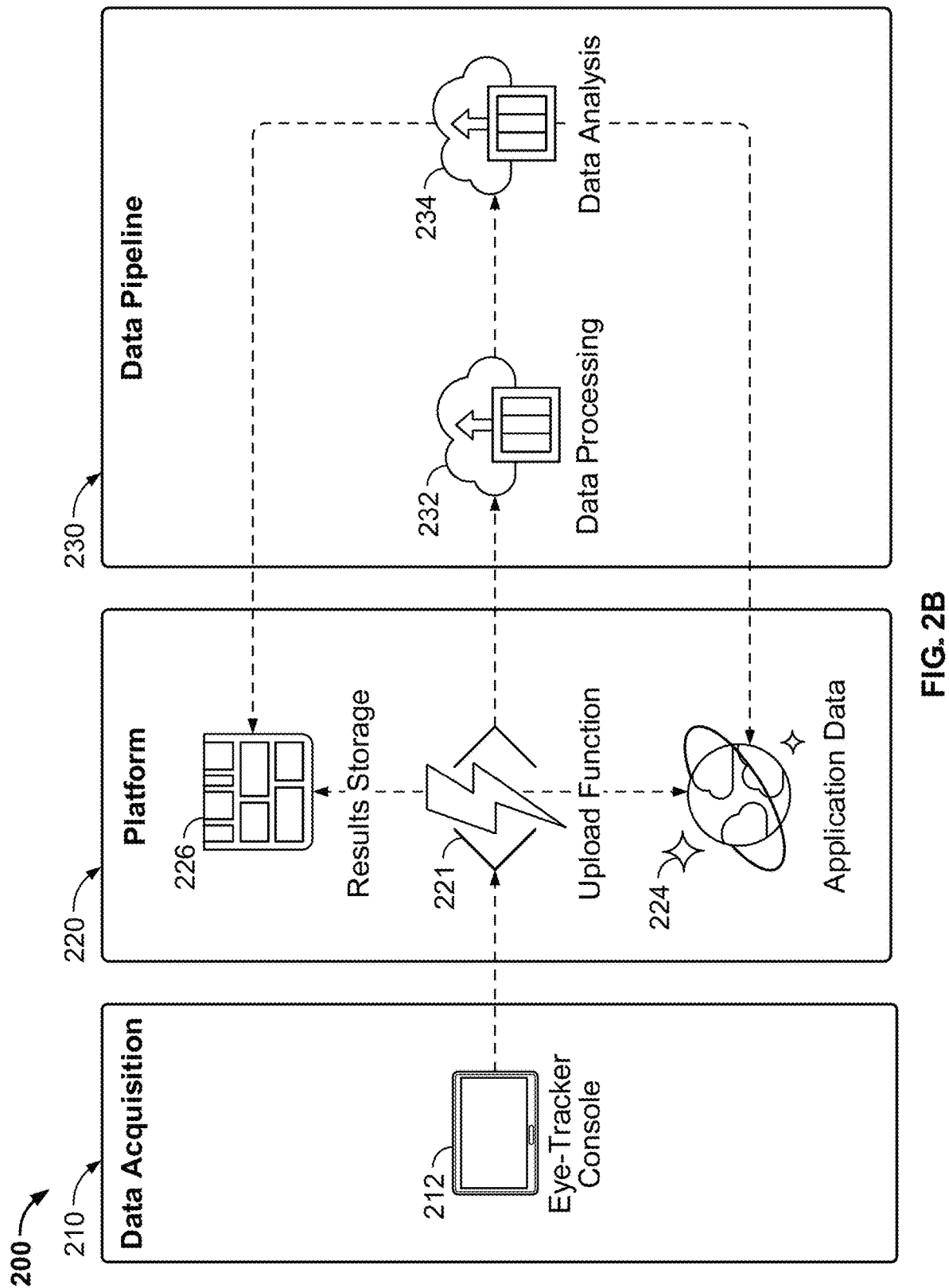
FIG. 2B shows an example of managing session data in the system of FIG. 2A, according to one or more embodiments of the present disclosure.
Figure 2C:
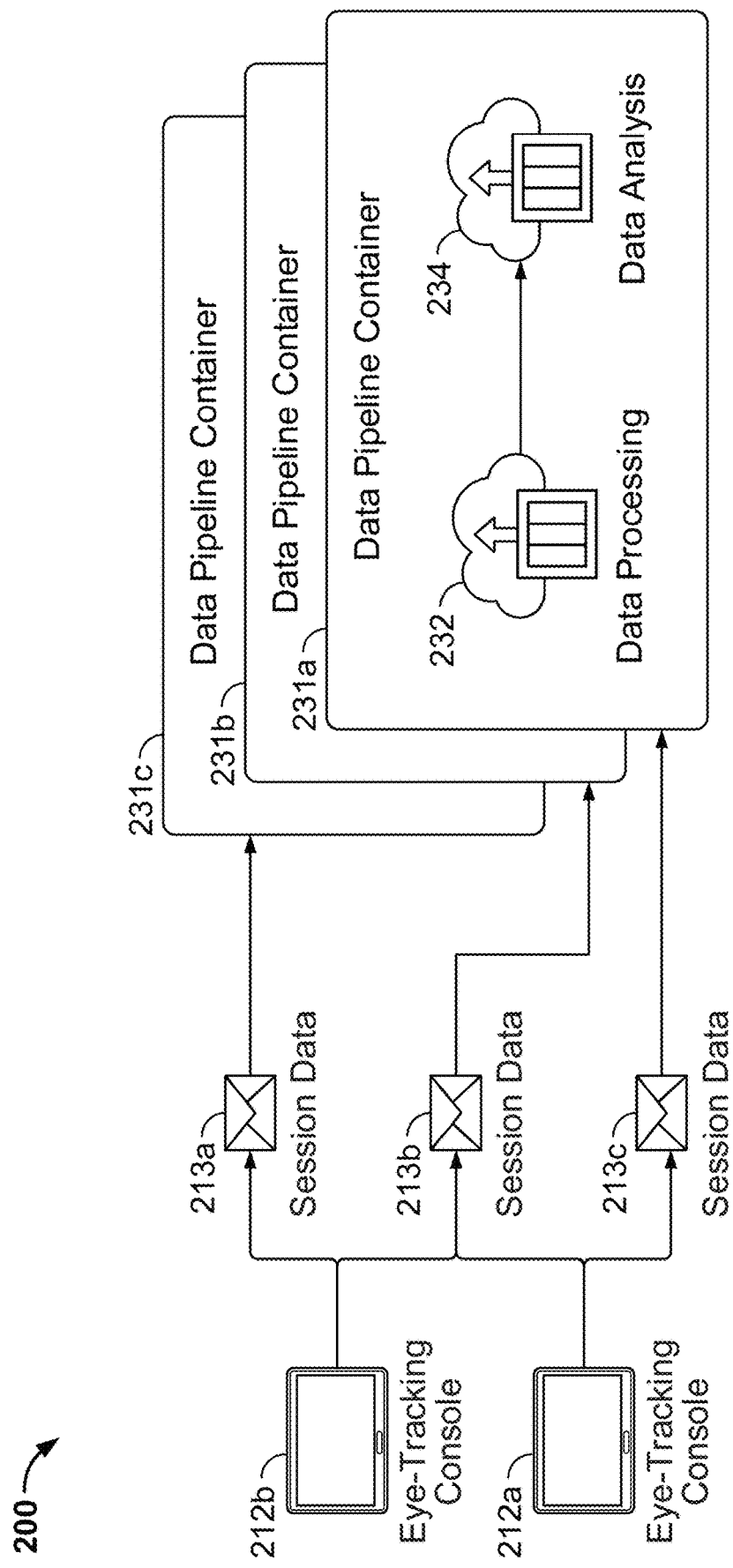
FIG. 2C shows an example of managing multiple session data in parallel in the system of FIG. 2A, according to one or more embodiments of the present disclosure.
Figure 2D:
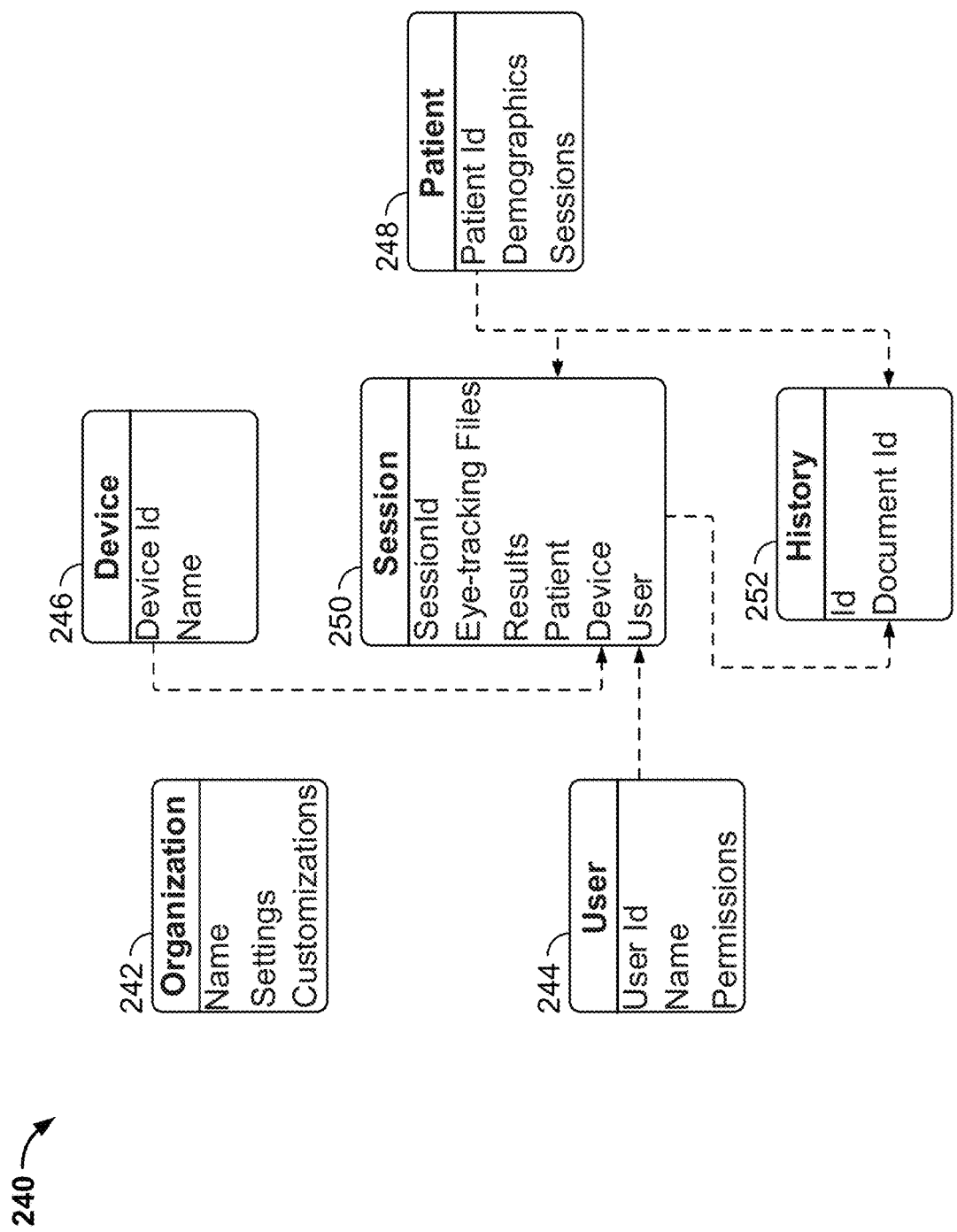
FIG. 2D shows an example database storing different types of documents as application data in the system of FIG. 2A, according to one or more embodiments of the present disclosure.

As an example of the database 224, FIG. 2D shows a database 240 storing different types of documents. The database 240 can be a NoSQL database such as Azure Cosmos DB. The different types of documents can be stored as application data in the database 240. Unlike relational databases, NoSQL databases do not have strong relationships between documents. Dotted lines in FIG. 2D indicate references and information embedding between the documents.

In some embodiments, the database 240 stores corresponding application data for a treatment provider (or a tenant). The treatment provider can be a healthcare organization that includes, but is not limited to, an autism center, a healthcare facility, a specialist, a physician, or a clinical study. An organization can vary in structure, patient volume, and lifespan. As illustrated in FIG. 2D, the corresponding application data can include organization document 242, user document 244, device document 246, patient document 248, session document 250, and history document 252. A user can be an operator associated with the healthcare organization, e.g., a medical assistant, a specialist, a physician, or any other medical professional.

The organization document 242 contains settings and customizations for the organization. The user document 244 contains the identifier information along with a user's roles and permissions. The user role indicates whether the user is either an administrator or operator that is associated with a different security level or permission. The device document 246 contains identifier information for each eye-tracking console, e.g., 212 of FIG. 2A, associated with the organization. The patient document 248 contains information about the patient, e.g., an infant or a child treated as a patient for development assessment. The session document 250 contains information related to a session that can be composed of a session identifier (session ID), a reference to the patient, a reference to the user performing the session, a pointer to the eye-tracking data, and the results of data processing and analysis. The history document 252 can be used to maintain a version history of changes to a document. The document mirrors the structure of its parent document and include additional audit information. In some embodiments, the database 224 allows for URL-based querying (e.g., for those with administrative roles) to query across multiple variables. For example, variable may include patients/devices/sessions, adverse events, etc.

In some embodiments, the cloud server including the platform subsystem 220 and the data pipeline subsystem 230 can be implemented in a centralized cloud environment, which can provide more flexibility to expand a capability of the cloud server. For example, the cloud server can utilize a multi-tenant architecture for providing Software as a Service (SaaS) subscription-based diagnostic services to treatment providers. In the multi-tenant architecture, treatment providers share a single version of the software across a variety of geographic locations. The term "tenant" in a multi-tenant architecture describes a single treatment provider of the system. Resources of the cloud server can be dynamically managed based on a total number of tenants and expected average workload, e.g., how many tenants are accessing the cloud server at a given time point. The cloud server can adopt horizontal scaling techniques such as auto-scaling to handle spikes in the resource workload.

In a multi-tenant architecture where the application is shared, it is important to isolate their tenant data and prevent other tenants from accessing their tenant data. This is known as isolation. There are 3 different isolation strategies that can be implemented: shared database, database per tenant, and application per tenant. In Shared Database strategy, tenants share a single instance of the application, and all data is stored in a single database. In Database Per Tenant strategy, e.g., strategy 260 illustrated in diagram (a) of FIG. 2E, tenants share a single instance of an application in an application layer 262 but have their own databases 264 (e.g., database 224 of FIG. 2A or 240 of FIG. 2D). In Application Per Tenant strategy, e.g., strategy 270 illustrated in diagram (b) of FIG. 2E, each tenant gets its own instance of an application in a respective application layer 272 and its own database 274 (e.g., database 224 of FIG. 2A or 240 of FIG. 2D). The cloud server can deploy the Database per Tenant strategy 260 or the Application per Tenant strategy 270 to treatment providers.

With continued reference to FIG. 2A, the database 226 is configured to store raw eye-tracking data or session data, processed session data, analytical results, and/or diagnostic results or reports. The database 226 can be a storage platform (e.g., Azure Blob), and can be paired with tools written in any suitable programming language (e.g., Python, Matlab), allowing for URL based interface and query to the database 226. Additionally, the database 226 may be compatible with programming languages (e.g., Python, Matlab) used for transferring data from the data acquisition subsystem 210 to the database 226, and from the database 226 to the data pipeline subsystem 230. For example, where the patient-side computing device (e.g., 130 of FIG. 1) is located at a medical facility, data collection occurs at that facility and the data are transferred between the database 226 and the patient-side computing device. The database 226 can be secure, HIPAA-compliant, and protected by a redundant backup system.

In some embodiments, the platform subsystem 220 is configured to enable one or more operations including (a) intake of new patient information, (b) storage of raw data files (e.g., including eye tracking data), (c) automated and secure transfer of files between a data collection device (e.g., the eye-tracking console 212 of FIG. 2A), data processing computer, and database, (d) tabulation and querying of data for the purposes of assessing device utilization and other data quality metrics, and e) access to results of processing by physicians. One or more of the operations (a) to (c) can be performed by an upload function module 221 in the platform subsystem 220.

With continued reference to FIG. 2A, the data pipeline subsystem 230 is configured to process and analyze patient eye-tracking data along with producing a diagnostic result. In some embodiments, the data pipeline subsystem 230 includes data processing module 232, data analysis module 234, and model data 236. As discussed with further details in FIGS. 7A-7B below, the data processing module 232 is configured to process session data including eye-tracking data to obtain processed session data, and the data analysis module 234 is configured to analyze the processed session data using the model data 236 to generate a diagnostic result.

In some embodiments, the system 200 includes interfaces for devices and subsystems. An interface can be inter-subsystem. For example, the system 200 can also include an interface between the data acquisition subsystem 210 to the cloud platform subsystem 220, and an interface from the cloud platform subsystem 220 to the data pipeline subsystem 230. An interface can be intra-subsystem. For example, the system 200 can include an interface between eye-tracking console hardware (e.g., a tablet and an eye-tracking device) and eye-tracking application software.

FIG. 2B shows an example of processing single session data in the system 200 of FIG. 2A, according to one or more embodiments of the present disclosure. As discussed above, after a data collection session is completed, the eye-tracking console 212 can automatically transfer session data of the session to the platform subsystem 220. The session data can include two files: one containing raw eye-tracking data (e.g., gaze position coordinates, blink data, pupil size data, or a combination thereof) and the other containing information relating to the stimuli (e.g., a list or playlist of those movies viewed by the patient). Through the upload function module 221 implemented in the platform subsystem 220, the session data can be stored in the database 226 and stored into application data in the database 224. Then, the stored session data can be automatically transferred from the platform subsystem 220 to the data pipeline subsystem 230 for data processing and analysis, without human intervention. For example, a software script written in any suitable programming language (e.g., Python, Matlab) may be used to transfer raw, unprocessed data files from the database 226 to the data pipeline subsystem 230 for processing. The session data is first processed by the data processing module 232 and then analyzed by the data analysis module 234, which yields diagnostic information about the patient.

In some embodiments, three files are generated, one containing processed eye-tracking data, one containing a summary of eye tracking statistics, and one containing the diagnostic information. The file containing diagnostic information can be uploaded to the database 224 to be associated with the patient in the application data, as illustrated in FIG. 2D. The three files can then be uploaded to the database 226 for storage. In some cases, the processed eye-tracking data are tabulated into a session table. Summary of eye tracking information (e.g., fixation samples/movie, etc.) can be read from the processed summary file and tabulated in the database 226 for subsequent query. Summary values (e.g., percentage fixation/movie, etc.) can be then calculated within the database 226.

FIG. 2C shows an example of processing multiple session data in parallel in the system 200 of FIG. 2A, according to one or more embodiments of the present disclosure. As illustrated in FIG. 2C, multiple eye-tracking consoles 212a, 212b can transmit a plurality of session data 213a, 213b, 213c of sessions (referred to generally as session data 213 or individually as session data 213) to the platform subsystem 220. In the data pipeline subsystem 200, the data processing module 232 and the data analysis module 234 can be written in a suitable programming language (e.g., Python), which enable to deploy the data processing module 232 and data analysis module 234 in containers 231a, 231b, 231c (referred to generally as containers 231 or individually as container 231). Each session can be processed using its own instance of data processing and analysis. The use of containers allows data processing and analysis to be done as session data are uploaded from the data acquisition subsystem 210, which can result in sessions being returned within a short period of time, e.g., within a 24-hour window.

As discussed with further details in FIGS. 7A-7B, the cloud server can process and analyze session data of a number of sessions from a large number of computing systems in parallel. First, the cloud server can deploy a respective container (e.g., 231) for each session, and the respective container can include a corresponding data processing module 232 and a corresponding data analysis module 234. In this way, once session data (e.g., 213) of a session is uploaded by a corresponding eye tracking console 212, the session data of the session can be processed and analyzed using its own container (e.g., 231 having its own instance of data processing and data analysis). Second, while session data of multiple sessions are being processed in corresponding containers, e.g., using a majority of processing units (or cores) in the cloud server, model data for analyzing the processed session data can be pre-loaded into the corresponding containers in parallel, e.g., using the remaining or a minority of the processing units in the cloud server. Third, all of the processed session data and the loaded model data can be analyzed in the corresponding containers in parallel, e.g., using the total number of processing units in the cloud server. The use of parallelization in multiple ways can greatly improve the speed of session data processing and analysis and provide speedy diagnostic results in the short period of time, e.g., within a 24-hour window. For example, once a diagnostic result is available, the cloud server can transmit the diagnostic result to a corresponding operator-side computing device (e.g., 140 of FIG. 1), and the diagnostic result can then be displayed in a result interface of the operator application 216. The parallelization can also make the cloud server be more efficient in resource utilization, which can further improve the system performance.

Figure 2E:
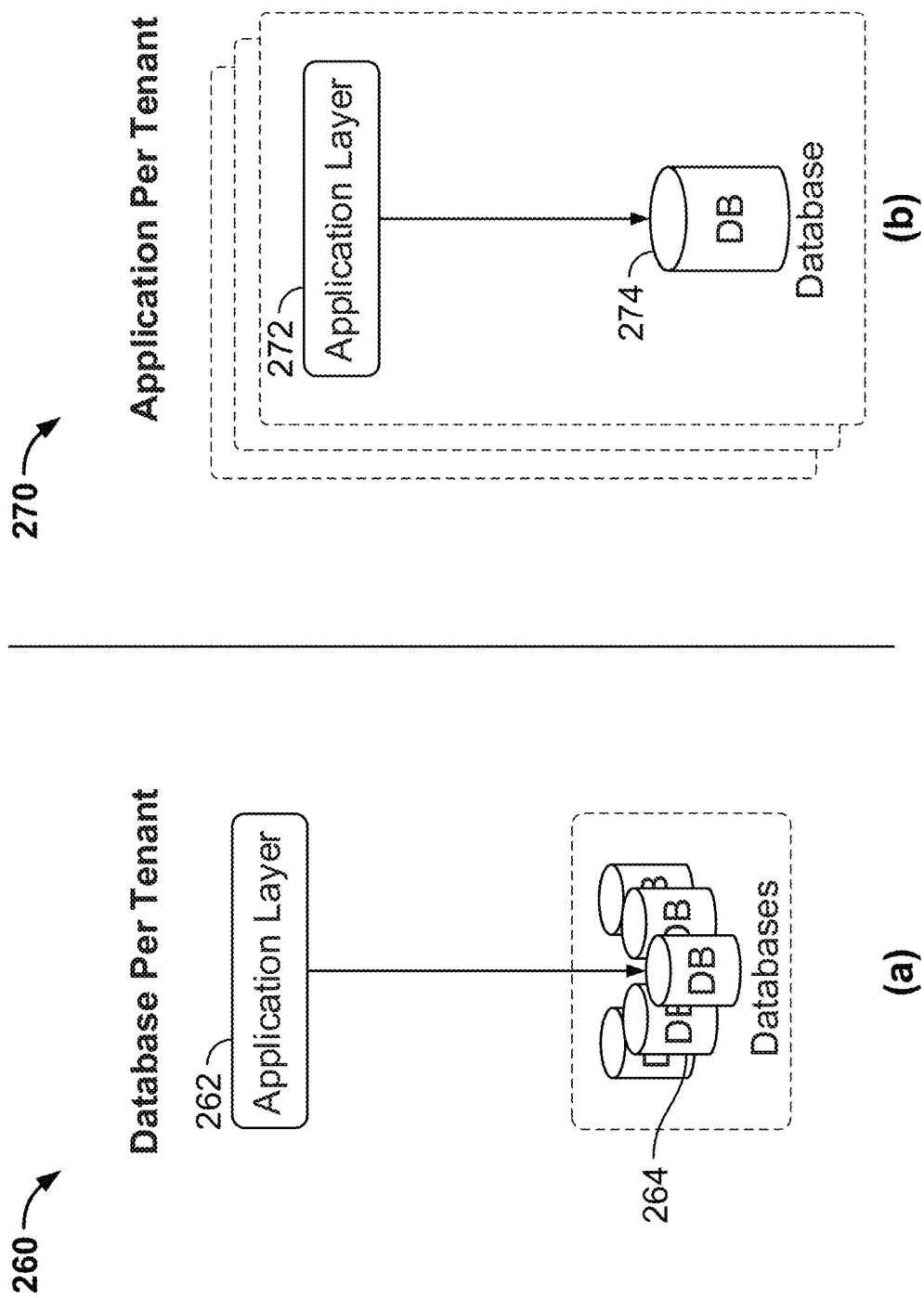
FIG. 2E shows examples of multi-tenant architectures in the system of FIG. 2A, according to one or more embodiments of the present disclosure.
Figure 2F:
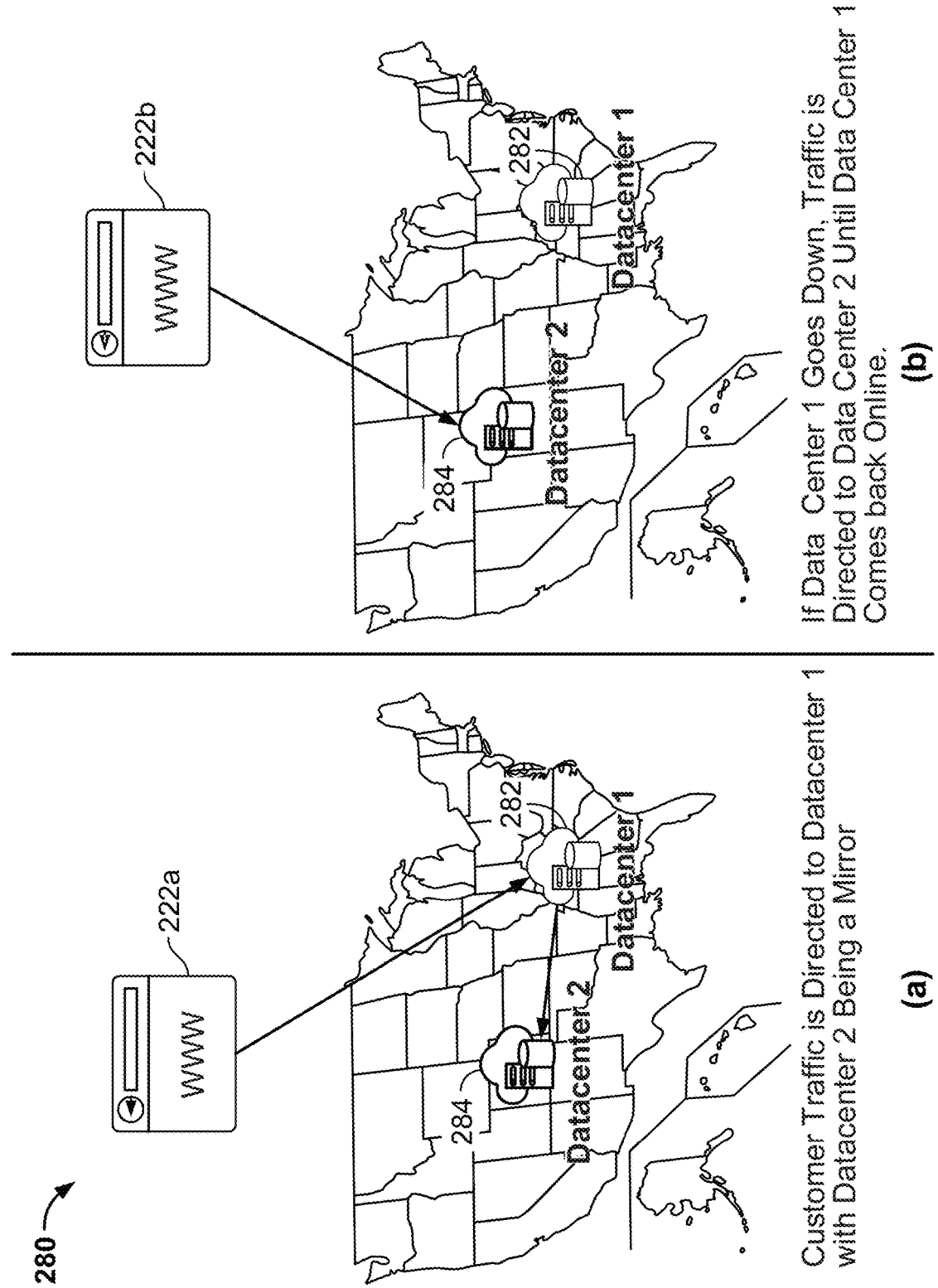
FIGS. 2F-2G show an example for data backup for the system of FIG. 2A, according to one or more embodiments of the present disclosure.

FIG. 2F show an example configuration 280 for data backup for the system 200 of FIG. 2A, according to one or more embodiments of the present disclosure. The configuration 280 can enable high availability of services to treatment providers, such that the treatment providers can access their services regardless of any outages in one or more particular regions of the cloud server (e.g., the platform subsystem 220 and the data pipeline subsystem 230).

High availability refers to treatment providers' abilities to access their services regardless of whether a cloud service provider suffers an outage. Availability can be achieved by replicating a resource in a different physical location. The cloud server implemented herein can be provided by a cloud service provider that can provide Platform as a Service (PaaS) resources with either high availability built-in or configurable high availability. The resources that are hosted in the cloud environment can have high availability using high-availability service level agreements or through the use of geo-redundancy.

FIG. 2F shows an example of high-availability through geo-redundancy. As shown in FIG. 2F(a), resources of the cloud server can be hosted in a first data center 282 having a web portal 222a. The resources are replicated in a second data center 284. When the first data center 282 works properly, treatment provider traffic is directed to the first data center 282, with the second data center 282b being a mirror. However, as shown in FIG. 2F(b), when the first data center 282 goes down, the treatment provider traffic is redirected to the replicated resources in the second data center 284 running a replicated web portal 222b. The switching process can be seamless, and treatment providers may be unaware of the switch to different resources in a replicated data center.

Figure 2G:
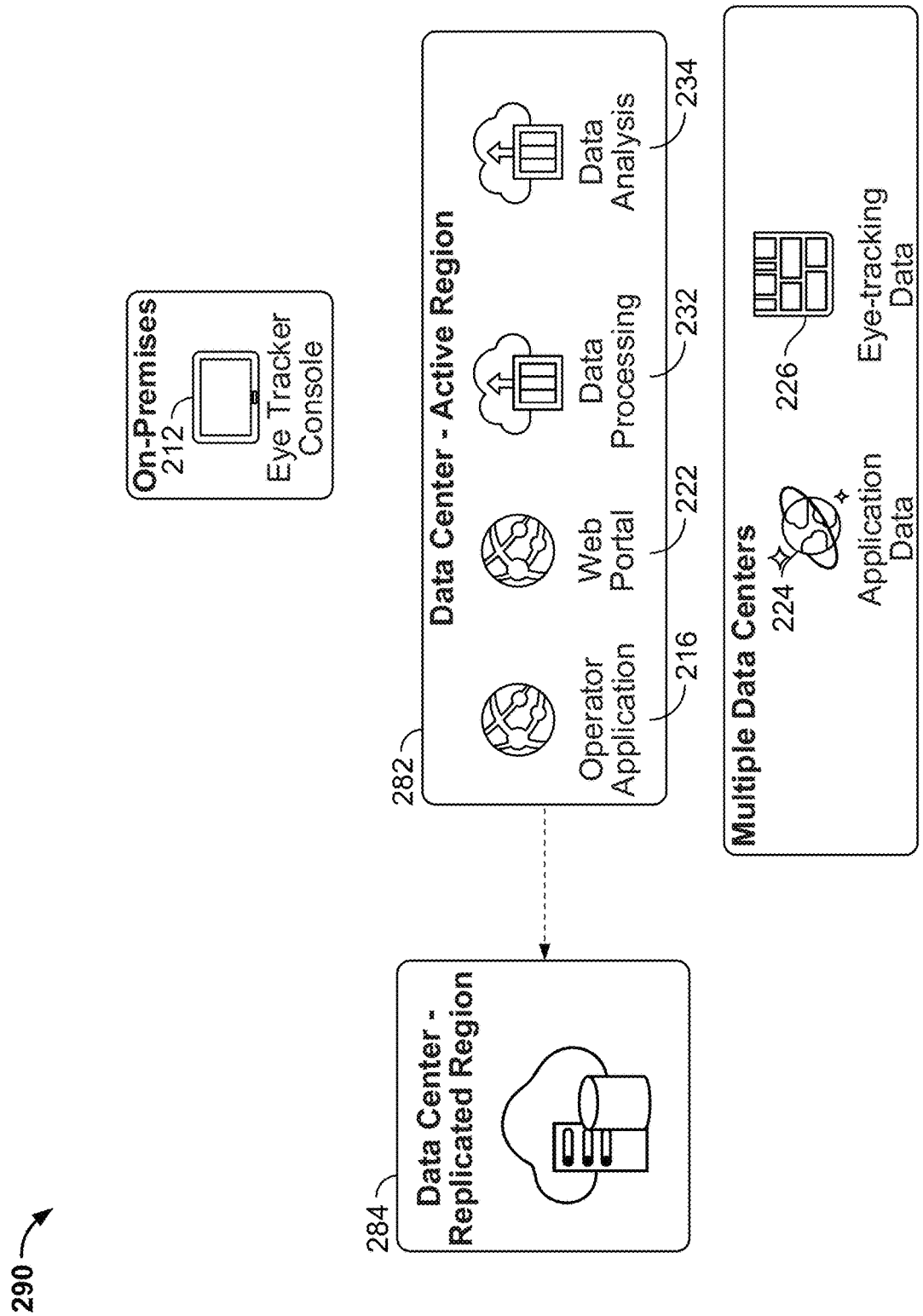

FIG. 2G shows an example data backup for the system 200, e.g., the platform subsystem 220 and the data pipeline subsystem 230. The database 224 storing application data and the database 226 storing raw and processed eye-tracking data and analyzed or diagnostic results can be stored in multiple data centers. The web portal 222 in the platform subsystem 220, and the data processing module 232 and the data analysis module 234 in the data pipeline subsystem 230, and optionally operator application 216 (running on the platform subsystem 220) can be included in an active data center 282, and can be replicated in a backup data center 284.

Example Processes for Session Data Acquisition

Figure 3:
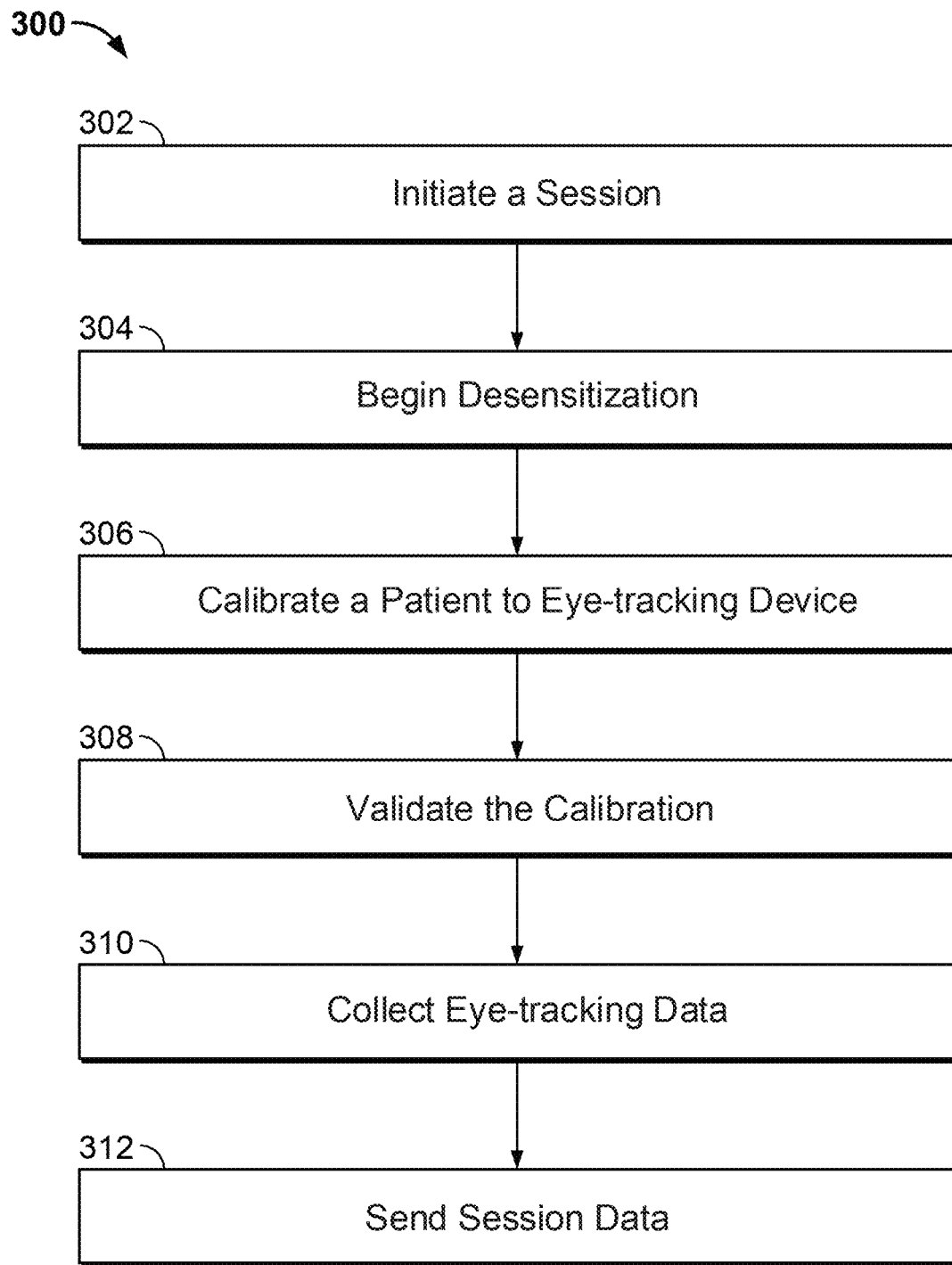
FIG. 3 is a flowchart of an example process for session data acquisition, according to one or more embodiments of the present disclosure.

FIG. 3 is a flowchart of an example process 300 for session data acquisition, according to one or more embodiments of the present disclosure. The process 300 can be performed by a system, e.g., the computing system of 120 of FIG. 1 or the data acquisition subsystem 210 of FIG. 2A. The system includes an operator-side computing device (e.g., 140 of FIG. 1) and one or more patient-side computing devices (e.g., 130 of FIG. 1) integrated with associated eye-tracking devices (e.g., 134 of FIG. 1). Each of the operator-side computing device and the one or more patient-side computing devices can communicate with a network-based server or a cloud server (e.g., the cloud server 110 of FIG. 1 or the cloud server as described in FIGS. 2A-2G) via a network (e.g., the network 102 of FIG. 1). The system can be associated with a treatment provider, e.g., providing developmental disorder assessment and/or treatment services to patients. The cloud server can be associated with a service provider for providing services, e.g., data processing, analysis, and diagnostic results, to treatment providers. For illustration, FIGS. 4A-4J show a series of illustrative display screens presented on an operator-side computing device (a) and on a patient-side computing device (b) during session data acquisition (e.g., in the process 300 of FIG. 3), according to one or more embodiments of the present disclosure.

At step 302, a session is initiated, e.g., by establishing a connection or communication between the operator-side computing device and a patient-side computing device. In some embodiments, the two computing devices 130 and 140 can be wirelessly connected, e.g., via a wireless connection, without physical connection. The wireless connection can be through a cellular network, a wireless network, Bluetooth, a near-field communication (NFC) or other standard wireless network protocol. In some cases, the patient-side computing device can be also configured to connect to the operator-side computing device through a wired connection such as universal serial bus (USB), e.g., when the wireless connection fails.

Figure 4A:
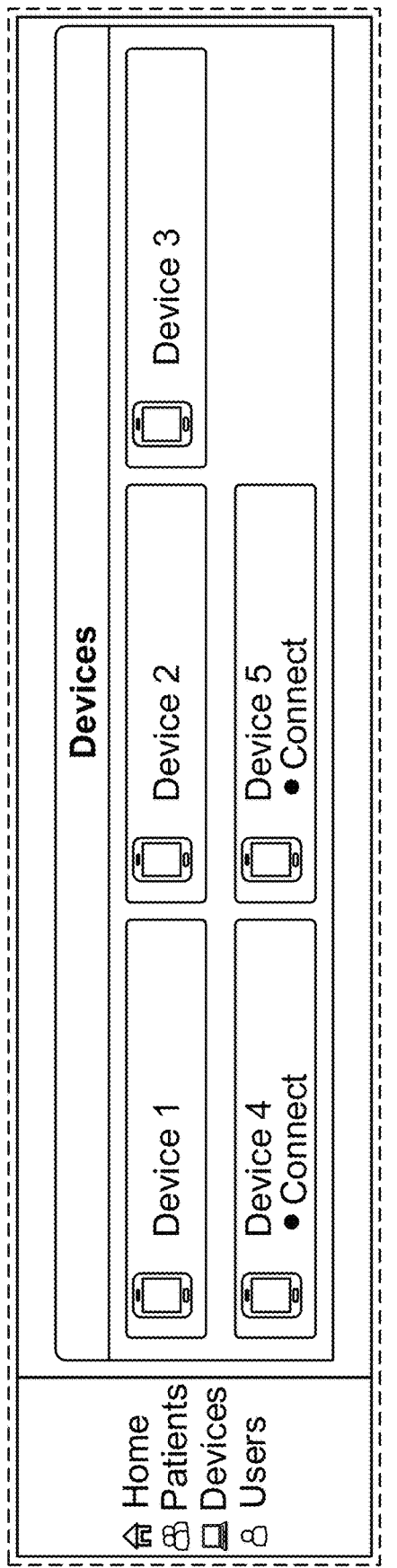
FIGS. 4A-4J show a series of illustrative display screens presented on an operator device (diagram a) and on a participant device (diagram b) during session data acquisition, according to one or more embodiments of the present disclosure.
Figure 4A:
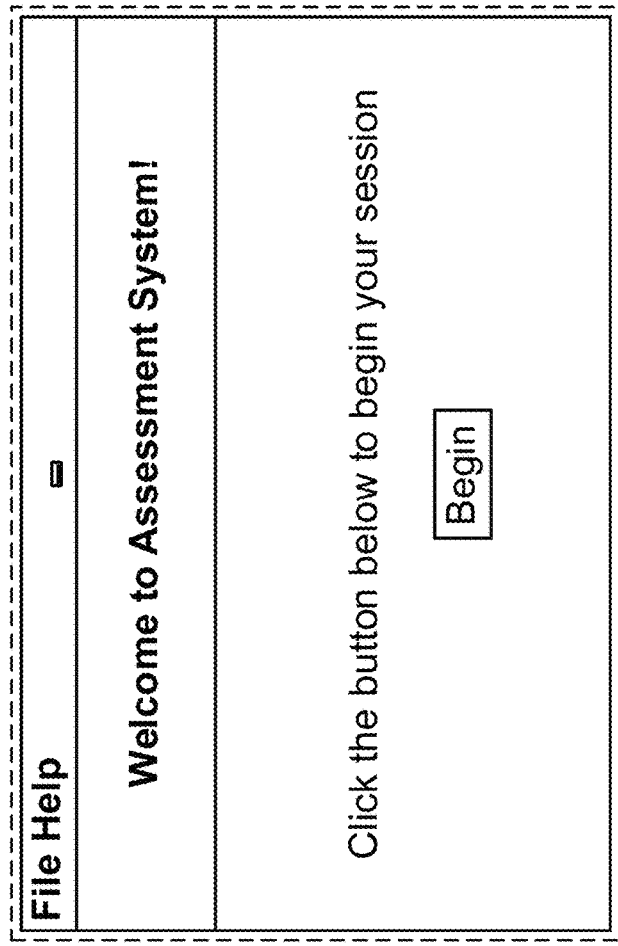

In some embodiments, the connection between the operator-side computing device and the patient-side computing device is established by the two computing device communicating with the cloud server that, in turn, provides communication between the operator-side computing device and the patient-side computing device. For example, as illustrated in FIG. 4A, an operator (e.g., a medical assistant, a medical professional, or any other representative of the treatment provider) can log in a web portal (e.g., 222 of FIG. 2A) running on the cloud server for device management, patient management, and data management. The operator can have a corresponding user role and permission, e.g., as discussed in FIG. 2D. Diagram (a) of FIG. 4A shows a user interface (UI) presented on a display screen of the operator-side computing device after the operator logs in the web portal using the operator-side computing device. The UI can be a user interface of an operator application (e.g., 216 of FIG. 2A) running on the cloud server or on the operator-side computing device.

As shown in diagram (a) of FIG. 4A, the UI includes a menu showing buttons "Home", "Patients", "Devices", and "Users". By clicking a button, corresponding information (e.g., patient information, device information, or user information) can be presented in the UI. For example, when the button "Devices" is clicked, the UI shows a list of names of patient-side computing devices, e.g., Device 1, Device 2, Device 3, Device 4, Device 5, that are controllable by the operator. If a patient-side computing device is connected to the cloud server, e.g., Device 4, Device an indication, e.g., a string showing "connect", can be presented adjacent to the name of the patient-side computing device. The operator can select one of the names, e.g., Device 4, to connect a corresponding patient-side computing device with the operator-side computing device. Once the name is selected, the UI shows a request for an access code to be input for connecting the corresponding patient-side computing device, as shown in diagram (a) of FIG. 4B.

Diagram (b) of FIG. 4A shows a user interface presented on a screen (e.g., 132 of FIG. 1) of a patient-side computing device, e.g., Device 4. For example, the UI can be presented after the patient-side computing device is turned on and logged in by the operator. The UI can show a button "Begin" that can be clicked, e.g., by the operator, to start a session. After the button "Begin" is clicked, the patient-side computing device is connected to the cloud server, e.g., to the web portal. The cloud server can associate the patient-side computing device with the operator based on an identifier of the patient-side computing device, e.g., as shown in FIG. 2D. Once the patient-side computing device is successfully connected to the cloud server, the UI presented on the patient-side computing device can show information of an access code, e.g., "5678", generated by the web portal for connection with the operator-side computing device, as shown in diagram (b) of FIG. 4B. The operator can get the access code from the UI presented on the patient-side computing device and input it on the UI presented on the operator-side computing device, then submit the access code to the web portal. After the web portal confirms the access code input in the operator-side computing device matches with the access code generator for the patient-side computing device, the web portal can establish a wireless connection between the operator-side computing device and the patient-side computing device.

Figure 4B:
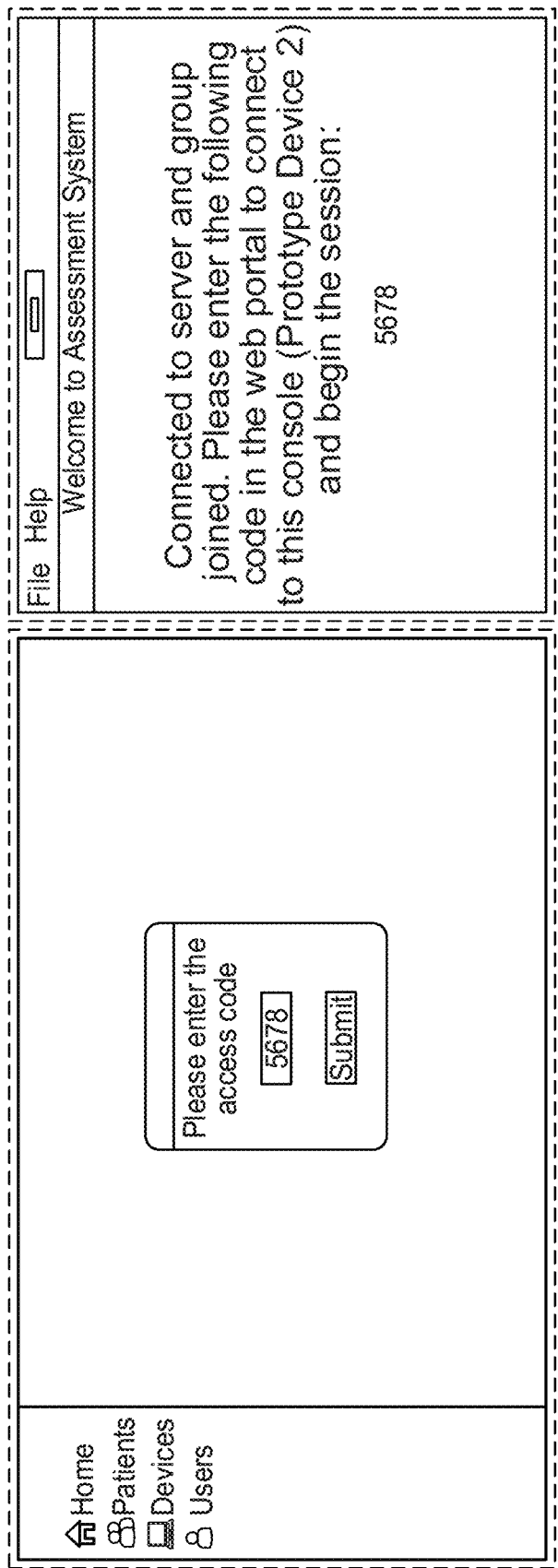
Figure 4C:
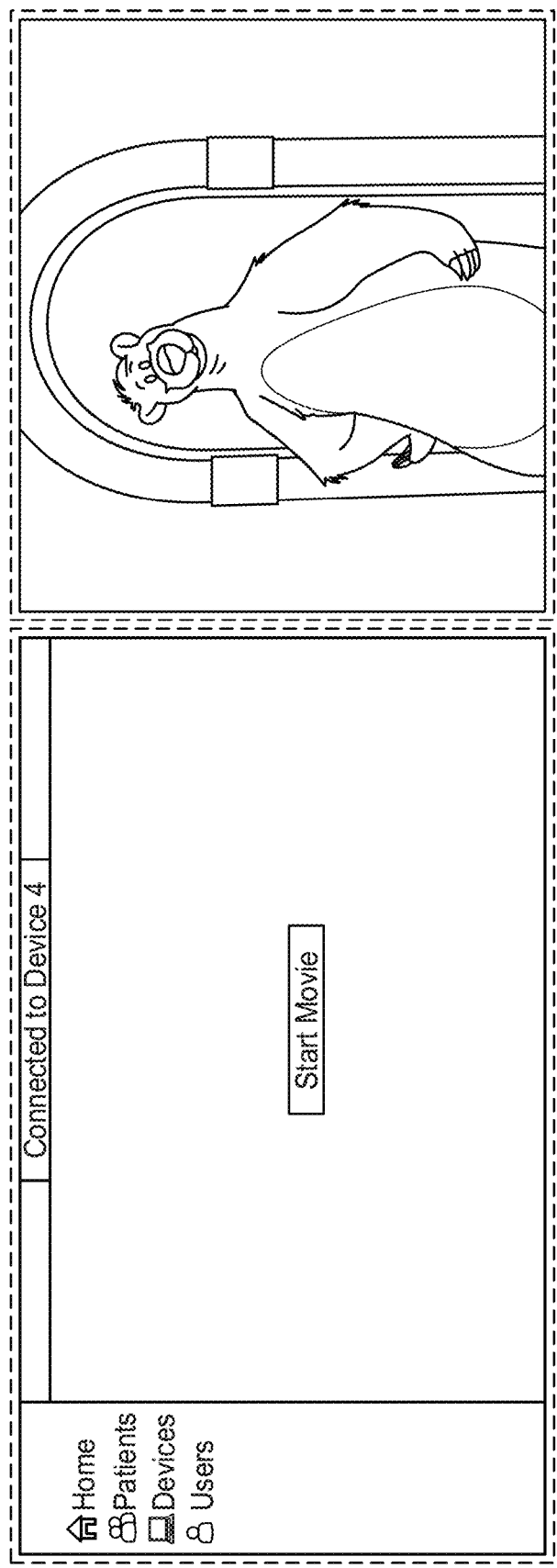

Once the connection between the operator-side computing device and the patient-side computing device (e.g., Device 4) is established, connection information, e.g., "Connected to Device 4", can be displayed on the UI of the operator-side computing device, e.g., as illustrated in diagram (a) of FIG. 4C. Meanwhile, the UI can show a button for starting displaying visual information, e.g., movies, on the screen of the patient-side computing device to a patient. A caregiver of the patient, e.g., a parent, can bring (or carry) the patient to watch the movies presented on the screen of the patient-side computing device.

At step 304, desensitization begins, e.g., by the operator clicking the button "start movie" on the UI of the operator-side computing device, which can cause displaying visual desensitization information (e.g., movie) on the screen of the patient-side computing device to the patient, as illustrated in diagram (b) of FIG. 4C.

During the display of the desensitization movie, data are generally not recorded. Instead, the movie is displayed to gain the attention of the patient. The movie may reflexively cause exogenous cueing by the patient without the need for verbal mediation or instruction by the operator. For example, the operator need not give instructions to look at the screen of the patient-side computing device because the movie itself captures the patient's attention.

Figure 4D:
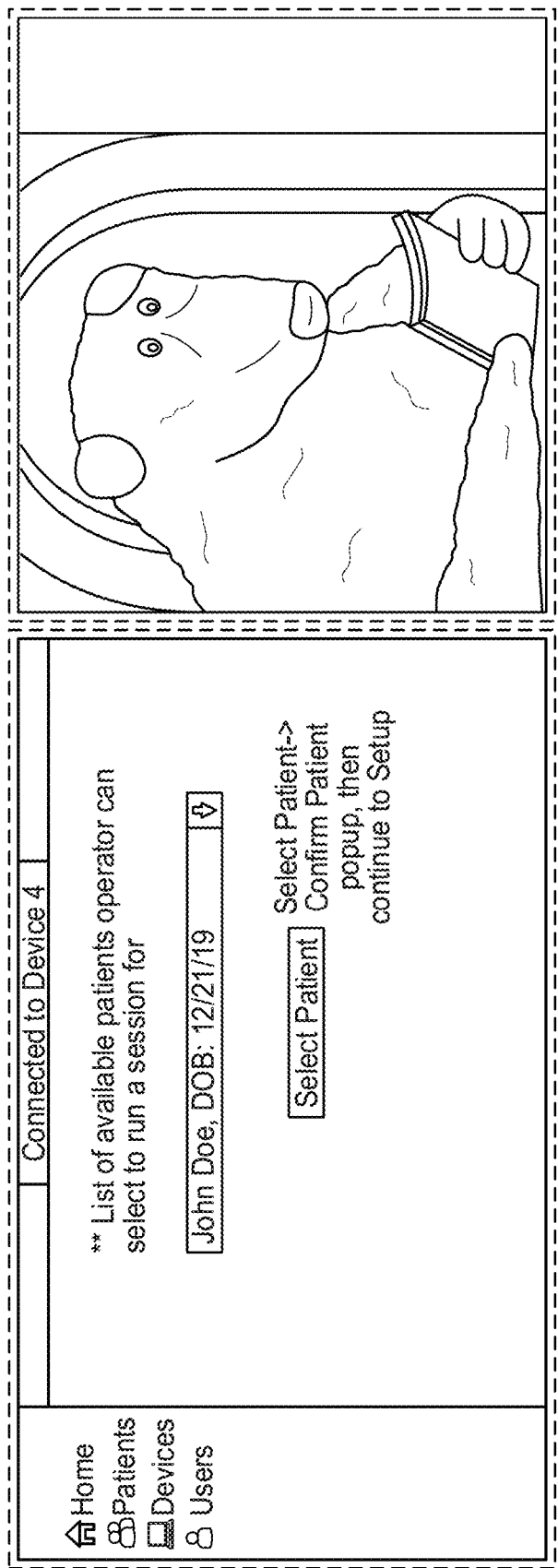

While the desensitization movie is displayed on the screen of the patient-side computing device, as shown in diagram (b) of FIG. 4D, the operator can select patient information of the patient through the UI of the operator-side computing device, as shown in diagram (a) of FIG. 4D. The operator can select a patient from a list of existing patients associated with the operator in the cloud server, e.g., as shown in FIG. 2D, or create a patient profile for a new patient. After the patient is confirmed, the process starts to setup the eye-tracking device (or the patient-side computing device) with respect to the patient, by showing setup information on the UI of the operator-side computing device, as illustrated in diagram (a) of FIG. 4E. The operator can also select "Pause Movie" or "Skip Movie" on the UI of the operator-side computing device.

Figure 4E:
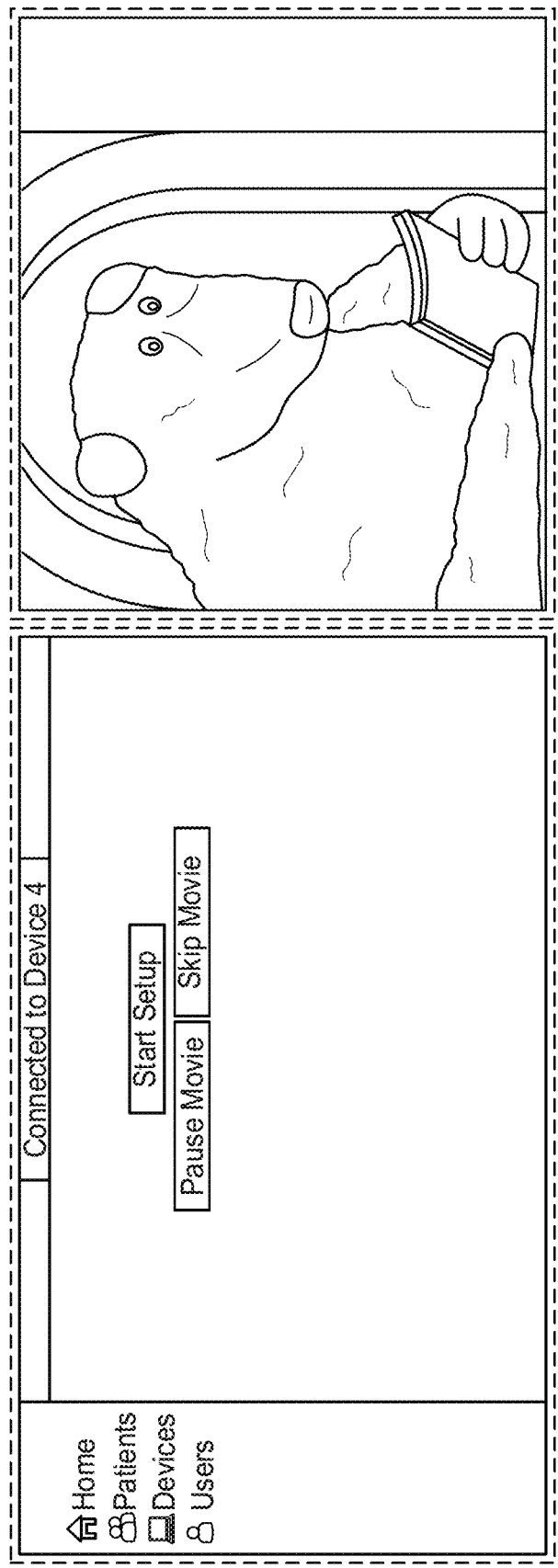
Figure 4F:
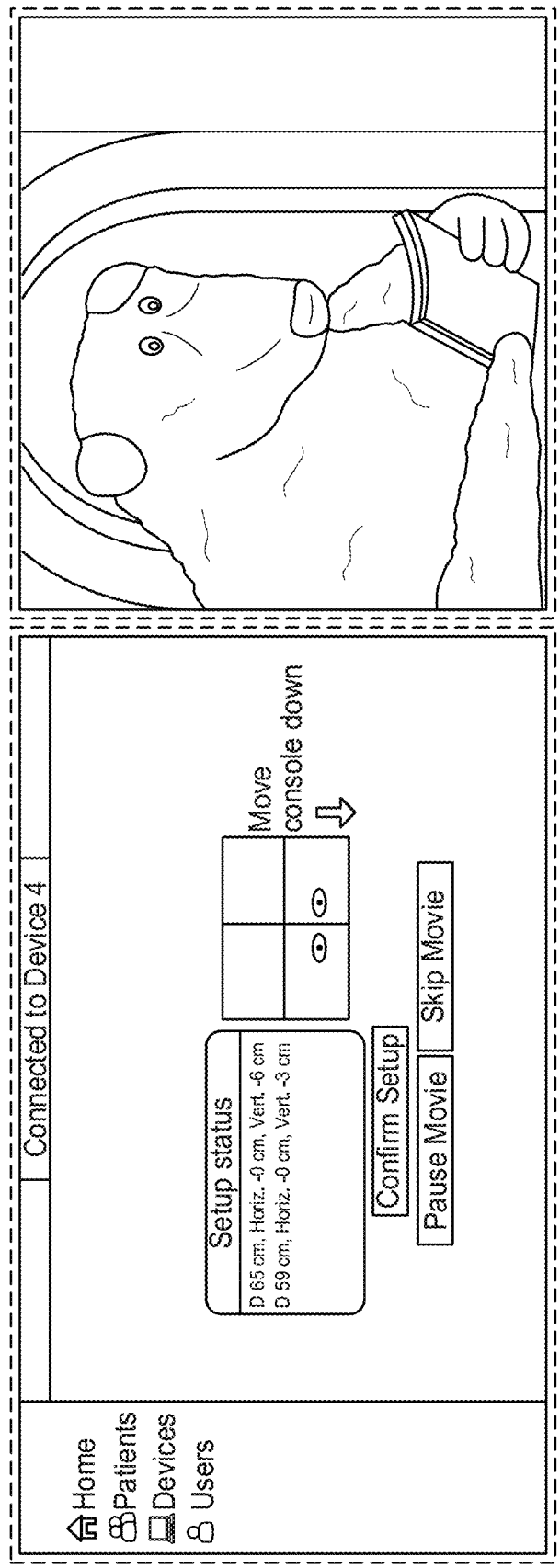

During the setup, the desensitization movie can be kept playing on the screen of the patient-side computing device, as illustrated in diagram (b) of FIG. 4E and diagram (b) of FIG. 4F. As shown in diagram (a) of FIG. 4F, on the UI of the operator-side computing device, a relative position between the eye-tracking device and eyes of the patient is shown, e.g., by text or graphically. The relative position can be determined by capturing image data of the eyes of the patient using an image acquisition device (e.g., a camera) included in or adjacent to the eye-tracking device. In some embodiments, after the operator clicked the button "Start Setup" in the UI of the operator-side computing device, as shown in diagram (a) of FIG. 4E, the operator application running on the cloud server can send a command to the patient-side computing device to capture an image of the eyes of the patient using the image acquisition device. The patient-side computing device can then transmit the captured image to the cloud server, and the operator application can process the image to determine a relative position between the eye-tracking device and the eyes of the patient. The relative position can include a distance between the eye-tracking device and the eyes of the patient, a horizontal and/or vertical deviation between a center of the eyes and a center of a field of view (or a detection area) of the eye-tracking device. Based on the relative position, the operator application can show an instruction for adjusting a position of the eye-tracking device, e.g., "Move console down", on the UI of the operator-side computing device, as shown in diagram (a) of FIG. 4F. Once the relative position of the eyes of the patient and the eye-tracking device is acceptable, the operator can confirm the setup, e.g., by clicking the button for "Confirm Setup" in the UI. In some embodiments, in response to determining that the relative location of the eyes of the patient and the eye-tracking device is smaller than a predetermined threshold (e.g., the horizontal/vertical deviation is smaller than 0.1 cm), the operator application can determine that the setup is completed and show an indication to the operator.

At step 306, the patient is calibrated with the eye-tracking device. After the setup is completed, the operator application can present a button for "Start Calibration" on the UI of the operator-side computing device, as shown in diagram (a) of FIG. 4G. In some embodiments, a calibration involves a patient looking at one or more fixed, known calibration targets (e.g., points or icons) in a visual field. The calibration or fixation target reflexively captures the patient's attention and results in a saccade towards, and fixation upon, a known target location. The target reliably elicits fixations to a finite location; for example, a radially symmetric target spanning less than 0.5 degrees of visual angle. Other examples include concentric patterns, shapes, or shrinking stimuli that, even if initially larger in size, reliably elicit fixations to fixed target locations.

Figure 4G:
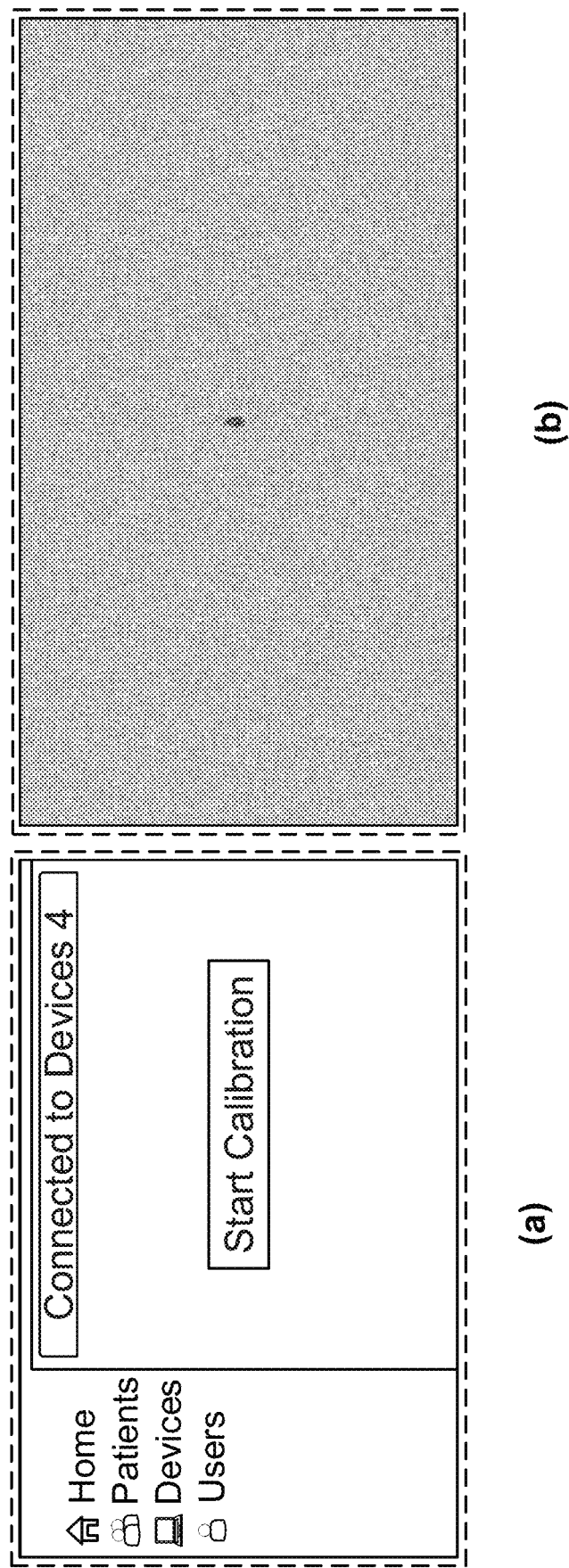

For example, once the operator clicks the button to start the calibration, a plurality of calibration targets can be sequentially presented at predetermined locations (or target locations) (e.g., a center, a left top corner, or a right bottom corner) on the screen of the patient-side computing device, e.g., as shown in diagram (b) of FIG. 4G. While presenting the plurality of calibration targets on the screen of the patient-side computing device, the eye-tracking device can be activated to capture eye-tracking calibration data of the patient, e.g., in response to receiving a command from the operator application. An eye-tracking application (e.g., 214 of FIG. 2A) can run on the patient-side computing device to collect the eye-tracking calibration data of the patient.

In some embodiments, the patient-side computing device (e.g., the eye-tracking application) is configured to determine a position of a corresponding visual fixation of a calibration target and then compare the determined position of the corresponding visual fixation of the patient with a predetermined location where the calibration target was presented. Based on a result of the comparison, the eye-tracking application can determine whether the calibration target is calibrated. If a distance between a position of the corresponding visual fixation of the patient and the predetermined location for a calibration target is within a predetermined threshold, the eye-tracking application can determine that the corresponding visual fixation of the patient matches with the predetermined location for the calibration target, or the calibration target is calibrated. If the distance is greater than or identical to the predetermined threshold, the eye-tracking application can determine that the corresponding visual fixation of the patient does not match the predetermined location, or the calibration target fails the calibration.

In some embodiments, the patient-side computing device transmits information about the captured eye-tracking calibration data of the patient and/or the predetermined locations to the operator-side computing device or the cloud server, the operator application can determine the positions of the corresponding visual fixations of the patient and compare the determined positions with the plurality of predetermined locations, and/or determine whether a calibration target is calibrated based on a result of the comparison.

In some embodiments, a first calibration target can be first presented at a center of the screen, and the calibration can continue with four more calibration targets presented at each corner of the screen along a rotating direction. The operator application can alert the operator the active status of calibration, e.g., calibrating point 1, calibrating point 2, calibrating point 3, or calibration complete 4/5 targets). Between each calibration target, a desensitization movie plays for a set period of time before a new calibration target is shown. Each calibration target can loop a set number of times before determining that the calibration target fails to be calibrated and moving on to the next calibration target. If a calibration target fails the calibration, it can be reattempted after all remaining calibration targets are shown and gaze collection attempted.

At step 308, the calibration is validated. The validation can be performed to measure the success of the calibration, e.g., by showing new targets and measuring the accuracy of the calculated gaze. The validation can show a smaller number of calibration targets, e.g., 3, than that for the calibration step 306, e.g., 5. A desensitization movie can be played between showing two adjacent calibration targets.

In some embodiments, based on the result of the comparison between determined positions of the corresponding visual fixations of the patient with predetermined locations where the calibration targets were presented, initial validations with varying levels of success (e.g., number of calibration targets calibrated or validated) can automatically instruct the operator to (1) recalibrate the eye-tracking device with the patient, (2) revalidate those calibration targets which could not be validated, or (3) accept the calibration and continue to data collection at step 310.

Figure 4H:
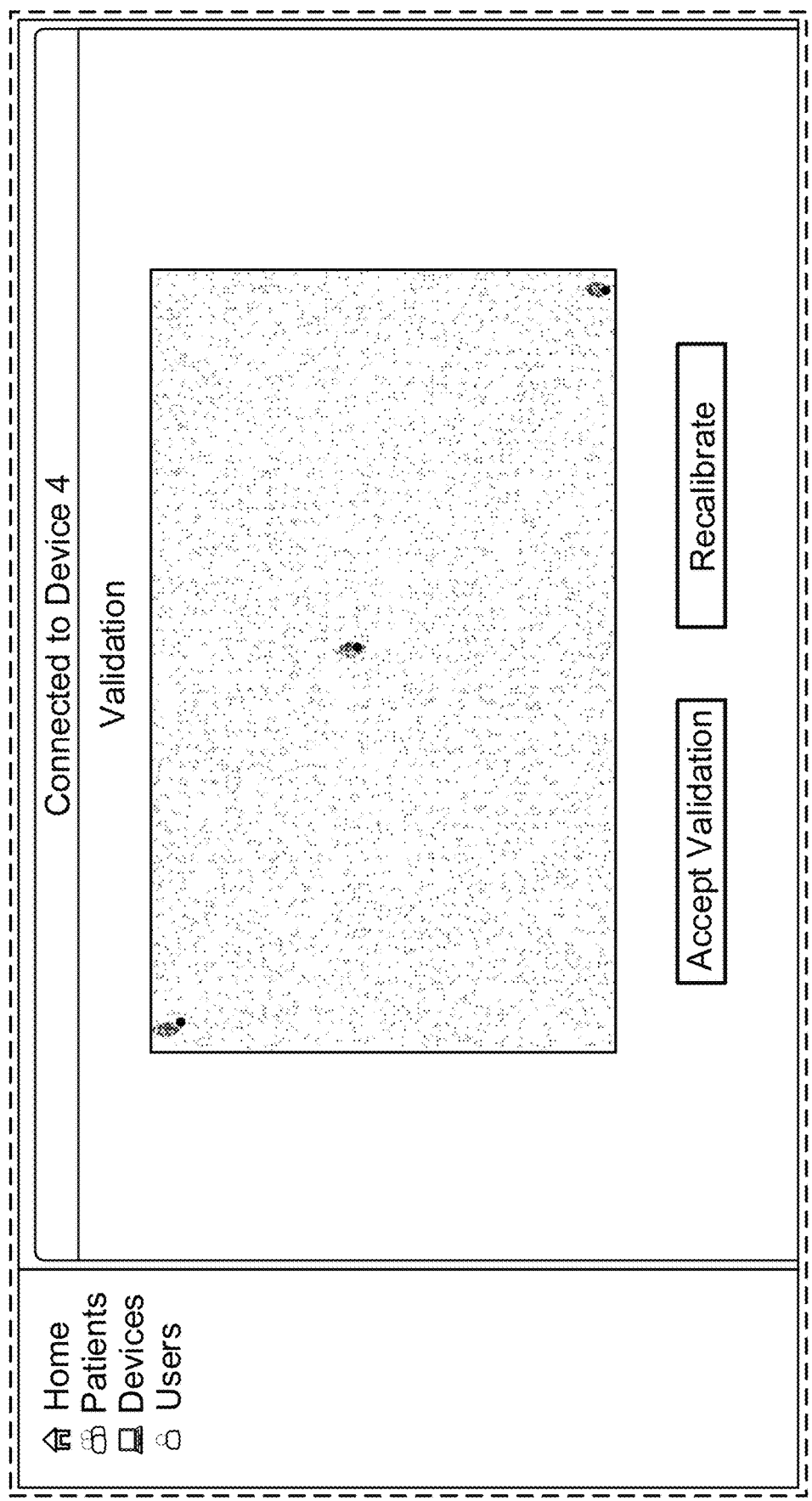

In some embodiments, the operator may have a discretion to decide whether to accept the calibration. As shown in FIG. 4H, on the display screen of the operator-side computing device, the calibration targets are simultaneously presented at the plurality of predetermined locations with representations (e.g., points) of the corresponding visual fixations of the patient at the determined positions of the corresponding visual fixations of the patient. The UI can also show a first button for "Accept Validation" and a second button for "Recalibrate". The operator can view the matching between the plurality of calibration targets and the representations of the corresponding visual fixations of the patient and determine whether to accept validation (by clicking the first button) or recalibrate the patient to the eye-tracking device (by clicking the second button).

At step 310, eye-tracking data of the patient is collected, e.g., after the calibration is validated or the operator accepts the validation, by presenting a playlist of predetermined visual stimuli (e.g., stimuli movies) to the patient on the screen of the patient-side computing device. As shown in FIG. 5(*a*), the list of predetermined visual stimuli can include a number of social stimuli videos (e.g., 0075PEER, 0076PEER, 0079PEER) specific to the patient, e.g., based on the patient's age and/or condition. Between each social stimuli videos or before presenting each social stimulus video, a centering video (e.g., a centerstim video) can be shown for briefly centering gaze of the patient. In some embodiments, as shown in FIG. 5(*a*), a calibration check (e.g., similar to that at step 306) is performed in the data collection step, e.g., between showing centering videos. For example, the calibration check can include showing five calibration targets, CCTL for calibration check top left, CCTR for calibration check top right, CCBL for calibration check bottom left, CCCC for calibration check center-center, CCBR for calibration check bottom right. Data related to the calibration check can be used in post hoc processing, e.g., for recalibrating eye-tracking data and/or for determining a calibration accuracy.

Figure 4I:
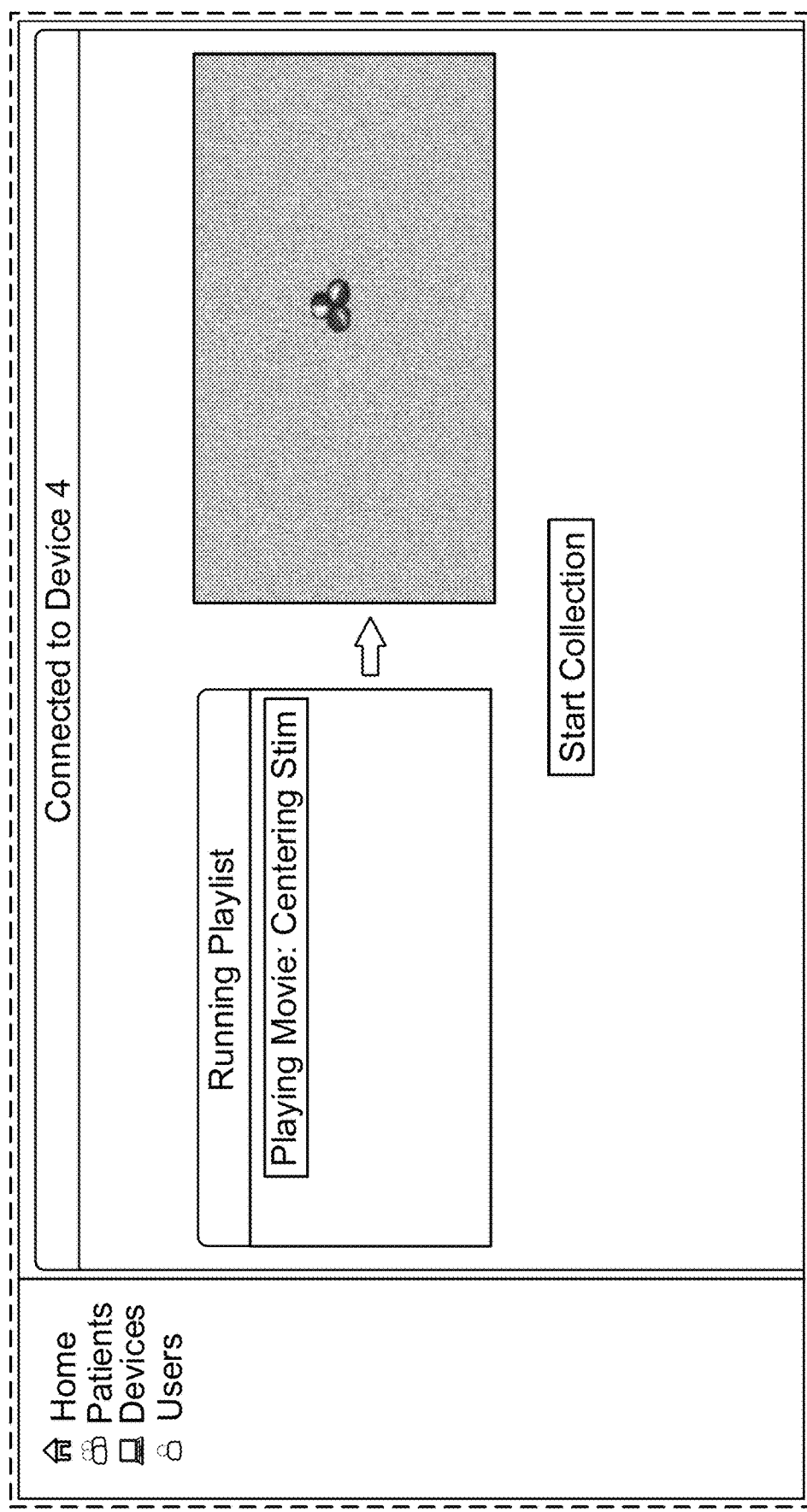

In a particular example, a sequence of data collection at step 310 can be as follows:
1. Centering stim
2. Stimuli movie
3. Centering Stim
4. Stimuli Movie or calibration check (e.g., displaying 5 calibration targets such as randomly played between 2 to 4 stimuli movies)
5. Repeat steps 1-4 until the playlist of predetermined stimuli movies completes In some embodiments, as shown in FIG. 4I, the UI on the operator-side computing device shows a button for "Start Collection". After the operator clicks the button for "start collection", the playlist of predetermined visual stimuli can be sequentially presented on the screen of the patient-side computing device according to a predetermined sequence. On the screen of the operator-side computing device, as shown in FIG. 4I, the UI can show a status of running the playlist in text (e.g., playing movie: centering stim) or showing a same content (e.g., showing a centering stim video) as that presented on the screen of the patient-side computing device.

Figure 4J:
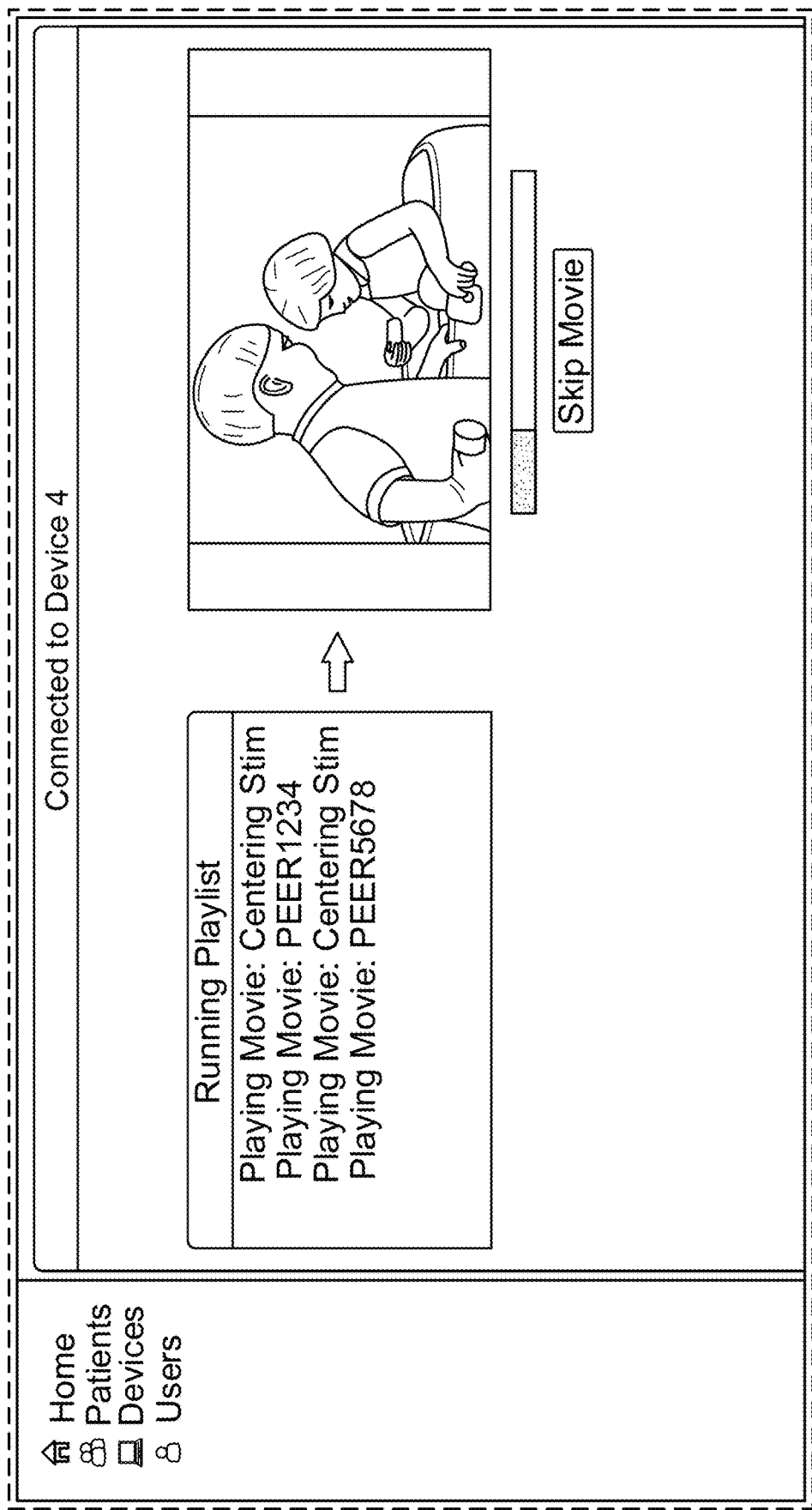

In some embodiments, as shown in FIG. 4J, the UI can show a running playlist of videos that have been played or being played, e.g., Centering Stim, PEER1234, Centering Stim, PEER5678. The UI can also show the video that is being presented on the screen of the patient-side computing device. The UI can also show a progress bar indicating a percentage of stimuli movies that have been played among the playlist of predetermined stimuli movies. The UI can also show a button for the operator to skip movie.

In some embodiments, calibration accuracy of collected eye-tracking data (e.g., 812 of FIG. 8A) can be assessed, e.g., via the presentation of visual stimuli that reflexively capture attention and result in a saccade towards, and fixation upon, a known target location. The target reliably elicits fixations to a finite location; for example, a radially symmetric target spans less than 0.5 degrees of visual angle. Other examples include concentric patterns, shapes, or shrinking stimuli that, even if initially larger in size, reliably elicit fixations to fixed target locations. Such stimuli may be tested under data collection with head restraint to ensure that they reliably elicit fixations under ideal testing circumstances; then their use can be expanded to include non-head-restrained data collection.

In some embodiments, numerical assessment of the accuracy of collected eye-tracking data may include the following steps: (1) presenting a fixation target that reliably elicits fixation to a small area of the visual display unit; (2) recording eye-tracking data throughout target presentation; (3) identifying fixations in collected eye-tracking data; (4) calculating a difference between fixation location coordinates and target location coordinates; and (5) storing the calculated difference between fixation location coordinates and target location coordinates as vector data (direction and magnitude) for as few as one target or for as many targets as possible (e.g., five or nine but can be more). In some embodiments, recalibrating or post-processing step can be executed, e.g., by applying spatial transform to align fixation location coordinates with actual target location coordinates, by approaches including but not limited to (a) Trilinear interpolation, (b) linear interpolation in barycentric coordinates, (c) affine transformation, and (d) piecewise polynomial transformation.

Once the playlist of predetermined visual stimuli is completely played, the session ends. The patient-side computing device can generate session data based on raw eye-tracking data collected by the eye-tracking device, e.g., storing the raw eye-tracking data with associated information (timestamp information) in a data file (e.g., in .tsv format, .idf format, or any suitable format), as illustrated in FIG. 5(*b*). The raw eye-tracking data can include values for a number of eye-tracking parameters at different timestamps. The eye-tracking parameters can include gaze coordinate information of left eye, right eye, left pupil, and/or right pupil.

The session data can also include information of played or presented visual stimuli in another data file (e.g., in .tsv format or any suitable format), as illustrated in FIG. 5(*a*). The information can include timestamp information and name of each visual stimulus played. The timestamp information of visual stimuli can be associated with the timestamp information of the eye-tracking data, so that eye-tracking data for each visual stimulus (and/or calibration check) can be individually determined based on the timestamp information in these two data files.

At step 312, session data is sent to the cloud server. Once the session data is generated by the patient-side computing device, the patient-side computing device can transmit the session data to the cloud server. As discussed in FIGS. 2A-2G and with further details in FIGS. 6, 7A-7B, and 8, the cloud server can first store the session data in a centralized database, e.g., the database 226 of FIGS. 2A-2B, then process the session data, analyze the processed data, and generate a diagnostic result of the patient, which can be accessible or viewable by the operator or a medical professional.

Example Data Processing and Analysis

FIG. 6 is a flowchart of an example process 600 for managing session data, e.g., data processing and analysis, by a cloud server (e.g., the cloud server 110 of FIG. 1 or the cloud server as described in FIGS. 2A-2G), according to one or more embodiments of the present disclosure. FIGS. 7A-7B show a flowchart of an example process 700 for managing session data by the cloud server with more details than FIG. 6, according to one or more embodiments of the present disclosure.

At step 702, once a session is complete, a corresponding patient-side computing device (e.g., 130 of FIG. 1) or eye tracking console (e.g., 212 of FIGS. 2A-2G) transmits session data of the session to a cloud platform of the cloud server, e.g., through a web portal. The cloud platform can be the platform 112 of FIG. 1 or the platform subsystem 220 of FIGS. 2A-2G. In response to receiving the session data, the cloud platform of the cloud server stores the session data in a database (e.g., the database 226 of FIGS. 2A-2G) in the cloud platform. Then, the cloud platform automatically transfers the session data to a data pipeline system (e.g., 114 of FIG. 1 or 230 of FIGS. 2A-2G) for data processing and analysis.

At step 704, file pointers for session data of sessions are added to a processing queue (step 704). Session data of all completed sessions wait for processing according to the processing queue. As soon as session data of a session is uploaded and stored in the cloud server, a corresponding file pointer can be assigned to the session data of the session and added in the processing queue. A file pointer can be an identifier for session data of a respective session. The session data of the respective session can be retrieved from the database in the cloud platform based on the file pointer.

At step 706, a respective container is created for session data of each session, e.g., based on auto scaling technology, which can implement session parallelization. For example, in response to adding a file pointer for a new session into the processing queue, a new container can be created for the new session. Each container (e.g., 231 of FIG. 2C) can have its own instance of data processing module and data analysis module, e.g., as illustrated in FIG. 2C.

In each container, steps 708 to 714 are performed for session data of a corresponding session, e.g., by data processing module 232 of FIGS. 2A-2G. Note that steps 708 to 714 can be performed for session data of multiple sessions in multiple containers in parallel.

At step 708 (corresponding to step 602 of FIG. 6), the session data is obtained from the database in the cloud platform using a corresponding file pointer. As noted above, the session data can include two files: eye-tracking data file (e.g., as illustrated in FIG. 5(b)) and a playlist file (e.g., as illustrated in FIG. 5(a)).

Referring to FIG. 6, step 602 can correspond to step 708. At step 604, the session data is prepared for processing. Step 604 can include one or more steps as described in steps 710 to 714 of FIG. 7.

Step 604 can include linking eye-tracking data in the eye-tracking data file to movies played in the playlist file. In some embodiments, as illustrated in FIG. 7A, at step 710, the eye-tracking data is broken up into separate runs, e.g., based on timestamp information in these two files. Each run can correspond to playing a corresponding movie (e.g., the centering target, a predetermined visual stimuli, or one or more calibration targets). For example, eye-tracking data corresponding to timestamps within a range defined by timestamps of two adjacent movies is included in a run. At step 712, eye-tracking data in each run is linked to the corresponding movie from the playlist, based on timestamp information in these two files. In some embodiments, the eye-tracking data are not broken up into separate runs, instead, are processed as a continuous stream with data samples linked to corresponding movies in the playlist.

At step 714, eye-tracking data is recalibrated to account for drift or deviation. In some embodiments, eye-tracking data collected in the calibration step during presenting the playlist, e.g., as illustrated in diagram (a) of FIG. 5, can be used to calibrate or align the eye-tracking data collected during playing individual movies in the different runs. For example, with data from times adjacent to when additional calibration targets were shown, any discrepancies in gaze position are corrected. Some larger discrepancies may exclude certain data from subsequent analysis.

At step 606, the prepared session data is processed. In some embodiments, the data processing module extracts relevant information, e.g., visual fixation of the patient and/or visual fixations to objects or regions of interest in the movie, from the prepared session data. In some embodiments, data are resampled to account for any variance in time between samples. The data can be resampled using any suitable interpolation and/or smoothing technique. The data can be converted from a specified original resolution and/or coordinate system of the collected eye-tracking data to an appropriate resolution and/or coordinate system for analysis. For example, raw data can be collected at a higher resolution (e.g., 1024×768 pixels) than that of the presented stimuli (e.g., rescaled to 640×480 pixels). In some embodiments, the data processing module can automatically identify basic oculomotor events (unwanted fixations, saccades, blinks, off-screen or missing data, etc.), and can automatically identify times at which the subject was fixating (in an undesirable way), saccading, blinking, or times when the subject was not looking at the screen. The data processing module can adjust for aberrations in gaze position estimations as output by the eye-tracking device.

In some embodiments, as illustrated in step 716 of FIG. 7B, session data for multiple sessions of patients are processed in multiple session containers in parallel with preloading corresponding model data for the patients into the multiple session containers. In some examples, the session data of the multiple sessions are being processed in the multiple session containers using a majority of processing units (e.g., N processing cores) in the cloud server, while the corresponding model data are pre-loaded into the multiple session containers in parallel, using a minority of the processing units (e.g., M processing cores) in the cloud server. A processing unit or core can be a central processing unit (CPU). The parallelization can avoid additional time for waiting for uploading the model data.

The cloud server can pre-store model data in the database, e.g., 226 of FIGS. 2A-2G. The model data can include data of a large number of instances of significant difference in gaze position for patients (e.g., infants, toddlers or children) across varying levels of social, cognitive, or developmental functioning. Corresponding model data for a patient can include data related to the patient at a similar age, a similar background, and/or a similar condition, which can be used with processed session data for the patient to generate a diagnostic result for the patient. The corresponding model data for the patient can be identified and retrieved from the database, e.g., based on the age of the patient, the background of the patient, and/or the condition of the patient. Step 608 of the process 600, at which processed data is prepared for analysis, can include obtaining the processed data in the multiple session containers and pre-loading the corresponding model data in the multiple session containers.

At step 610, processed data is analyzed to generate an analyzed result. In some embodiments, for a session, the processed data is compared with corresponding model data in a corresponding session container to get a comparison result. In some embodiments, the data analysis module generate a result using the processed data and the corresponding model data, e.g., using comparison or inference via statistical models, algorithms, artificial intelligence (AI) models such as machine learning or artificial neural network models. In some embodiments, as illustrated in step 718 of FIG. 7B, in the multiple session containers, processed session data and pre-loaded model data are analyzed in parallel using a total number of processing units, e.g., N+M cores.

In some embodiments, processed session data are compared with corresponding data models to determine a level of a developmental, cognitive, social, or mental condition. A generated score is then compared to predetermined cutoff or other values to determine the patient's diagnosis of ASD, as well as a level of severity of the condition. In certain other embodiments, a patient's point-of-gaze data (e.g., visual fixation data) is analyzed over a predetermined time period (e.g., over multiple sessions spanning several months) to identify a decline, increase, or other salient change in visual fixation (e.g., point-of-gaze data that initially corresponds to that of typically-developing children changing to more erratic point-of-gaze data corresponding to that of children exhibiting ASD, or point-of-gaze data that becomes more similar to typically-developing children in response to targeted therapy).

Figure 8A:
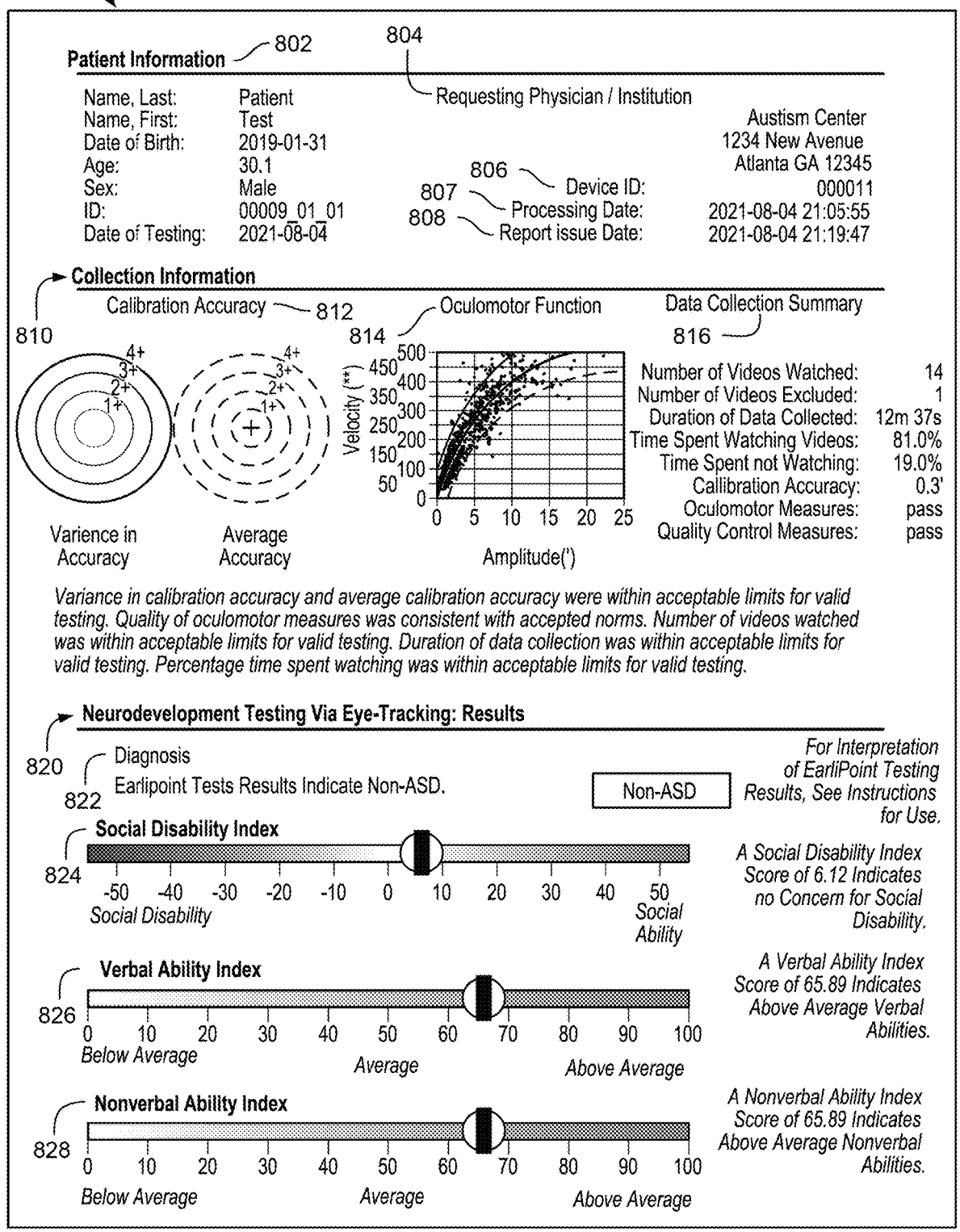
FIG. 8A illustrates an example result interface displaying at least one index value based on eye-tracking data, according to one or more embodiments of the present disclosure.

At step 720 (corresponding to step 612), a summary of results is calculated. As noted above, the analyzed result can be used to determine a score for at least one index, e.g., social disability index, verbal ability index, nonverbal ability index, social adaptiveness index, and/or social communication index. Based on a comparison of the score with at least one predetermined cutoff value, the patient's diagnosis of ASD, as well as a level of severity of the condition can be calculated. For example, as illustrated in FIG. 8A, based on the analyzed result and/or any other suitable information (e.g., from other related analysis on the patient), a social disability index score of 6.12 is shown in a range from −50 (social disability) to 50 (social ability) and indicates no concern for social disability; a verbal ability index score of 85.89 is shown in a range from 0 to 100 and indicates above average verbal abilities; a nonverbal ability index score of 85.89 is shown in a range from 0 to 100 and indicates above average nonverbal abilities. Moreover, a diagnosis of Non-ASD can be also calculated based on the analyzed data.

In some embodiments, a summary of results includes a visualization of the individual's eye-tracking data (e.g., point-of-gaze data) overlaid on movie stills from socially relevant moments, allowing clinicians and parents to better understand how the patient visually attends to social information. For example, at step 610, the movie stills for which the patient has usable data can be cross-referenced against the list of movie stills that have been pre-determined to elicit eye-gaze behavior with information about diagnostic status, including symptom severity. The visualization can also include a visualization of aggregated reference data from typically developing children, for example, matched on patient attributes such as age, sex, etc. These visualizations can be side-by-side so that the clinician and/or parent can compare the individual patient data to the reference data, and see how gaze pattern align or diverge. These visualizations may include annotations explaining movie content, eye-gaze patterns, and more.

In some embodiments, a summary of the results includes an animation visualizing the patient's eye-tracking data overlaid on movie stills from socially relevant moments. For example, the web portal may contain a dashboard that allows the clinician to view the stimulus movie shown the patient, with their eye-gaze data overlaid. The dashboard may be configurable to allow the user to select which movies to visualize, and whether to visualize frames that capture information about the social disability index, verbal ability index, non-verbal index, or any other index calculated in the report.

With continued reference to FIG. 7B, at step 722, a result output is returned to the web portal, e.g., as illustrated in FIG. 2B, by the data pipeline subsystem. In some embodiments, the result output includes three files: one containing processed eye-tracking data, one containing a summary of eye tracking statistics, and one containing the diagnostic information (e.g., the summary of results). The three files can then be uploaded to the database (e.g., 226 of FIGS. 2A-2G) for storage. In some cases, the processed eye-tracking data are tabulated into a session table. Summary of eye tracking information (e.g., fixation samples/movie, etc.) can be read from the processed summary file and tabulated in the database for subsequent query. Summary values (e.g., percentage fixation/movie, etc.) can be then calculated within the database.

At step 724, the result output is reconnected with patient information to generate a diagnostic report or result for the patient. For example, the file containing diagnostic information can be uploaded to an application data database (e.g., 224 of FIGS. 2A-2G) to be associated with the patient in the application data, e.g., as illustrated in FIG. 2D. The diagnostic report or result can be presented to a user associated with the patient in the application data database (an operator or a medical professional such as a physician) or a caregiver associated with the patient in any suitable manner.

Figure 8B:
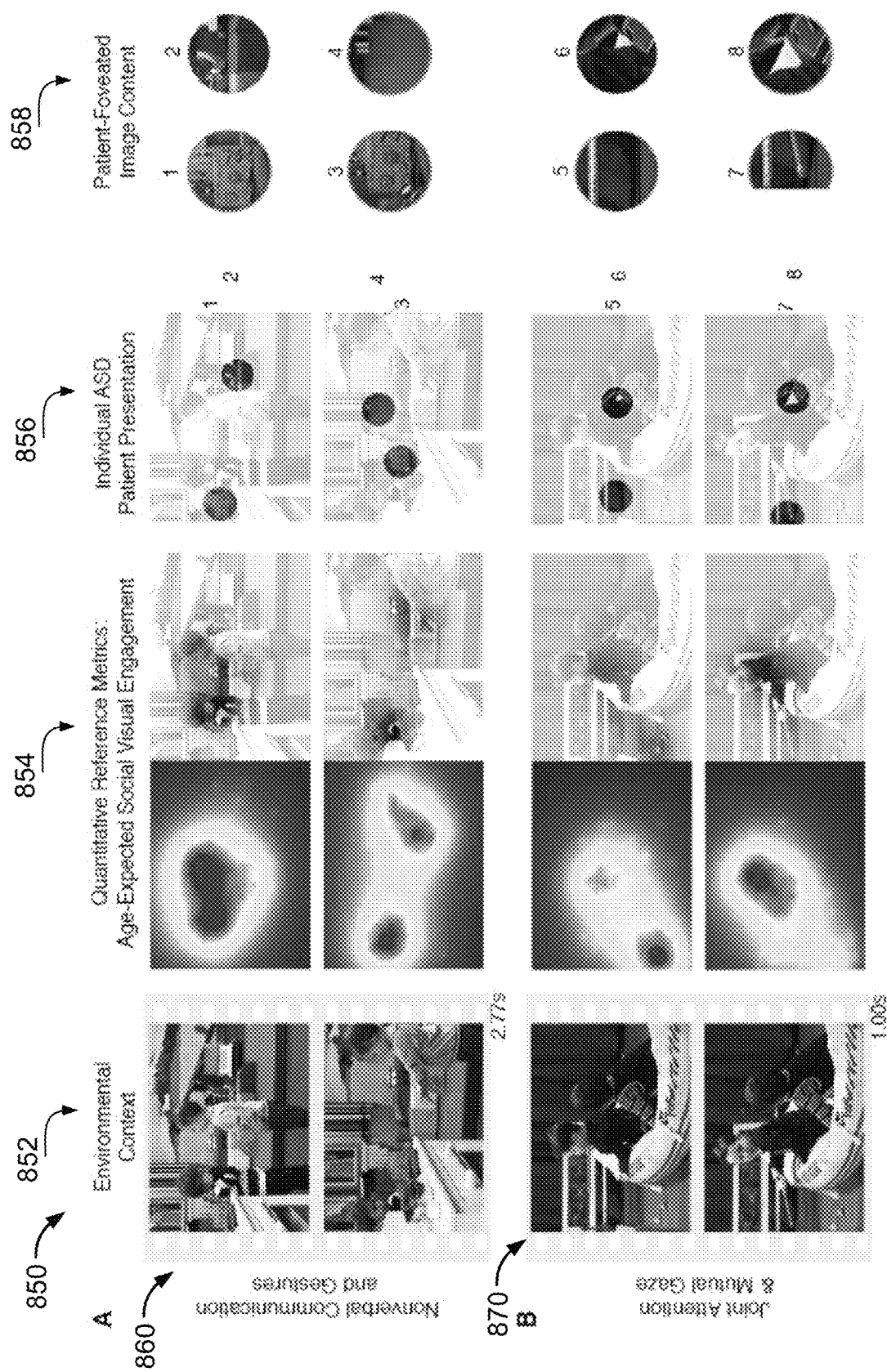
FIGS. 8B-8C illustrate another example result interface displaying performance-based measures of developmental assessment based on eye-tracking data, on instances of: Nonverbal Communication and Gestures (A) and Joint Attention & Mutual Gaze (B) in FIG. 8B, Facial Affect (C) and Pointing and Social Monitoring (D) in FIG. 8C, according to one or more embodiments of the present disclosure.
Figure 8C:
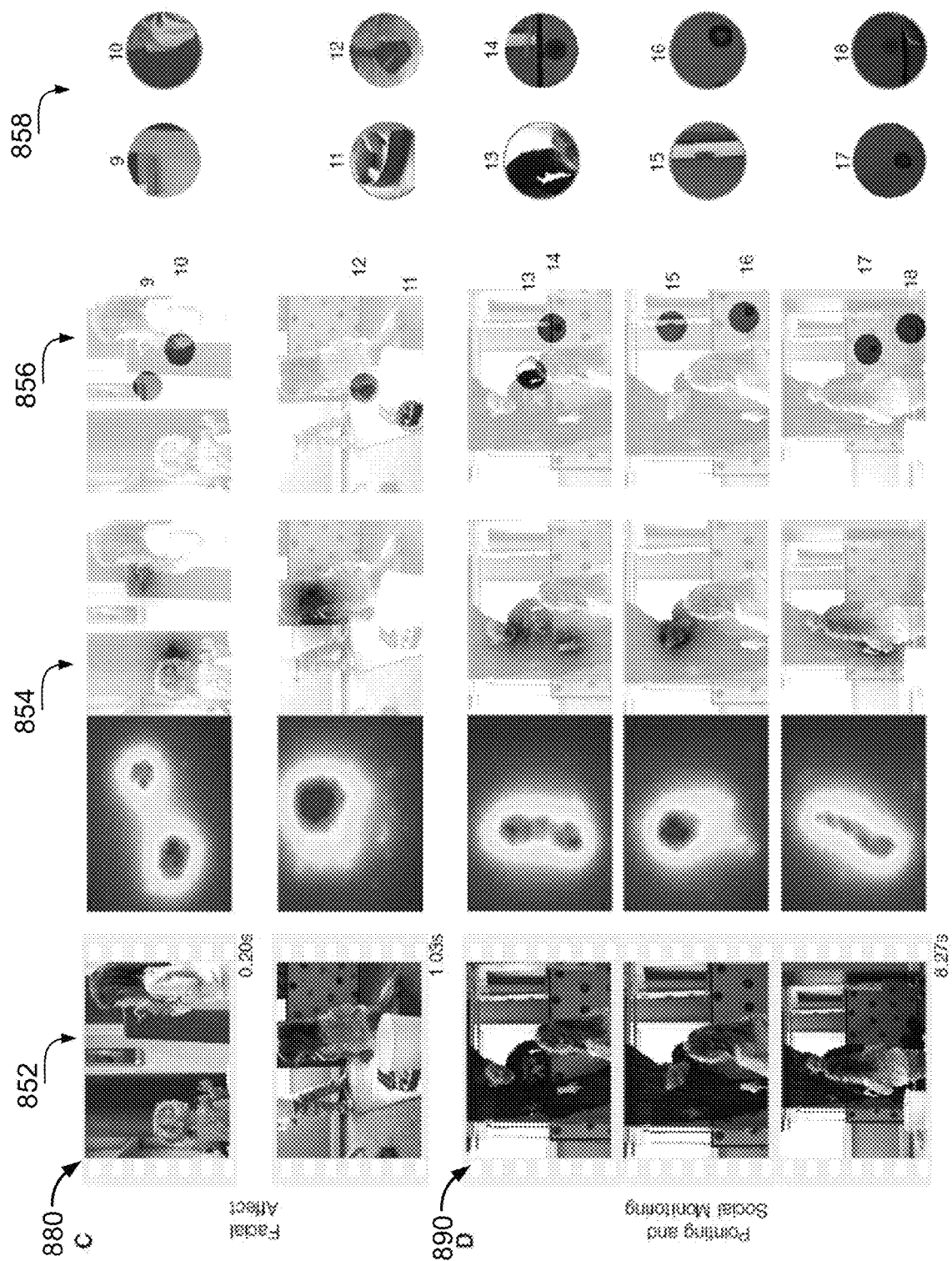

In some embodiments, once the diagnostic report or result for the patient is generated, the user can be notified (e.g., by email or message) to log in to view the diagnostic report or result through the web portal. The diagnostic report or result can be presented on a user interface, e.g., as shown in FIG. 8A, or FIGS. 8B-8C. In some embodiments, once the diagnostic report or result for the patient is generated, the diagnostic report or result can be sent to an operator-side computing device for presenting to the user. The diagnostic report or result can be also sent in a secure email or message to the operator. The diagnostic report or result can be stored in the application data database (e.g., 224 of FIGS. 2A-2G) and/or the database (e.g., 226 of FIGS. 2A-2G).

FIG. 8A illustrates an example result interface 800 displaying a diagnostic report or result including at least one index value based on eye-tracking data, according to one or more embodiments of the present disclosure. The result interface 800 shows patient information 802, requesting physician/institution information 804, device ID of a patient-side computing device 806, processing date 807 (indicating time for obtaining session data for processing), report issue date 808.

The result interface 800 also shows collection information 810 that includes calibration accuracy 812, oculomotor function 814, and data collection summary 816. The calibration accuracy 812 and the oculomotor function 814 can be presented graphically. The data collection summary 816 can include at least one of a number of videos watched, a number of videos excluded, a duration of data collected, time spent watching videos, time spent not watching, a calibration accuracy, oculomotor measures, or quality control measures.

The result interface 800 also shows neurodevelopmental testing result 820, which can include a diagnostic result 822 (e.g., ASD or Non-ASD), social disability index information 824, verbal ability index information 826, and nonverbal ability index information 828. The result interface 800 can graphically show these index information 824, 826, 828, with corresponding descriptions.

FIGS. 8B-8C illustrate another example result interface 850 displaying performance-based measures of developmental assessment on instances of: Nonverbal Communication and Gestures (A) and Joint Attention & Mutual Gaze (B) in FIG. 8B, Facial Affect (C) and Pointing and Social Monitoring (D) in FIG. 8C, according to one or more embodiments of the present disclosure.

The result interface 850 shows the performance-based measures of children's individual vulnerabilities and opportunities for skills development. Neurodevelopmental assessment via eye-tracking measures how a child engages with social and nonsocial cues occurring continuously within naturalistic environmental contexts (left column 852, shown as still frames from testing videos). In relation to those contexts, normative reference metrics provide objective quantification of non-ASD, age-expected visual engagement (middle column 854 shown as density distributions in both pseudocolor format and middle column 856 shown as color-to-grayscale fades overlaid on corresponding still frames). The age-expected reference metrics can be used to measure and visualize patient comparisons, revealing individual strengths, vulnerabilities, and opportunities for skills-building (right column 858, example patient data shown as overlaid circular apertures which encompass the portion of video foveated by each patient, for example, each aperture spans the central ~5.2 degrees of a patient's visual field). Individual patients with ASD present as not fixating on instances of (A) verbal and nonverbal interaction and gesture (860); (B) joint attention and mutual gaze cueing (870); (C) dynamic facial affect (880); and (D) joint attention and social monitoring (890). As shown in FIGS. 8B-8C, children with ASD present as engaging with toys of interest (1, 3, 5, 7); color and contrast cues (2, 6, 8); objects (10, 11, 12); background elements not directly relevant to social context (4, 9, 13); and recurrent visual features (14, 15, 16, 17, 18). Elapsed times at bottom right of still frames highlight the rapidly changing nature of social interaction: in approximately 12 minutes of viewing time, hundreds of verbal and nonverbal communicative cues are presented, each eliciting age-expected patterns of engagement and offering corresponding opportunities for objective, quantitative comparisons of patient behavior.

Example Processes

Figure 9:
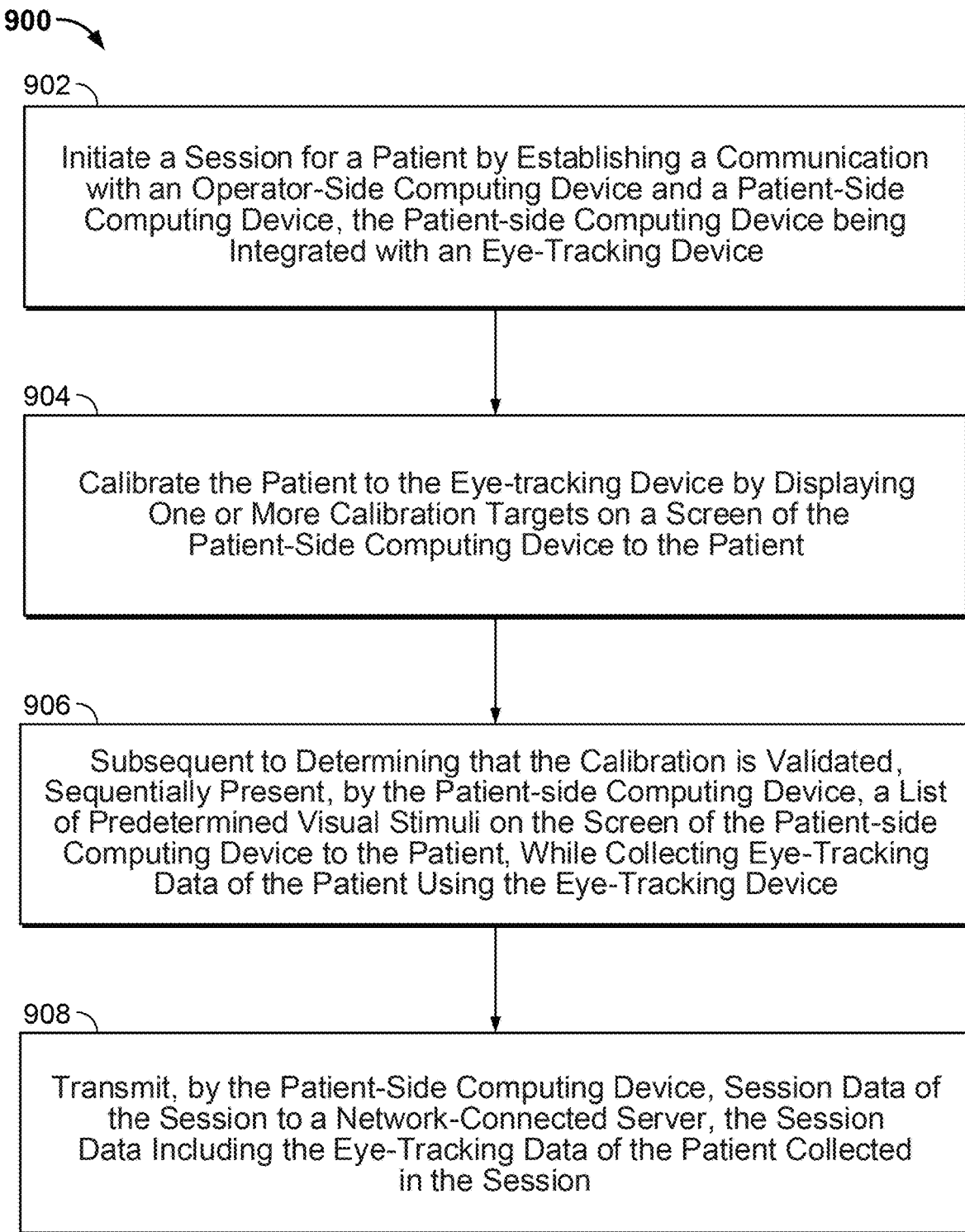
FIG. 9 is a flowchart of an example process for session data acquisition, according to one or more embodiments of the present disclosure.

FIG. 9 is a flowchart of an example process 900 for session data acquisition, according to one or more embodiments of the present disclosure. The process 900 can be performed by a system, e.g., the computing system 120 of FIG. 1 or the data acquisition subsystem 210 of FIGS. 2A-2G. The process 900 can be similar to the process 300 of FIG. 3 and can be described with reference to FIGS. 4A to 4J.

The system includes an operator-side computing device (e.g., 140 of FIG. 1) and one or more patient-side computing devices (e.g., 130 of FIG. 1) integrated with associated eye-tracking devices (e.g., 134 of FIG. 1). At least one of the operator-side computing device or the patient-side computing device can be a portable device. Each of the operator-side computing device and the one or more patient-side computing devices can communicate with a network-based server or a cloud server (e.g., the cloud server 110 of FIG. 1 or the cloud server as described in FIGS. 2A-2G) via a network (e.g., the network 102 of FIG. 1). The system can be associated with a treatment provider, e.g., providing developmental disorder assessment and/or treatment services to patients. The cloud server can be associated with a service provider for providing services, e.g., data processing, analysis, and diagnostic results, to treatment providers. The process 900 can include a number of steps, some of which is performed by the operator-side computing device, some of which is performed by the patient-side computing device and/or the eye-tracking device, and some of which are performed by a combination of the operator-side computing device and the patient-side computing device.

At step 902, a session for a patient is initiated by establishing a communication with the operator-side computing device and the patient-side computing device. In some embodiments, establishing the communication includes establishing a wireless connection between the operator-side computing device and the patient-side computing device, e.g., the wireless connection 131 of FIG. 1.

In some embodiments, establishing the wireless connection between the operator-side computing device and the patient-side computing device includes: accessing, by the operator-side computing device, a web portal (e.g., 222 of FIGS. 2A-2G) at the network-connected server, and in response to receiving a selection of the patient-side computing device in the web portal, wirelessly connecting the operator-side computing device to the patient-side computing device.

In some embodiments, establishing the wireless connection between the operator-side computing device and the patient-side computing device includes, e.g., as illustrated in FIG. 4B, displaying, by the patient-side computing device, connection information on the screen of the patient-side computing device, and in response to receiving an input of the connection information by the operator-side computing device, establishing the wireless connection between the operator-side computing device and the patient-side computing device.

In some embodiments, the process 900 further includes: after establishing the communication, displaying visual desensitization information on the screen of the patient-side computing device to the patient, e.g., as illustrated in FIG. 4C. The eye-tracking device can be configured not to collect eye-tracking data of the patient while displaying the visual desensitization information.

In some embodiments, the process 900 further includes: while displaying the visual desensitization information, accessing, by the operator-side computing device, a web portal at the network-connected server to set up the session for the patient, e.g., as illustrated in FIGS. 4D and 4E. In some cases, setting up the session includes one of selecting the patient among a list of patients or creating a profile for the patient at the network-connected server.

In some embodiments, the process 900 further includes: determining a relative position between the eye-tracking device and at least one eye of the patient, and displaying an instruction to adjust a position of the eye-tracking device or a position of the patient on a user interface of the operator-side computing device, e.g., as illustrated in FIG. 4F. In some cases, the process 900 further includes: in response to determining that the relative location at least one eye of the patient is at a predetermined location in a detection area of the eye-tracking device, determining that the patient is aligned with the eye-tracking device.

At step 904, the patient is calibrated to the eye-tracking device by displaying one or more calibration targets on a screen of the patient-side computing device to the patient, e.g., as illustrated in FIG. 4G. Each of the one or more calibration targets can be sequentially presented at a corresponding predetermined location of the screen of the patient-side computing device, while capturing eye-tracking calibration data of the patient using the eye-tracking device. The process 900 can include: for each of the one or more calibration targets, processing the captured eye-tracking calibration data of the patient to determine a position of a corresponding visual fixation of the patient for the calibration target; comparing the position of the corresponding visual fixation of the patient with the corresponding predetermined location where the calibration target is presented; and determining whether the calibration target is calibrated to the eye-tracking device based on a result of the comparing.

In some embodiments, calibrating the patient to the eye-tracking device further includes: in response to determining that a deviation between the position of the corresponding visual fixation of the patient with the corresponding predetermined location is smaller than or equal to a predetermined threshold, determining that the calibration target is calibrated and displaying a next calibration target, or in response to determining that the deviation is greater than the predetermined threshold, determining that the calibration target fails to be calibrated and re-displaying the calibration target for calibration.

In some embodiments, the process 900 further includes: after calibrating the patient to the eye-tracking device, validating the calibration with one or more new calibration targets. Similar to the calibration described in step 904, validating the calibration includes: sequentially presenting each of the one or more new calibration targets at a corresponding predetermined location of the screen of the patient-side computing device, while capturing eye-tracking calibration data of the patient using the eye-tracking device, and processing the captured eye-tracking calibration data of the patient to determine a position of a corresponding visual fixation of the patient for each of the one or more new calibration targets.

In some embodiments, e.g., as illustrated in FIG. 4H, validating the calibration includes: simultaneously presenting, on a user interface of the operator-side computing device, the one or more new calibration targets at one or more corresponding predetermined locations and representations of the one or more corresponding visual fixations of the patient at the determined one or more positions; and in response to receiving an indication to validate a result of the calibrating, determining that the calibration is validated, or in response to receiving an indication to invalidate the result of the calibrating, starting to re-calibrate the patient to the eye-tracking device.

In some embodiments, validating the calibration includes: determining a number of new calibration targets that each passes a calibration based on the position of the corresponding visual fixation of the patent and the corresponding predetermined position; and if the number or an associated percentage is greater than or equal to a predetermined threshold, determining that the calibration is validated, or if the number or the associated percentage is smaller than the predetermined threshold, determining that the calibration is invalidated and starting to re-calibrate the patient to the eye-tracking device.

At step 906, subsequent to determining that the calibration is validated, a list of predetermined visual stimuli is sequentially presented on the screen of the patient-side computing device to the patient, while collecting eye-tracking data of the patient using the eye-tracking device.

In some embodiments, e.g., as illustrated in FIG. 4I, 4J, or 5, before presenting each of the list of predetermined visual stimuli, a centering target can be presented on the screen of the patient-side computing device to the patient for centering gaze of the patient.

In some embodiments, e.g., as illustrated in FIG. 5, a calibration of the patient to the eye-tracking device is performed between presenting two adjacent visual stimuli among the playlist of predetermined visual stimuli. The eye-tracking data collected in performing the calibration can be used for at least one of calibrating the eye-tracking data of the patient or for determining a calibration accuracy by the network-connected server.

In some embodiments, e.g., as illustrated in FIG. 4J, the process 900 further include: presenting, on a user interface of the operator-side computing device, at least one of: a progress indicator that keeps updating throughout presenting the playlist of predetermined visual stimuli, information of visual stimuli already presented or being presented, information of visual stimuli to be presented a user interface element for skipping a visual stimulus among the playlist of predetermined visual stimuli.

At step 908, session data of the session is transmitted by the patient-side computing device to the network-connected server, the session data including the eye-tracking data of the patient collected in the session. The patient-side computing device can automatically transmit the session data of the session to the network-connected server, in response to one of: determining a completion of presenting the playlist of predetermined visual stimuli on the screen, or receiving a completion indication of the session from the operator-side computing device, e.g., through the web portal on the network-connected server.

In some embodiments, the session data includes information related to the presented playlist of predetermined visual stimuli that can include names of presented predetermined visual stimuli and associated timestamps when the predetermined visual stimuli are presented, e.g., as illustrated in diagram (a) of FIG. 5. The session data can include the eye-tracking data and associated timestamps when the eye-tracking data are generated or collected, e.g., as illustrated in diagram (b) of FIG. 5. In some embodiments, transmitting the session data includes transmitting a first file storing the eye-tracking data of the patient and a second file storing the information related to the presented list of predetermined visual stimuli.

Figure 10:
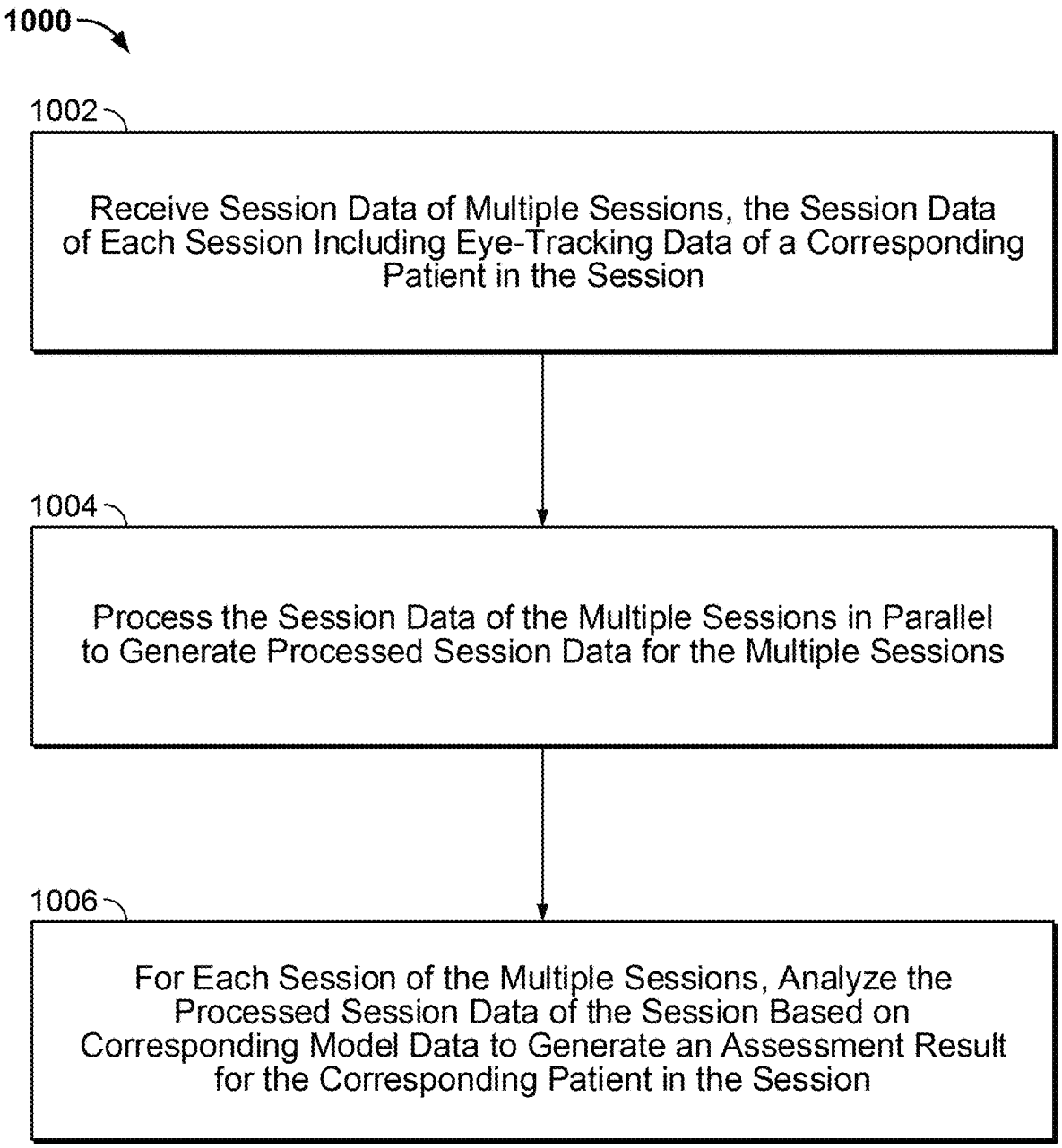
FIG. 10 is a flowchart of an example process for managing session data, according to one or more embodiments of the present disclosure.

FIG. 10 is a flowchart of an example process 1000 for data processing and analysis, according to one or more embodiments of the present disclosure. The process 1000 can be performed by a network-connected server that can be a cloud server in a cloud environment, e.g., the cloud server 110 of FIG. 1 or the cloud server as described in FIGS. 2A-2G. For example, the network server can include a platform, e.g., 112 of FIG. 1 or 220 of FIGS. 2A-2G, and a data pipeline system, e.g., 114 of FIG. 1 or 230 of FIGS. 2A-2G. The platform can include a web portal (e.g., 222 of FIGS. 2A-2G), an application data database (e.g., 224 of FIGS. 2A-2G), and a database (e.g., 226 of FIGS. 2A-2G). The data pipeline system can include one or more data processing modules (e.g., 232 of FIGS. 2A-2G) and one or more data analysis modules (e.g., 234 of FIGS. 2A-2G). The process 1000 can be similar to the process 600 of FIG. 6 or the process 700 of FIGS. 7A-7B.

At step 1002, session data of multiple sessions are received, e.g., as illustrated in FIG. 2B, and the session data of each session includes eye-tracking data of a corresponding patient in the session. At step 1004, the session data of the multiple sessions are processed in parallel to generate processed session data for the multiple sessions. At step 1006, for each session of the multiple sessions, the processed session data of the session is analyzed based on corresponding reference data to generate an assessment result for the corresponding patient in the session.

In some embodiments, the process 1000 further includes: loading the corresponding reference data for the multiple sessions in parallel with processing the session data of the multiple sessions.

In some embodiments, the network-connected server includes a plurality of processing cores. Processing the session data of the multiple sessions in parallel can include, e.g., as illustrated in step 716 of FIG. 7B, using a first plurality of processing cores to process the session data of the multiple sessions in parallel and using a second, different plurality of processing cores to load the corresponding reference data for the multiple sessions. A number of the first plurality of processing cores can be larger than a number of the second plurality of processing cores. In some embodiments, analyzing the processed session data of the multiple sessions based on the loaded corresponding reference data for the multiple sessions can include, e.g., as illustrated in step 718 of FIG. 7B, using the plurality of processing cores including the first plurality of processing cores and the second plurality of processing cores.

In some embodiments, analyzing the processed session data of the multiple sessions based on the loaded corresponding reference data for the multiple sessions includes at least one of: comparing the processed session data of the session to the corresponding reference data, inferring the assessment result for the corresponding patient from the processed session data using the corresponding reference data, or using at least one of a statistical model, a machine learning model, or an artificial intelligence (AI) model.

In some embodiments, the corresponding reference data includes historical eye-tracking data or results for patients having substantially same age or condition as the corresponding patient. In some embodiments, the process 1000 includes: generating the assessment result based on previous session data of the corresponding patient.

In some embodiments, for each session of the multiple sessions, a respective container is assigned for the session, e.g., as illustrated in FIG. 2C or 7A. The process 1000 can includes: in the respective container, processing the session data of the session and analyzing the processed session data of the session based on the corresponding model data to generate an assessment result for the corresponding patient in the session.

In some embodiments, the eye-tracking data is associated with a list of predetermined visual stimuli presented to the patient while the eye-tracking data is collected in the session, and the session data includes information associated with the list of predetermined visual stimuli in the session.

In some embodiments, the process 1000 further includes, e.g., as illustrated in FIG. 7A, in the respective container, breaking up the eye-tracking data into multiple portions based on the information associated with the list of predetermined visual stimuli, each portion of the eye-tracking data being associated with one of a respective predetermined visual stimulus or a corresponding calibration.

In some embodiments, processing the session data of the session includes processing portions of the eye-tracking data associated with respective predetermined visual stimulus based on information of the respective predetermined visual stimulus. In some embodiments, the process 1000 further includes: in the respective container, recalibrating portions of eye-tracking data associated with respective predetermined visual stimulus based on at least one portion of eye-tracking data associated with the corresponding calibration.

In some embodiments, the process 1000 further includes: in the respective container, determining a calibration accuracy using at least one portion of eye-tracking data associated with the corresponding calibration and a plurality of predetermined locations where a plurality of calibration targets are presented in the corresponding calibration.

In some embodiments, receiving the session data of the multiple sessions includes: receiving, through a web portal, the session data of the multiple sessions from a plurality of computing devices associated with corresponding entities, e.g., as illustrated in FIG. 2C.

In some embodiments, the process 1000 further includes, e.g., as illustrated in FIG. 7A, in response to receiving session data of a session, adding a file pointer for the session data of the session in a processing queue to be processed. The process 100 can further include: storing the session data of the session using the file pointer for the session in a database; and retrieving the session data of the session from the database using the file pointer for the session.

In some embodiments, the process 1000 further includes: for each entity, storing session data from one or more computing devices associated with the entity in a respective repository in the application data database, e.g., as illustrated in FIG. 2E. The respective repository can be isolated from one or more other repositories and inaccessible by one or more other entities. The application data database can be a NoSQL database.

In some examples, the respective repository for the entity includes, e.g., as illustrated in FIG. 2D, at least one of: information of the entity, information of one or more operators or operator-side computing devices associated with the entity, information of one or more patient-side computing devices associated with the entity, information of one or more sessions conducted in the entity, information of one or more patients associated with the entity, or history information of the respective repository.

In some embodiments, the process 1000 further includes: dynamically adjusting resources of the network-connected server based on a number of computing devices that access the network-connected server, e.g., as illustrated in FIG. 2F. The process 1000 can further include: replicating data of a first data center to a second data center, and in response to determining that the first data center is inaccessible, automatically directing traffic to the second data center.

In some embodiments, each of the first data center and the second data center includes at least one instance of a web portal accessible for the operator-side computing device, an operator application, or an application layer for data processing and data analysis, e.g., as illustrated in FIG. 2G. The process can further include: storing same data in multiple data centers. The data can include: application data for entities and information associated with the eye-tracking data.

In some embodiments, the process 1000 further includes: associating the generated assessment result with the corresponding patient in the session, and generating an assessment report for the corresponding patient, e.g., as illustrated in step 724 of FIG. 7B.

In some embodiments, the process 1000 further includes: outputting assessment results or assessment reports to be presented at a user interface of the operator-side computing device, e.g., through the web portal.

In some embodiments, e.g., as illustrated in FIG. 8A. the assessment report includes at least one of: information of the corresponding patient, information of an entity performing the session for the corresponding patient, information of a calibration accuracy in the session, information of session data collection, or the assessment result for the corresponding patient. In some embodiments, the assessment result indicates a likelihood that the corresponding patient has a developmental, cognitive, social, or mental disability or ability. For example, the assessment result indicates a likelihood that the corresponding patient has an Austin Spectrum Disorder (ASD) or a non-ASD. In some embodiments, the assessment result includes a respective score for each of one or more of social disability index, verbal ability index, and nonverbal ability, e.g., as illustrated in FIG. 8A.

In some embodiments, the corresponding patient has an age in a range from 5 months to 7 years, comprising an age in a range from 5 months to 43 months or 48 months, an age in a range from 16 to 30 months, an age in a range from 18 months to 36 months, an age in a range from 16 months to 48 months, or an age in a range from 16 months to 7 years.

Example Cloud Computing System Architecture

FIG. 11 is an example architecture 1100 for a cloud computing system (e.g., the cloud server 110 described in reference to FIG. 1 or the cloud server described in reference to FIGS. 2A-2G), according to one or more embodiments of the present disclosure. Other architectures are possible, including architectures with more or fewer components. In some implementations, architecture 1100 includes one or more processor(s) 1102 (e.g., dual-core Intel® Xeon® Processors), one or more network interface(s) 1106, one or more storage device(s) 1104 (e.g., hard disk, optical disk, flash memory) and one or more computer-readable medium(s) 1108 (e.g., hard disk, optical disk, flash memory, etc.). These components can exchange communications and data over one or more communication channel(s) 1110 (e.g., buses), which can utilize various hardware and software for facilitating the transfer of data and control signals between components.

The term "computer-readable medium" refers to any medium that participates in providing instructions to processor(s) 1102 for execution, including without limitation, non-volatile media (e.g., optical or magnetic disks), volatile media (e.g., memory) and transmission media. Transmission media includes, without limitation, coaxial cables, copper wire and fiber optics.

Computer-readable medium(s) 1108 can further include instructions 1112 for an operating system (e.g., Mac OS® server, Windows® NT server, Linux Server), instructions 1114 for network communications module, data processing instructions 1116, and interface instructions 1118.

Operating system can be multi-user, multiprocessing, multitasking, multithreading, real time, etc. Operating system performs basic tasks, including but not limited to: recognizing input from and providing output to devices 1102, 1104, 1106 and 1108; keeping track and managing files and directories on computer-readable medium(s) 1108 (e.g., memory or a storage device); controlling peripheral devices; and managing traffic on the one or more communication channel(s) 1110. Network communications module includes various components for establishing and maintaining network connections (e.g., software for implementing communication protocols, such as TCP/IP, HTTP, etc.) and for creating a distributed streaming platform using, for example, Apache Kafka™. Data processing instructions 1116 include server-side or backend software for implementing the server-side operations, as described in reference to FIG. 1. Interface instructions 1118 includes software for implementing a web server and/or portal for sending and receiving data to and from user side computing devices and service side computing devices.

Architecture 1100 can be implemented by a cloud computing system and can be included in any computer device, including one or more server computers in a local or distributed network each having one or more processing cores. Architecture 1100 can be implemented in a parallel processing or peer-to-peer infrastructure or on a single device with one or more processors. Software can include multiple software components or can be a single body of code.

Example Computing Devices

FIG. 12 illustrates an architecture for a computing device, according to one or more embodiments of the present disclosure. Referring now to FIG. 12, illustrated is a schematic diagram of a device 1200. Device 1200 includes processor 1204, memory 1206, storage component 1208, input interface 1210, output interface 1212, communication interface 1214, and bus 1202. In some embodiments, device 1200 corresponds to at least one of the patient-side computing device 130 or the operator-side computing device 140 of FIG. 1.

Bus 1202 includes a component that permits communication among the components of device 1200. In some embodiments, processor 1204 is implemented in hardware, software, or a combination of hardware and software. In some examples, processor 1204 includes a processor (e.g., a central processing unit (CPU), a graphics processing unit (GPU), an accelerated processing unit (APU), and/or the like), a microphone, a digital signal processor (DSP), and/or any processing component (e.g., a field-programmable gate array (FPGA), an application specific integrated circuit (ASIC), and/or the like) that can be programmed to perform at least one function. Memory 1206 includes random access memory (RAM), read-only memory (ROM), and/or another type of dynamic and/or static storage device (e.g., flash memory, magnetic memory, optical memory, and/or the like) that stores data and/or instructions for use by processor 1204.

Storage component 1208 stores data and/or software related to the operation and use of device 1200. In some examples, storage component 1208 includes a hard disk (e.g., a magnetic disk, an optical disk, a magneto-optic disk, a solid state disk, and/or the like), a compact disc (CD), a digital versatile disc (DVD), a floppy disk, a cartridge, a magnetic tape, a CD-ROM, RAM, PROM, EPROM, FLASH-EPROM, NV-RAM, and/or another type of computer readable medium, along with a corresponding drive.

Input interface 1210 includes a component that permits device 1200 to receive information, such as via user input (e.g., a touchscreen display, a keyboard, a keypad, a mouse, a button, a switch, a microphone, a camera, and/or the like). Additionally or alternatively, in some embodiments input interface 1210 includes a sensor that senses information (e.g., a global positioning system (GPS) receiver, an accelerometer, a gyroscope, an actuator, and/or the like). Output interface 1212 includes a component that provides output information from device 1200 (e.g., a display, a speaker, one or more light-emitting diodes (LEDs), and/or the like).

In some embodiments, communication interface 1214 includes a transceiver-like component (e.g., a transceiver, a separate receiver and transmitter, and/or the like) that permits device 1200 to communicate with other devices via a wired connection, a wireless connection, or a combination of wired and wireless connections. In some examples, communication interface 1214 permits device 1200 to receive information from another device and/or provide information to another device. In some examples, communication interface 1214 includes an Ethernet interface, an optical interface, a coaxial interface, an infrared interface, a radio frequency (RF) interface, a universal serial bus (USB) interface, a WiFi® interface, a cellular network interface, and/or the like.

In some embodiments, device 1200 performs one or more processes described herein. Device 1200 performs these processes based on processor 1204 executing software instructions stored by a computer-readable medium, such as memory 1206 and/or storage component 1208. A computer-readable medium (e.g., a non-transitory computer readable medium) is defined herein as a non-transitory memory device. A non-transitory memory device includes memory space located inside a single physical storage device or memory space spread across multiple physical storage devices.

In some embodiments, software instructions are read into memory 1206 and/or storage component 1208 from another computer-readable medium or from another device via communication interface 1214. When executed, software instructions stored in memory 1206 and/or storage component 1208 cause processor 1204 to perform one or more processes described herein. Additionally or alternatively, hardwired circuitry is used in place of or in combination with software instructions to perform one or more processes described herein. Thus, embodiments described herein are not limited to any specific combination of hardware circuitry and software unless explicitly stated otherwise.

Memory 1206 and/or storage component 1208 includes data storage or at least one data structure (e.g., a database and/or the like). Device 1200 is capable of receiving information from, storing information in, communicating information to, or searching information stored in the data storage or the at least one data structure in memory 1206 or storage component 1208. In some examples, the information includes network data, input data, output data, or any combination thereof.

In some embodiments, device 1200 is configured to execute software instructions that are either stored in memory 1206 and/or in the memory of another device (e.g., another device that is the same as or similar to device 1200). As used herein, the term "module" refers to at least one instruction stored in memory 1206 and/or in the memory of another device that, when executed by processor 1204 and/or by a processor of another device (e.g., another device that is the same as or similar to device 1200) cause device 1200 (e.g., at least one component of device 1200) to perform one or more processes described herein. In some embodiments, a module is implemented in software, firmware, hardware, and/or the like.

The number and arrangement of components illustrated in FIG. 12 are provided as an example. In some embodiments, device 1200 can include additional components, fewer components, different components, or differently arranged components than those illustrated in FIG. 12. Additionally or alternatively, a set of components (e.g., one or more components) of device 1200 can perform one or more functions described as being performed by another component or another set of components of device 1200.

The disclosed and other examples can be implemented as one or more computer program products, for example, one or more modules of computer program instructions encoded on a computer readable medium for execution by, or to control the operation of, data processing apparatus. The computer readable medium can be a machine-readable storage device, a machine-readable storage substrate, a memory device, or a combination of one or more them. The term "data processing apparatus" encompasses all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, or a combination of one or more of them.

A system may encompass all apparatus, devices, and machines for processing data, including by way of example a programmable processor, a computer, or multiple processors or computers. A system can include, in addition to hardware, code that creates an execution environment for the computer program in question, e.g., code that constitutes processor firmware, a protocol stack, a database management system, an operating system, or a combination of one or more of them.

A computer program (also known as a program, software, software application, script, or code) can be written in any form of programming language, including compiled or interpreted languages, and it can be deployed in any form, including as a standalone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed for execution on one computer or on multiple computers that are located at one site or distributed across multiple sites and interconnected by a communications network.

The processes and logic flows described in this document can be performed by one or more programmable processors executing one or more computer programs to perform the functions described herein. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer can include a processor for performing instructions and one or more memory devices for storing instructions and data. Generally, a computer can also include, or be operatively coupled to receive data from or transfer data to, or both, one or more mass storage devices for storing data, e.g., magnetic, magneto optical disks, or optical disks. However, a computer need not have such devices. Computer readable media suitable for storing computer program instructions and data can include all forms of nonvolatile memory, media and memory devices, including by way of example semiconductor memory devices, e.g., EPROM, EEPROM, and flash memory devices; magnetic disks. The processor and the memory can be supplemented by, or incorporated in, special purpose logic circuitry.

While this document may describe many specifics, these should not be construed as limitations on the scope of an invention that is claimed or of what may be claimed, but rather as descriptions of features specific to particular embodiments. Certain features that are described in this document in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination in some cases can be excised from the combination, and the claimed combination may be directed to a sub-combination or a variation of a sub-combination. Similarly, while operations are depicted in the drawings in a particular order, this should not be understood as requiring that such operations be performed in the particular order shown or in sequential order, or that all illustrated operations be performed, to achieve desirable results.

The foregoing is merely illustrative of the principles of the disclosure, and the systems, devices, and methods can be practiced by other than the described embodiments, which are presented for purposes of illustration and not of limitation. Although the embodiments and features herein are specifically described for use in connection with collecting and analyzing eye-tracking data of patients for the assessment, screening, monitoring, or diagnosis of autism spectrum disorders (ASD), it will be understood that the systems, devices, and methods may also apply to other developmental, cognitive social or mental abilities or disabilities, as well as other conditions, including but not limited to language disorders, intellectual disabilities, developmental disabilities with or without the presence of known genetic disorders, as well as attention deficit hyperactivity disorder (ADHD), attention deficit disorder (ADD), post-traumatic stress disorder (PTSD), head trauma, concussion, sports injuries, and dementia. It will be understood that such data, if not indicating measures for a disorder, may provide a measure of the degree of typicality of normative development, providing an indication of variability in typical development. Further, all of the components and other features outlined herein may be combined with one another in any suitable manner and may be adapted and applied to systems outside of medical diagnosis. For example, the interactive visual stimuli of the present disclosure may be used as a therapeutic tool. Further, the collected data may yield measures of certain types of visual stimuli that patients attend to preferentially. Such measures of preference have applications both in and without the fields of medical diagnosis and therapy, including, for example advertising or other industries where data related to visual stimuli preference is of interest.

A number of implementations have been described. Nevertheless, it will be understood that various modifications may be made without departing from the spirit and scope of the techniques and devices described herein. For example, phase perturbation or variation methods discussed above may be implemented in diffractive structures to remove high frequency artifacts or medium frequency artifacts in inference patterns. Features shown in each of the implementations may be used independently or in combination with one another. Additional features and variations may be included in the implementations as well. Accordingly, other implementations are within the scope of the following claims.

The invention claimed is:

1. A computer-implemented method of using an infrared eye-tracker camera of a handheld eye-tracker console that is wirelessly controlled by an operator-side handheld computer physically untethered from the handheld eye-tracker console, the method comprising:

wirelessly connecting the handheld eye-tracker console with the operator-side handheld computer via a cloud server that provides wireless communication between the operator-side handheld computer and the handheld eye-tracker console while both a display screen and the infrared eye-tracker camera of the handheld eye-tracker console are mechanically mounted together and oriented in a same direction and while the operator-side handheld computer is portable to different locations relative to the handheld eye-tracker console;

during said wireless communication between the operator-side handheld computer and the handheld eye-tracker console via the cloud server and in response to a command input at the operator-side handheld computer while a patient is oriented toward the handheld eye-tracker console, operating the infrared eye-tracker camera mounted adjacent to a periphery of the display screen of the handheld eye-tracker console to convert infrared-detected eye movements of the patient into a real-time data stream that includes pupil positions and gaze vectors during display of a predetermined sequence of stimulus videos on the display screen of the handheld eye-tracker console; and subsequent to said operating the infrared eye-tracker camera of the handheld eye-tracker in response to the command input at the operator-side handheld computer, automatically uploading to the cloud server without human intervention both a first file storing time-stamped eye-tracking gaze coordinate data of the patient collected during the display of the predetermined sequence of stimulus videos and a second file storing a playlist of the predetermined sequence of stimulus videos and associated timestamps of the predetermined sequence of stimulus videos.

2. The computer-implemented method of claim 1, wherein the operator-side handheld computer comprises an operator-side portable tablet computing device untethered from the handheld eye-tracker console and movable to a location outside the patient's field of view.

3. The computer-implemented method of claim 2, further comprising:
subsequent to wirelessly connecting the handheld eye-tracker console with the operator-side handheld computer via the cloud server, capturing an image of eyes of the patient using the handheld eye-tracker console while the patient is oriented toward the handheld eye-tracker console such that the captured image is indicative of a relative position between eyes of the patient and the infrared eye-tracker camera mechanically mounted adjacent to the periphery of the display screen of the handheld eye-tracker console; and
responsive to the captured image of the eyes of the patient indicating that the relative position between said eyes of the patient and the infrared eye-tracker camera of the handheld eye-tracker console is within the predetermined threshold, displaying on a user interface of the operator-side portable tablet computing device an indication that the patient is aligned with the infrared eye-tracker camera of the handheld eye-tracker console.

4. The computer-implemented method of claim 3, wherein:
said capturing said image of the eyes of the patient using the handheld eye-tracker console is initiated in response to operator input of a button selection on a user interface of the operator-side portable tablet computing device, which causes the cloud server to send a command to the handheld eye-tracker console to capture said image of the eyes of the patient.

5. The computer-implemented method of claim 1, wherein said wirelessly connecting the handheld eye-tracker console with the operator-side handheld computer via the cloud server comprises establishing a wireless connection between the operator-side handheld computer and the handheld eye-tracker console by:
accessing, by the operator-side handheld computer, a web portal at the cloud server; and
in response to receiving a selection of the handheld eye-tracker console at an onscreen interface of the operator-side handheld computer connected to the cloud server via the web portal, wirelessly connecting the operator-side handheld computer to the handheld eye-tracker console.

6. The computer-implemented method of claim 5, wherein said establishing the wireless connection between the operator-side handheld computer and the handheld eye-tracker console comprises:
displaying, by the handheld eye-tracker console, an access code automatically generated by the cloud server without human intervention on the display screen of the handheld eye-tracker console; and
in response to receiving manual user input of said access code at the operator-side handheld computer, establishing the wireless connection between the operator-side handheld computer and the handheld eye-tracker console.

7. The computer-implemented method of claim 1, further comprising:
subsequent to wirelessly connecting the handheld eye-tracker console with the operator-side handheld computer via the cloud server and prior to operating the infrared eye-tracker camera of the handheld eye-tracker console in response to the command at the operator-side handheld computer, displaying visual desensitization video on the display screen of the handheld eye-tracker console such that the desensitization video causes exogenous cueing by the patient without the need for verbal mediation or instruction.

8. The computer-implemented method of claim 7, further comprising: controlling the infrared eye-tracker camera of the handheld eye-tracker console to cease collection of eye-tracking data of the patient while displaying the visual desensitization video on the display screen of the handheld eye-tracker console.

9. The computer-implemented method of claim 8, further comprising: while the patient is oriented toward the visual desensitization video displayed on the display screen of the handheld eye-tracker console, receiving a selection of a patient profile for the patient at the operator-side handheld computer to set up the session for the patient.

10. The computer-implemented method of claim 9, wherein said receiving the selection of the patient profile at the operator-side handheld computer comprises: selecting the patient among a list of patients from the cloud server that is associated with the operator of the operator-side handheld computer.

11. The computer-implemented method of claim 1, further comprising:
subsequent to wirelessly connecting the handheld eye-tracker console with the operator-side handheld computer via the cloud server and prior to operating the infrared eye-tracker camera of the handheld eye-tracker console in response to the command at the operator-side handheld computer, displaying one or more calibration targets on the display screen of the handheld eye-tracker console to trigger a saccade towards, and the patient's fixation upon, a predetermined target location on the display screen of the handheld eye-tracker console, wherein said displaying one or more fixation targets at the handheld eye-tracker console is initiated in response to operator input of a calibration start command at the operator-side handheld computer.

12. The computer-implemented method of claim 11, wherein said displaying one or more calibration targets comprises: sequentially presenting each of the one or more calibration targets at a corresponding predetermined target location of the display screen of the handheld eye-tracker console while capturing eye-tracking calibration data of the patient using the infrared eye-tracker camera of the handheld eye-tracker console; and determining at the handheld eye-tracker console, for each of the one or more calibration targets and based upon the captured eye-tracking calibration data, a deviation between a position of the corresponding visual fixation of the patient with the corresponding predetermined target location.

13. The computer-implemented method of claim 12, further comprising:
in response to said determining at the handheld eye-tracker console that the deviation between the position of the corresponding visual fixation of the patient with the corresponding predetermined target location is smaller than or equal to a predetermined calibration threshold, determining that the calibration target is calibrated and displaying a next calibration target, or
in response to said determining at the handheld eye-tracker console that the deviation is greater than the predetermined calibration threshold, determining that the calibration target fails to be calibrated and re-displaying the calibration target for calibration.

14. The computer-implemented method of claim 1, further comprising changing the display screen of the handheld eye-tracker console to present a centering target prior to presenting each stimulus video in the predetermined sequence of stimulus videos on the display screen.

15. The computer-implemented method of claim 1, further comprising during said display of the predetermined sequence of stimulus videos on the display screen of the handheld eye-tracker console:
performing a calibration of the patient to the eye-tracker device of the handheld eye-tracker console between presenting two adjacent stimulus videos among the predetermined sequence of stimulus videos,
wherein the timestamped eye-tracking gaze coordinate data collected in performing the calibration is used for at least one of calibrating the eye-tracking data of the patient or for determining a calibration accuracy.

16. The computer-implemented method of claim 1, further comprising:
modifying a user interface of the operator-side handheld computer while the handheld eye-tracker console displays the predetermined sequence of stimulus videos on the display screen of the handheld eye-tracker console using an onscreen graphic indicator at the operator-side handheld computer that updates in response to completion of each stimulus video in the predetermined sequence of stimulus videos displayed at the handheld eye-tracker console.

17. The computer-implemented method of claim 1, wherein the operator-side handheld computer is configured to wirelessly communicate, via the cloud server, with said handheld eye-tracker console and multiple other handheld eye-tracker consoles, wherein said wirelessly connecting said handheld eye-tracker console with the operator-side handheld computer via the cloud server includes receiving a selection at an onscreen interface the operator-side handheld computer of said handheld eye-tracker console from among an onscreen listing of the multiple other handheld eye-tracker consoles.

18. The computer-implemented method of claim 1, wherein the operator-side handheld computer comprises a user interface that is different from the handheld eye-tracker console.

19. The computer-implemented method of claim 18, wherein the predetermined sequence of stimulus videos to be displayed on the handheld eye-tracker console is defined in response to the operator-side handheld computing device identifying an age of the patient.

20. The computer-implemented method of claim 1, wherein said operating the infrared eye-tracker camera of the handheld eye-tracker in response to the command input at the operator-side handheld computer comprises activating an infrared illumination source and an infrared sensor of the infrared eye-tracker camera so as to detect said infrared-detected eye movements of the patient.

21. The computer-implemented method of claim 1, wherein the cloud server comprises a web portal configured output an assessment report that displays one or more numeric index scores indicative of a severity of a developmental condition of the patient.

\* \* \* \* \*